(12) United States Patent
Hungenberg et al.

(10) Patent No.: US 8,877,684 B2
(45) Date of Patent: Nov. 4, 2014

(54) PESTICIDAL COMPOSITION COMPRISING A SYNTHETIC COMPOUND USEFUL AS NODULATION AGENT OF LEGUMINOUS PLANTS AND AN INSECTICIDE COMPOUND

(75) Inventors: Heike Hungenberg, Langenfeld (DE); Wolfgang Thielert, Odenthal (DE); Jean-Pierre Vors, Sainte Foy les Lyon (FR)

(73) Assignee: Bayer CropScience AG, Monheim (DE)

( * ) Notice: Subject to any disclaimer, the term of this patent is extended or adjusted under 35 U.S.C. 154(b) by 1057 days.

(21) Appl. No.: 12/448,147

(22) PCT Filed: Dec. 11, 2007

(86) PCT No.: PCT/EP2007/063639
§ 371 (c)(1),
(2), (4) Date: Aug. 4, 2009

(87) PCT Pub. No.: WO2008/071674
PCT Pub. Date: Jun. 19, 2008

(65) Prior Publication Data
US 2010/0048404 A1    Feb. 25, 2010

(30) Foreign Application Priority Data

Dec. 12, 2006  (EP) ..................................... 06356144

(51) Int. Cl.
*A01N 43/02*    (2006.01)
*A01N 43/00*    (2006.01)
*A01N 25/26*    (2006.01)
*A01N 43/04*    (2006.01)
*A61K 31/70*    (2006.01)
*A01N 43/16*    (2006.01)

(52) U.S. Cl.
CPC ...................................... *A01N 43/16* (2013.01)
USPC ........... 504/292; 504/100; 504/129; 504/140; 514/25; 514/62

(58) Field of Classification Search
CPC ...................................................... A01N 43/16
USPC ............... 504/292, 140, 129, 100; 514/25, 62
See application file for complete search history.

(56) References Cited

FOREIGN PATENT DOCUMENTS

WO    WO 2005/062899    7/2005
WO    WO 2005/063784    7/2005

OTHER PUBLICATIONS

Sur, R., Stork, A. (2003) Uptake, translocation and metabolism of imidacloprid in plants. Bulletin of Insectology, vol. 56, No. 1, p. 35-40.*
Robina, I., et al.: "Synthesis and conformational analysis of a lipotetrasaccharide related to the nodulation factor of Rhizobium bacteria", Tetrahedron, Asymmetry, Elsevier Science Publishers, vol. 8, No. 8, pp. 1207-1224, (1997) XP004059913, ISSN: 0957-4166.
Samain E., et al.: "Gram-scale synthesis of recombinant chitooligosaccharides in *Escherichia coli*", Carbohydr. Res. 302 (1997) 35-42.
Samain E., et al.: Production of O-acetylated and sulfated chitooliogoscaccharides by recombinant *Escherichi coli* strains harboring different combinations of *nod* genes, Journal of Biotechnology, 72 (1999) 33-47.
Jean-Maurice Mallet and Pierre Sinay, "19 Classics in Total Synthesis of Oligosaccharides and Glycoconjugates", Carbohydrates in Chemistry and Biology, Beat Ernst, Gerald W. Hart, Pierre Sinay, Wiley-VCH Verlag GmbH, (2000), pp. 468-491.
P.J. Kocienski, Protecting Groups, $2^{nd}$ Edition, Gerog Thieme Verlag, Suttgart, pp. 2-11, 186-189, 192-195 and 207-208 (2000).
Theodoro W. Green, P.G.M. Wuts, Protective Groups in Organic Synthesis, $3^{rd}$ Edition, Wiley, New York, (1999), p. 320-323, 326-331, 358-359.
A.I. Zinin et al., "Chemistry of Natural Compounds and Bioorganic Chemistry", Russian Chemical Bulletin, vol. 47, No. 3, (Mar. 1998) pp. 496-501.
John S. Debenham et al., J. Org. Chem., (1996) 61, pp. 6478-6479.
K.C. Nicolaou et al., Total Synthesis of the NodRm-IV Factors, the Rhizobium Nodulation Signals, J. Am. Chem. Soc., (1992) 114, pp. 8701-8702.
D. Tailler et al., "Total Synthesis of NodRmIV (S): a Sulfated Lipotetrasaccharide Symbiotic Signal from *Rhizobium meliloti*", J. Chem. Soc., Chem. Commun., pp. 1827-1828 (1994).
John S. Debenham et al., "TCP- and Phthalimide-Protected n-Pentenyl Glucosaminide Precursors for the Synthesis of Nodulation Factors As Illustrated by the Total Synthesis of NodRf-III (C18:1, MeFuc)", J. Org. Chem., 62, pp. 4591-4600 (1997).
S. Ikeshita et al., Tetrahedron Letters, vol. 35, No. 19, p. 3123 (1994), abstract.

(Continued)

*Primary Examiner* — Scarlett Goon

(57) ABSTRACT

A composition comprising at least a compound (a) of general formula (I):

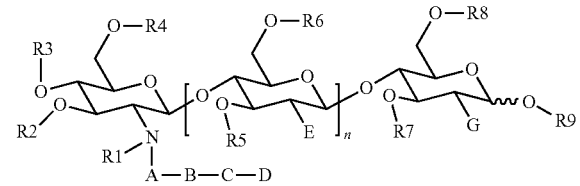

and an insecticide compound (b) in a (a)/(b) weight ratio of from 1/1 to $1/10^{13}$.

A composition further comprising an additional fungicidal compound.

A method for preventively or curatively combating the pests and diseases of crops and increasing their yield by using this composition.

18 Claims, No Drawings

(56) References Cited

OTHER PUBLICATIONS

L.X. Wang, et al., "Chemical Synthesis of NodRm-1: the Nodulation Factor Involved in *Rhizobium meliloti*-legume Synbiosis", J. Chem. Soc., Perkin Trans., 1, pp. 621-628 (1994).

S.R. Colby, "Calculating Synergistic and Antagonistic Responses of Herbicide Combinations", *Weeds*, 15, pp. 20-22 (1967).

U.S. Appl. No. 12/448,233, filed Aug. 4, 2009, by Anne Suty-Heinze et al., entitled "Pesticidal Composition Comprising a Synthetic Compound Useful As Nodulation Agent of Leguminous Plants and a Fungicide Compound".

* cited by examiner

PESTICIDAL COMPOSITION COMPRISING A SYNTHETIC COMPOUND USEFUL AS NODULATION AGENT OF LEGUMINOUS PLANTS AND AN INSECTICIDE COMPOUND

CROSS REFERENCE TO RELATED APPLICATION(S)

The present application is a 35 U.S.C. §371 national phase conversion of International Application No. PCT/EP2007/063639 filed Dec. 11, 2007, which claims priority of European Application No. 06356144.3 filed Dec. 12, 2006.

The present invention relates to novel pesticidal compositions comprising a synthetic compound useful as nodulation agent of leguminous plants and/or as plant growth stimulator and an insecticide compound. The present invention also relates to a method of combating or controlling pests and diseases by applying at a locus infested or liable to be infested such a composition.

International patent application WO 2005/063784 discloses a process for preparing synthetic lipochito-oligosaccharides (LCO), and discloses some of these compounds, called synthetic LCO factors, which are useful as nodulation agent of leguminous plants and/or as plant growth stimulators. These synthetic LCO factors are structurally different from the Nod factors isolated from natural bacterial organisms, and show different properties. Specifically, certain biologically active synthetic compounds show strong absorption in the ultraviolet range, which makes them easy to assay during their industrial preparation and allows them to be detected and assayed easily in the product intended for marketing, and allows their stability and storage in such products to be tested. In addition, some of these synthesized compounds show higher stability than the natural nod factors.

The possibility of combining one or more of these synthetic compounds useful as nodulation agent of leguminous plants and/or as plant growth stimulators with known fungicidal or insecticidal products is also disclosed. Nevertheless, no specific mention of potential insecticide partner is made in that document neither of any weight ratios in which synthetic LCO factor and insecticide partner should be present in that composition.

International patent application WO 2005/062899 discloses mixtures comprising a natural Nod factor and an insecticide. The natural nod factor comprised in such mixture is purified from bacterial sources, or is a synthetic or bioengineered version of naturally occurring nod gene products. However, the industrial preparation and conditioning of natural Nod factors presents two types of drawback: (1) the natural Nod factors are difficult to assay via simple methods such as spectrometric methods; (2) they are unstable in the presence of plants or in soils, in particular because they have a —CO—NH— bond that may be broken by plant or microbial enzymes present in the rhizosphere.

The novel pesticidal compositions described in the present application have demonstrated significant improvement in the combination over the individual treatments alone with respect to plant growth, vigor or yield of leguminous and non-leguminous plants or crops, and/or insecticide effect. A significant improvement in term of efficacy and stability with respect to mixtures comprising a natural nod factor or a synthetic or bioengineered version of such naturally occurring nod gene product and an insecticide has also been obtained.

It is always of high-interest in agriculture to use novel pesticidal mixtures showing a broader scope of activity.

We have now found some novel pesticidal compositions which possess the above mentioned characteristics.

Accordingly, the present invention relates to a composition comprising:
a) a compound of formula (I)

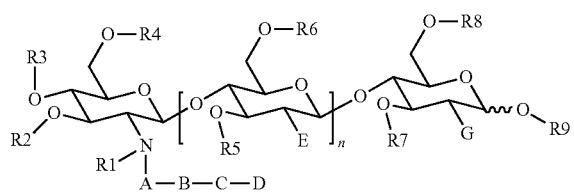

in which
n represents 1, 2 or 3;
A represents a substituent chosen from —C(O)—, —C(S)—, —CH2-, —CHR10-, —CR10R11-, —C(O)O—, —C(O)S—, —C(S)O—, —C(S)S—, —C(O)NH—, —C(NH)NH— and —C(S)NH—;
B represents
  an arylene;
  a heteroarylene comprising 1 or 2 hetero atoms chosen from nitrogen, oxygen and sulfur;
  a naphthylene;
  a heteronaphthylene comprising 1 or 2 hetero atoms chosen from nitrogen, oxygen and sulfur;
  a divalent radical derived from 2 fused aromatic rings of 5 or 6 atoms each;
  a divalent radical derived from 2 fused aromatic or heteroaromatic rings of 5 or 6 atoms each, comprising 1 or 2 hetero atoms chosen from nitrogen, oxygen and sulfur;
  a biphenylene;
  or a heterobiphenylene comprising 1 or 2 hetero atoms chosen from nitrogen, oxygen and sulfur;
  these groups possibly being substituted with one or two substituents R12 and R13 chosen, independently of each other, from halogen, CN, C(O)OR14, C(O)NR15R16, CF3, OCF3, —NO2, N3, OR14, SR14, NR15R16 and C1-6-alkyl;
C represents a substituent chosen from —O—, —S—, —CH2-, —CHR17-, —CR17R18- and —NR19;
D represents a linear or branched, saturated or unsaturated hydrocarbon-based chain containing from 2 to 20 carbon atoms;
E and G represent, independently of each other, a substituent chosen from H, OH, OR20, NH2 and NHR20;
R1 represents a substituent chosen from H, C1-6-alkyl, C(O)H and C(O)CH3;
R2, R3, R6, R14, R15, R16 and R19 represent, independently of each other, a substituent chosen from H, C1-6-alkyl, C(O)C1-6-alkyl, —C(S)C1-6-alkyl, —C(O)OC1-6-alkyl, —C(O)NH2, —C(S)NH2, —C(NH)NH2, —C(O)NHC1-6-alkyl, —C(S)NHC1-6-alkyl and —C(NH)NHC1-6-alkyl;
R4 represents a substituent chosen from H, C1-6-alkyl and R21;
R5 represents a substituent chosen from H, C1-6-alkyl, fucosyl and R22;
R7 represents a substituent chosen from H, C1-6-alkyl, arabinosyl and R23;
R8 represents a substituent chosen from H, C1-6-alkyl, fucosyl, methylfucosyl, sulfofucosyl, acetylfucosyl, arabinosyl, SO3H, SO3Li, SO3Na, SO3K, SO3N(C1-8alkyl)4 and R24;

R9 represents a substituent chosen from H, C1-6-alkyl, mannose, glycerol and R25;

R10, R11, R17 and R18 represent, independently of each other, a substituent chosen from C1-6-alkyl and F;

R20, R21, R22, R23, R24 and R25 represent, independently of each other, a substituent chosen from C(O)C1-6-alkyl, —C(S)C1-6-alkyl, —C(O)OC1-6-alkyl, —C(O)NH2, —C(S)NH2, —C(NH)NH2, —C(O)NHC1-6-alkyl, —C(S)NHC1-6-alkyl and —C(NH)NHC1-6-alkyl;

and also the possible geometrical and/or optical isomers, enantiomers and/or diastereoisomers, tautomers, salts, N-oxides, sulfoxides, sulfones, metal or metalloid complexes thereof, which are agriculturally acceptable. Among the compounds defined above, the most important compounds are the salts, more particularly the lithium, sodium, potassium or tetraalkylammonium salts;

and b) an insecticide compound.

in a (a)/(b) weight ratio of from 1/1 to $1/10^{13}$

The composition according to the present invention may provide a synergistic effect. This synergistic effect allows a reduction of the chemical substances spread into the environment and a reduction of the cost of the fungal treatment.

In the context of the present invention, the term "synergistic effect" is defined by Colby according to the article entitled "Calculation of the synergistic and antagonistic responses of herbicide combinations" Weeds, (1967), 15, pages 20-22.

The latter article mentions the formula:

$$E = x + y - \frac{x * y}{100}$$

in which E represents the expected percentage of inhibition of the disease for the combination of the two fungicides at defined doses (for example equal to x and y respectively), x is the percentage of inhibition observed for the disease by the compound (I) at a defined dose (equal to x), y is the percentage of inhibition observed for the disease by the compound (II) at a defined dose (equal to y). When the percentage of inhibition observed for the combination is greater than E, there is a synergistic effect.

The composition according to the present invention comprises a product of general formula (I). In a particular embodiment of the invention, the compounds of formula (I) have one or other of the following characteristics, taken separately or in combination:

n represents 2 or 3;
A represents —C(O)— or —CH$_2$—;
B represents a phenylene;
C represents —O—;
D represents a linear, saturated or unsaturated hydrocarbon-based chain containing from 3 to 17 carbon atoms;
E and G represent NHC(O)CH$_3$;
R$^1$ represents H, CH$_3$ or C(O)CH$_3$;
R$^2$, R$^3$, R$^5$, R$^6$, R$^7$, and R$^9$ represent H;
R$^4$ represents H, C(O)CH$_3$ or C(O)NH$_2$;
R$^8$ represents H, SO$_3$H, SO$_3$Li, SO$_3$Na, SO$_3$K, SO$_3$N(C$_{1-8}$alkyl)$_4$, fucosyl or methylfucosyl.

Among these compounds, the ones that are preferred are those of formula (I) simultaneously having the following characteristics:

n represents 2 or 3;
A represents —C(O)— or —CH$_2$—;
E and G represent NHC(O)CH$_3$;
R$^1$ represents H, CH$_3$ or C(O)CH$_3$;
R$^2$, R$^3$, R$^5$, R$^6$, R$^7$ and R$^9$ represent H;
R$^4$ represents H, C(O)CH$_3$ or C(O)NH$_2$;
R$^8$ represents H, SO$_3$H, SO$_3$Li, SO$_3$Na, SO$_3$K, SO$_3$N(C$_{1-8}$alkyl)$_4$, fucosyl or methylfucosyl;

even more preferably, those simultaneously having the following characteristics:

n represents 2 or 3;
A represents —C(O)— or —CH$_2$—;
D represents a linear, saturated or unsaturated hydrocarbon-based chain containing from 3 to 17 carbon atoms;
E and G represent NHC(O)CH$_3$;
R$^1$ represents H, CH$_3$ or C(O)CH$_3$;
R$^2$, R$^3$, R$^5$, R$^6$, R$^7$ and R$^9$ represent H;
R$^4$ represents H, C(O)CH$_3$ or C(O)NH$_2$;
R$^8$ represents H, SO$_3$H, SO$_3$Li, SO$_3$Na, SO$_3$K, SO$_3$N(C$_{1-8}$alkyl)$_4$, fucosyl or methylfucosyl;

and most preferably the compounds of formula (I) simultaneously having the following characteristics:

n represents 2 or 3;
A represents —C(O)— or —CH$_2$—;
C represents —O—;
D represents a linear, saturated or unsaturated hydrocarbon-based chain containing from 3 to 17 carbon atoms;
E and G represent NHC(O)CH$_3$;
R$^1$ represents H, CH$_3$ or C(O)CH$_3$;
R$^2$, R$^3$, R$^5$, R$^6$, R$^7$ and R$^9$ represent H;
R$^4$ represents H, C(O)CH$_3$ or C(O)NH$_2$;
R$^8$ represents H, SO$_3$H, SO$_3$Li, SO$_3$Na, SO$_3$K, SO$_3$N(C$_{1-8}$alkyl)$_4$, fucosyl or methylfucosyl.

Among these preferred compounds, mention may be made of the compounds of formula (I) simultaneously having the following characteristics:

n represents 2 or 3;
A represents —C(O)— or —CH$_2$—;
B represents a phenylene;
C represents —O—;
D represents a linear hydrocarbon-based chain containing 11 carbons, which is saturated, or unsaturated between carbons 4 and 5;
E and G represent NHC(O)CH$_3$;
R$^1$ represents H, CH$_3$ or C(O)CH$_3$;
R$^2$, R$^3$, R$^5$, R$^6$, R$^7$ and R$^9$ represent H$_3$;
R$^4$ represents H, C(O)CH$_3$ or C(O)NH$_2$;
R$^8$ represents H, SO$_3$H, SO$_3$Li, SO$_3$Na, SO$_3$K, SO$_3$N(C$_{1-8}$alkyl)$_4$, fucosyl or methylfucosyl.

Among the compositions of the present invention, the compositions comprising a compound (I) for which A represents a carbonyl group and which may be represented by formula (Ia) are particularly advantageous:

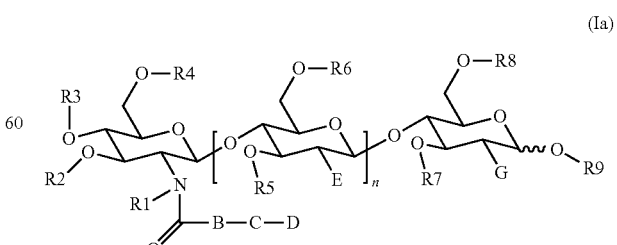

(Ia)

in which
- n represents 1, 2 or 3,
- B represents
  - an arylene;
  - a heteroarylene comprising 1 or 2 hetero atoms chosen from nitrogen, oxygen and sulfur;
  - a naphthylene;
  - a heteronaphthylene comprising 1 or 2 hetero atoms chosen from nitrogen, oxygen and sulfur;
  - a divalent radical derived from 2 fused aromatic rings containing 5 or 6 atoms each;
  - a divalent radical derived from 2 fused heteroaromatic rings containing 5 or 6 atoms each, and comprising 1 or 2 hetero atoms chosen from nitrogen, oxygen and sulfur;
  - a biphenylene;
  - or a heterobiphenylene comprising 1 or 2 hetero atoms chosen from nitrogen, oxygen and sulfur;
  - these groups possibly being substituted with one or two substituents $R^{12}$ and $R^{13}$ chosen, independently of each other, from halogen, CN, $C(O)OR^{14}$, $C(O)NR^{15}R^{16}$, $CF_3$, $OCF_3$, —$NO_2$, $N_3$, $OR^{14}$, $SR^{14}$, $NR^{15}R^{16}$ and $C_{1-6}$-alkyl;
- C represents a substituent chosen from —O—, —S—, —$CH_2$—, —$CHR^{17}$—, —$CR^{17}R^{18}$—, —NH— and —$NR^{19}$;
- D represents a linear or branched, saturated or unsaturated hydrocarbon-based chain containing from 2 to 20 carbon atoms;
- E and G represent, independently of each other, a substituent chosen from H, OH, $OR^{20}$, $NH_2$ and $NHR^{20}$;
- $R^1$ represents a substituent chosen from H, $C_{1-6}$-alkyl, C(O)H and $C(O)CH_3$;
- $R^2$, $R^3$ and $R^6$ represent, independently of each other, a substituent chosen from H, $C_{1-6}$-alkyl, $C(O)C_{1-6}$-alkyl, —$C(S)C_{1-6}$-alkyl, —$C(O)OC_{1-6}$-alkyl, —$C(O)NH_2$, —$C(S)NH_2$, —$C(NH)NH_2$, —$C(O)NHC_{1-6}$-alkyl, —$C(S)NHC_{1-6}$-alkyl and —$C(NH)NHC_{1-6}$-alkyl;
- $R^4$ represents a substituent chosen from H, $C_{1-6}$-alkyl and $R^{21}$;
- $R^5$ represents a substituent chosen from H, $C_{1-6}$-alkyl, fucosyl and $R^{22}$;
- $R^7$ represents a substituent chosen from H, $C_{1-6}$-alkyl, arabinosyl and $R^{23}$;
- $R^8$ represents a substituent chosen from H, $C_{1-6}$-alkyl, fucosyl, methylfucosyl, sulfofucosyl, acetylfucosyl, arabinosyl, $SO_3H$, $SO_3Li$, $SO_3Na$, $SO_3K$, $SO_3N(C_{1-8}alkyl)_4$ and $R^{24}$;
- $R^9$ represents a substituent chosen from H, $C_{1-6}$-alkyl, mannose, glycerol and
- $R^{10}$, $R^{11}$, $R^{17}$ and $R^{18}$ represent, independently of each other, a substituent chosen from $C_{1-6}$-alkyl and F;
- $R^{14}$, $R^{15}$, $R^{16}$ and $R^{19}$ represent, independently of each other, a substituent chosen from H, $C_{1-6}$-alkyl, —$C(O)C_{1-6}$-alkyl, —$C(S)C_{1-6}$-alkyl, —$C(O)OC_{1-6}$-alkyl, —$C(O)NH_2$, —$C(S)NH_2$, —$C(NH)NH_2$, —$C(O)NHC_{1-6}$-alkyl, —$C(S)NHC_{1-6}$-alkyl and —$C(NH)NHC_{1-6}$-alkyl;
- $R^{20}$, $R^{21}$, $R^{22}$, $R^{23}$, $R^{24}$ and $R^{25}$ represent, independently of each other, a substituent chosen from $C(O)C_{1-6}$-alkyl, —$C(S)C_{1-6}$-alkyl, —$C(O)OC_{1-6}$-alkyl, —$C(O)NH_2$, —$C(S)NH_2$, —$C(NH)NH_2$, —$C(O)NHC_{1-6}$-alkyl, —$C(S)NHC_{1-6}$-alkyl and —$C(NH)NHC_{1-6}$-alkyl;

and also the possible geometrical and/or optical isomers, enantiomers and/or diastereoisomers, tautomers, salts, N-oxides, sulfoxides, sulfones, metal or metalloid complexes thereof, which are agriculturally acceptable. Among the compounds defined above, the most important compounds are the salts, more particularly the lithium, sodium, potassium, or tetraalkylammonium salts.

Among these compounds of formula (Ia) the ones that are preferred are those having the following characteristics, taken separately or in combination:
- n represents 2 or 3;
- B represents a phenylene;
- C represents —O—;
- D represents a linear, saturated or unsaturated hydrocarbon-based chain containing from 3 to 17 carbon atoms;
- E and G represent $NHC(O)CH_3$;
- $R^1$ represents H or $CH_3$;
- $R^2$, $R^3$, $R^5$, $R^6$, $R^7$ and $R^9$ represent H;
- $R^4$ represents H, $C(O)CH_3$ or $C(O)NH_2$;
- $R^8$ represents H, $SO_3H$, $SO_3Li$, $SO_3Na$, $SO_3K$, $SO_3N(C_{1-8}alkyl)_4$, fucosyl or methylfucosyl;

more preferably, those simultaneously having the following characteristics:
- n represents 2 or 3;
- E and G represent $NHC(O)CH_3$;
- $R^1$ represents H or $CH_3$;
- $R^3$, $R^5$, $R^6$, $R^7$ and $R^9$ represent H;
- $R^4$ represents H, $C(O)CH_3$ or $C(O)NH_2$;
- $R^8$ represents H, $SO_3H$, $SO_3Li$, $SO_3Na$, $SO_3K$, $SO_3N(C_{1-8}alkyl)_4$, fucosyl or methylfucosyl;

even more preferably, those simultaneously having the following characteristics:
- n represents 2 or 3;
- D represents a linear, saturated or unsaturated hydrocarbon-based chain containing from 3 to 17 carbon atoms;
- E and G represent $NHC(O)CH_3$;
- $R^1$ represents H or $CH_3$;
- $R^2$, $R^3$, $R^5$, $R^6$, $R^7$ and $R^9$ represent H;
- $R^4$ represents H, $C(O)CH_3$ or $C(O)NH_2$;
- $R^8$ represents H, $SO_3H$, $SO_3Li$, $SO_3Na$, $SO_3K$, $SO_3N(C_{1-8}alkyl)_4$, fucosyl or methylfucosyl.

Among these compounds of formula (Ia), the ones that are more preferred are those simultaneously having the following characteristics:
- n represents 2 or 3;
- C represents —O—;
- D represents a linear, saturated or unsaturated hydrocarbon-based chain containing from 3 to 17 carbon atoms;
- E and G represent $NHC(O)CH_3$;
- $R^1$ represents H or $CH_3$;
- $R^2$, $R^3$, $R^5$, $R^6$, $R^7$ and $R^9$ represent H;
- $R^4$ represents H, $C(O)CH_3$ or $C(O)NH_2$;
- $R^8$ represents H, $SO_3H$, $SO_3Li$, $SO_3Na$, $SO_3K$, $SO_3N(C_{1-8}alkyl)_4$, fucosyl or methylfucosyl;

or those simultaneously having the following characteristics:
- n represents 2 or 3;
- B represents a phenylene;
- C represents —O—;
- D represents a linear hydrocarbon-based chain containing 11 carbons, which is saturated, or unsaturated between carbons 4 and 5;
- E and G represent $NHC(O)CH_3$;
- $R^1$ represents H or $CH_3$;
- $R^2$, $R^3$, $R^5$, $R^6$, $R^7$ and $R^9$ represent H;
- $R^4$ represents H, $C(O)CH_3$ or $C(O)NH_2$;
- $R^8$ represents H, $SO_3H$, $SO_3Li$, $SO_3Na$, $SO_3K$, $SO_3N(C_{1-8}alkyl)_4$, fucosyl or methylfucosyl.

Among the compositions of the present invention, the compositions comprising a compound (I) for which A represents a methylene group and which may be represented by formula (Ib) are also particularly advantageous:

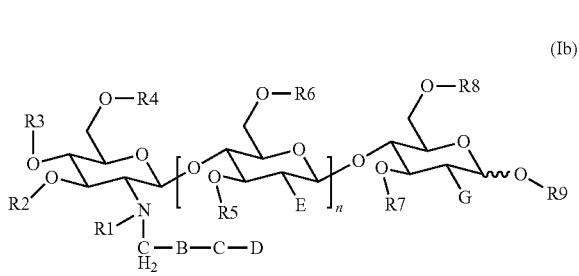

(Ib)

in which
n represents 1, 2 or 3;
B represents
an arylene;
a heteroarylene comprising 1 or 2 hetero atoms chosen from nitrogen, oxygen and sulfur;
a naphthylene;
a heteronaphthylene comprising 1 or 2 hetero atoms chosen from nitrogen, oxygen and sulfur;
a divalent radical derived from 2 fused aromatic rings each containing 5 or 6 atoms;
a divalent radical derived from 2 fused aromatic or heteroaromatic rings each containing 5 or 6 atoms, comprising 1 or 2 hetero atoms chosen from nitrogen, oxygen and sulfur;
a biphenylene;
or a heterobiphenylene comprising 1 or 2 hetero atoms chosen from nitrogen, oxygen and sulfur;
these groups possibly being substituted with one or two substituents $R^{12}$ and $R^{13}$ chosen, independently of each other, from halogen, CN, $C(O)OR^{14}$, $C(O)NR^{15}R^{16}$, $CF_3$, $OCF_3$, —$NO_2$, $N_3$, $OR^{14}$, $SR^{14}$, $NR^{15}R^{16}$ and $C_{1-6}$-alkyl;
C represents a substituent chosen from —O—, —S—, —$CH_2$—, —$CHR^{17}$—, —$CR^{17}R^{18}$—, —NH— and —$NR^{19}$;
D represents a linear or branched, saturated or unsaturated hydrocarbon-based chain containing from 2 to 20 carbon atoms;
E and G represent, independently of each other, a substituent chosen from H, OH, $OR^{20}$, $NH_2$ and $NHR^{20}$;
$R^1$ represents a substituent chosen from H, $C_{1-6}$-alkyl, $C(O)H$ and $C(O)CH_3$;
$R^2$, $R^3$ and $R^6$ represent, independently of each other, a substituent chosen from H, $C_{1-6}$-alkyl, $C(O)C_{1-6}$-alkyl, —$C(S)C_{1-6}$-alkyl, —$C(O)OC_{1-6}$-alkyl, —$C(O)NH_2$, —$C(S)NH_2$, —$C(NH)NH_2$, —$C(O)NHC_{1-6}$-alkyl, —$C(S)NHC_{1-6}$-alkyl and —$C(NH)NHC_{1-6}$-alkyl;
$R^4$ represents a substituent chosen from H, $C_{1-6}$-alkyl and $R^{21}$;
$R^5$ represents a substituent chosen from H, $C_{1-6}$-alkyl, fucosyl and $R^{22}$;
$R^7$ represents a substituent chosen from H, $C_{1-6}$-alkyl, arabinosyl and $R^{23}$;
$R^8$ represents a substituent chosen from H, $C_{1-6}$-alkyl, fucosyl, methylfucosyl, sulfofucosyl, acetylfucosyl, arabinosyl, $SO_3H$, $SO_3Li$, $SO_3Na$, $SO_3K$, $SO_3N(C_{1-8}alkyl)_4$ and $R^{24}$;
$R^9$ represents a substituent chosen from H, $C_{1-6}$-alkyl, mannose, glycerol and $R^{25}$;
$R^{10}$, $R^{11}$, $R^{17}$ and $R^{18}$ represent, independently of each other, a substituent chosen from $C_{1-6}$-alkyl and F;
$R^{14}$, $R^{15}$, $R^{16}$ and $R^{19}$ represent, independently of each other, a substituent chosen from H, $C_{1-6}$-alkyl, —$C(O)C_{1-6}$-alkyl, —$C(S)C_{1-6}$-alkyl, —$C(O)OC_{1-6}$-alkyl, —$C(O)NH_2$, —$C(S)NH_2$, —$C(NH)NH_2$, —$C(O)NHC_{1-6}$-alkyl, —$C(S)NHC_{1-6}$-alkyl and —$C(NH)NHC_{1-6}$-alkyl;
$R^{20}$, $R^{21}$, $R^{22}$, $R^{23}$, $R^{24}$ and $R^{25}$ represent, independently of each other, a substituent chosen from $C(O)C_{1-6}$-alkyl, —$C(S)C_{1-6}$-alkyl, —$C(O)OC_{1-6}$-alkyl, —$C(O)NH_2$, —$C(S)NH_2$, —$C(NH)NH_2$, —$C(O)NHC_{1-6}$-alkyl, —$C(S)NHC_{1-6}$-alkyl and —$C(NH)NHC_{1-6}$-alkyl;

and also the possible geometrical and/or optical isomers, enantiomers and/or diastereoisomers, tautomers, salts, N-oxides, sulfoxides, sulfones, metal or metalloid complexes thereof, which are agriculturally acceptable. Among the compounds defined above, the most important compounds are the salts, more particularly the lithium, sodium, potassium or tetraalkylammonium salts.

Among these compounds of formula (Ib) the ones that are preferred are those having the following characteristics, taken separately or in combination:
n represents 2 or 3;
B represents a phenylene;
C represents —O—;
D represents a linear, saturated or unsaturated hydrocarbon-based chain containing from 3 to 17 carbon atoms;
E and G represent $NHC(O)CH_3$;
$R^1$ represents H or $C(O)CH_3$;
$R^2$, $R^3$, $R^5$, $R^6$, $R^7$ and $R^9$ represent H;
$R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}alkyl)_4$, fucosyl or methylfucosyl; more preferably, those simultaneously having the following characteristics:
n represents 2 or 3;
E and G represent $NHC(O)CH_3$;
$R^1$ represents H or $C(O)CH_3$;
$R^2$, $R^3$, $R^5$, $R^6$, $R^7$ and $R^9$ represent H;
$R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}alkyl)_4$, fucosyl or methylfucosyl;
even more preferably, those simultaneously having the following characteristics:
n represents 2 or 3;
D represents a linear, saturated or unsaturated hydrocarbon-based chain containing from 3 to 17 carbon atoms;
E and G represent $NHC(O)CH_3$;
$R^1$ represents H or $C(O)CH_3$;
$R^2$, $R^3$, $R^5$, $R^6$, $R^7$ and $R^9$ represent H;
$R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}alkyl)_4$, fucosyl or methylfucosyl.

Among these compounds of formula (Ib), the ones that are more preferred are those simultaneously having the following characteristics:
n represents 2 or 3;
C represents —O—;
D represents a linear, saturated or unsaturated hydrocarbon-based chain containing from 3 to 17 carbon atoms;
E and G represent $NHC(O)CH_3$;
$R^1$ represents H or $C(O)CH_3$;
$R^2$, $R^3$, $R^5$, $R^6$, $R^7$ and $R^9$ represent H;
$R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}alkyl)_4$, fucosyl or methylfucosyl;
or those simultaneously having the following characteristics:
n represents 2 or 3;
B represents a phenylene;
C represents —O—;

D represents a linear hydrocarbon-based chain containing 11 carbons, which is saturated, or unsaturated between carbons 4 and 5;

E and G represent $NHC(O)CH_3$;

$R^1$ represents H or $C(O)CH_3$;

$R^2$, $R^3$, $R^5$, $R^6$, $R^7$ and $R^9$ represent H;

$R^4$ represents H, $C(O)CH_3$ or $C(O)NH_2$;

$R^8$ represents H, $SO_3H$, $SO_3Li$, $SO_3Na$, $SO_3K$, $SO_3N(C_{1-8}alkyl)_4$, fucosyl or methylfucosyl.

Among the compositions of the present invention, the compositions comprising a compound (I) for which C represents an oxygen atom and which may be represented by formula (Ic) are also particularly advantageous:

(Ic)

in which n represents 1, 2 or 3, preferably 2 or 3;

A represents a substituent chosen from —C(O)—, —C(S)—, —CH$_2$—, —CHR$^{10}$—, —CR$^{10}$R$^{11}$—, —C(O)O—, —C(O)S—, —C(S)O—, —C(S)S—, —C(O)NH—, —C(NH)NH— and —C(S)NH—, preferably —C(O)—;

B represents
an arylene;
a heteroarylene comprising 1 or 2 hetero atoms chosen from nitrogen, oxygen and sulfur;
a naphthylene;
a heteronaphthylene comprising 1 or 2 hetero atoms chosen from nitrogen, oxygen and sulfur;
a divalent radical derived from 2 fused aromatic rings containing 5 or 6 atoms each;
a divalent radical derived from 2 fused aromatic or heteroaromatic rings containing 5 or 6 atoms each, comprising 1 or 2 hetero atoms chosen from nitrogen, oxygen and sulfur;
a biphenylene;
or a heterobiphenylene comprising 1 or 2 hetero atoms chosen from nitrogen, oxygen and sulfur;
these groups possibly being substituted with one or two substituents $R^{12}$ and $R^{13}$ chosen, independently of each other, from halogen, CN, $C(O)OR^{14}$, $C(O)NR^{15}R^{16}$, $CF_3$, $OCF_3$, —$NO_2$, $N_3$, $OR^{14}$, $SR^{14}$, $NR^{15}R^{16}$ and $C_{1-6}$-alkyl;

D represents a linear or branched, saturated or unsaturated hydrocarbon-based chain containing from 2 to 20 carbon atoms, preferably a linear hydrocarbon-based chain containing 11 carbons, which is saturated, or unsaturated between carbons 4 and 5;

E and G represent, independently of each other, a substituent chosen from H, OH, $OR^{20}$, $NH_2$ and $NHR^{20}$, preferably $NHC(O)CH_3$;

$R^1$ represents a substituent chosen from H, $C_{1-6}$-alkyl, C(O)H and $C(O)CH_3$, preferably H or $CH_3$;

$R^2$, $R^3$ and $R^6$ represent, independently of each other, a substituent chosen from H, $C_{1-6}$-alkyl, —C(O)$C_{1-6}$-alkyl, —C(S)$C_{1-6}$-alkyl, —C(O)O$C_{1-6}$-alkyl, —C(O)NH$_2$, —C(S)NH$_2$, —C(NH)NH$_2$, —C(O)NHC$_{1-6}$-alkyl, —C(S)NHC$_{1-6}$-alkyl and —C(NH)NHC$_{1-6}$-alkyl; preferably H;

$R^4$ represents a substituent chosen from H, $C_{1-6}$-alkyl and $R^{21}$, preferably H, $C(O)CH_3$ or $C(O)NH_2$;

$R^5$ represents a substituent chosen from H, $C_{1-6}$-alkyl, fucosyl and $R^{22}$, preferably H;

$R^7$ represents a substituent chosen from H, $C_{1-6}$-alkyl, arabinosyl and $R^{23}$, preferably H;

$R^8$ represents a substituent chosen from H, $C_{1-6}$-alkyl, fucosyl, methylfucosyl, sulfofucosyl, acetylfucosyl, arabinosyl, $SO_3H$, $SO_3Li$, $SO_3Na$, $SO_3K$, $SO_3N(C_{1-8}alkyl)_4$ and $R^{24}$, preferably H, $SO_3H$, $SO_3Li$, $SO_3Na$, $SO_3K$, $SO_3N(C_{1-8}alkyl)_4$, fucosyl or methylfucosyl;

$R^9$ represents a substituent chosen from H, $C_{1-6}$-alkyl, mannose, glycerol and $R^{25}$, preferably H;

$R^{10}$, $R^{11}$, $R^{17}$ and $R^{18}$ represent, independently of each other, a substituent chosen from $C_{1-6}$-alkyl and F;

$R^{14}$, $R^{15}$, $R^{16}$ and $R^{19}$ represent, independently of each other, a substituent chosen from H, $C_{1-6}$-alkyl, —C(O)$C_{1-6}$-alkyl, —C(S)$C_{1-6}$-alkyl, —C(O)O$C_{1-6}$-alkyl, —C(O)NH$_2$, —C(S)NH$_2$, —C(NH)NH$_2$, —C(O)NHC$_{1-6}$-alkyl, —C(S)NHC$_{1-6}$-alkyl and —C(NH)NHC$_{1-6}$-alkyl;

$R^{20}$, $R^{21}$, $R^{22}$, $R^{23}$, $R^{24}$ and $R^{25}$ represent, independently of each other, a substituent chosen from $C(O)C_{1-6}$-alkyl, —C(S)$C_{1-6}$-alkyl, —C(O)O$C_{1-6}$-alkyl, —C(O)NH$_2$, —C(S)NH$_2$, —C(NH)NH$_2$, —C(O)NHC$_{1-6}$-alkyl, —C(S)NHC$_{1-6}$-alkyl and —C(NH)NHC$_{1-6}$-alkyl;

and also the possible geometrical and/or optical isomers, enantiomers and/or diastereoisomers, tautomers, salts, N-oxides, sulfoxides, sulfones, metal or metalloid complexes thereof, which are agriculturally acceptable. Among the compounds defined above, the most important compounds are the salts, more particularly the lithium, sodium, potassium or tetraalkylammonium salts.

Among the compounds of formula (Ic), the ones that are preferred are those having one or other of the following characteristics, taken separately or in combination:

n represents 2 or 3;

A represents —C(O)— or —CH$_2$—;

B represents a phenylene;

D represents a linear, saturated or unsaturated hydrocarbon-based chain containing from 3 to 17 carbon atoms;

E and G represent $NHC(O)CH_3$;

$R^1$ represents H, $CH_3$ or $C(O)CH_3$;

$R^2$, $R^3$, $R^5$, $R^6$, $R^7$ and $R^9$ represent H;

$R^4$ represents H, $C(O)CH_3$ or $C(O)NH_2$;

$R^8$ represents H, $SO_3H$, $SO_3Li$, $SO_3Na$, $SO_3K$, $SO_3N(C_{1-8}alkyl)_4$, fucosyl or methylfucosyl;

more preferably, those simultaneously having the following characteristics:

n represents 2 or 3;

A represents —C(O)— or —CH$_2$—;

E and G represent $NHC(O)CH_3$;

$R^1$ represents H, $CH_3$ or $C(O)CH_3$;

$R^2$, $R^3$, $R^5$, $R^6$, $R^7$ and $R^9$ represent H;

$R^4$ represents H, $C(O)CH_3$ or $C(O)NH_2$;

$R^8$ represents H. $SO_3H$, $SO_3Li$, $SO_3Na$, $SO_3K$, $SO_3N(C_{1-8}alkyl)_4$, fucosyl or methylfucosyl;

even more preferably, those simultaneously having the following characteristics:

n represents 2 or 3;

A represents —C(O)— or —CH$_2$—;

D represents a linear, saturated or unsaturated hydrocarbon-based chain containing from 3 to 17 carbon atoms;

E and G represent $NHC(O)CH_3$;

$R^1$ represents H, $CH_3$ or $C(O)CH_3$;
$R^2$, $R^3$, $R^5$, $R^6$, $R^7$ and $R^9$ represent H;
$R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}alkyl)_4$, fucosyl or methylfucosyl;
most preferably, those simultaneously having the following characteristics:
n represents 2 or 3;
A represents —C(O)— or —$CH_2$—;
B represents a phenylene;
D represents a linear hydrocarbon-based chain containing 11 carbon atoms, which is saturated, or unsaturated between carbons 4 and 5;
E and G represent $NHC(O)CH_3$;
$R^1$ represents H, $CH_3$ or $C(O)CH_3$;
$R^2$, $R^3$, $R^5$, $R^6$, $R^7$ and $R^9$ represent H;
$R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}alkyl)_4$, fucosyl or methylfucosyl.

Among the compositions of the present invention, the compositions comprising a compound (I) for which A represents a carbonyl group and C represents an oxygen atom, and which may be represented by formula (Id) are also particularly advantageous:

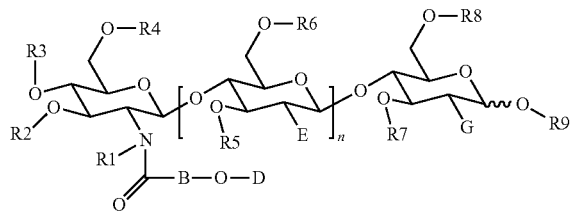

(Id)

in which
n represents 1, 2 or 3, preferably 2 or 3;
B represents
an arylene;
a heteroarylene comprising 1 or 2 hetero atoms chosen from nitrogen, oxygen and sulfur;
a naphthylene;
a heteronaphthylene comprising 1 or 2 hetero atoms chosen from nitrogen, oxygen and sulfur;
a divalent radical derived from 2 fused aromatic rings each containing 5 or 6 atoms;
a divalent radical derived from 2 fused aromatic or heteroaromatic rings each containing 5 or 6 atoms, comprising 1 or 2 hetero atoms chosen from nitrogen, oxygen and sulfur;
a biphenylene;
or a heterobiphenylene comprising 1 or 2 hetero atoms chosen from nitrogen, oxygen and sulfur;
these groups possibly being substituted with one or two substituents $R^{12}$ and $R^{13}$ chosen, independently of each other, from halogen, CN, $C(O)OR^{14}$, $C(O)NR^{15}R^{16}$, $CF_3$, $OCF_3$, —$NO_2$, $N_3$, $OR^{14}$, $SR^{14}$, $NR^{15}R^{16}$ and $C_{1-6}$-alkyl;
D represents a linear or branched, saturated or unsaturated hydrocarbon-based chain containing from 2 to 20 carbon atoms, preferably a linear hydrocarbon-based chain containing 11 carbon atoms, which is saturated, or unsaturated between carbons 4 and 5;

E and G represent, independently of each other, a substituent chosen from H, OH, $OR^{20}$, $NH_2$ and $NHR^{20}$, preferably $NHC(O)CH_3$;
$R^1$ represents a substituent chosen from H, $C_{1-6}$-alkyl, C(O)H and $C(O)CH_3$, preferably H or $CH_3$;
$R^2$, $R^3$ and $R^6$ represent, independently of each other, a substituent chosen from H, $C_{1-6}$-alkyl, —$C(O)C_{1-6}$-alkyl, —$C(S)C_{1-6}$-alkyl, —$C(O)OC_{1-6}$-alkyl, —$C(O)NH_2$, —$C(S)NH_2$, —$C(NH)NH_2$, —$C(O)NHC_{1-6}$-alkyl, —$C(S)NHC_{1-6}$-alkyl and —$C(NH)NHC_{1-6}$-alkyl; preferably H;
$R^4$ represents a substituent chosen from H, $C_{1-6}$-alkyl and $R^{21}$, preferably H, $C(O)CH_3$ or $C(O)NH_2$;
$R^5$ represents a substituent chosen from H, $C_{1-6}$-alkyl, fucosyl and $R^{22}$, preferably H;
$R^7$ represents a substituent chosen from H, $C_{1-6}$-alkyl, arabinosyl and $R^{23}$, preferably H;
$R^8$ represents a substituent chosen from H, $C_{1-6}$-alkyl, fucosyl, methylfucosyl, sulfofucosyl, acetylfucosyl, arabinosyl, $SO_3H$, $SO_3Li$, $SO_3Na$, $SO_3K$, $SO_3N(C_{1-8}alkyl)_4$ and $R^{24}$, preferably H, $SO_3H$, $SO_3Li$, $SO_3Na$, $SO_3K$, $SO_3N(C_{1-8}alkyl)_4$, fucosyl or methylfucosyl;
$R^9$ represents a substituent chosen from H, $C_{1-6}$-alkyl, mannose, glycerol and
$R^{25}$, preferably H;
$R^{10}$, $R^{11}$, $R^{17}$ and $R^{18}$ represent, independently of each other, a substituent chosen from $C_{1-6}$-alkyl and F;
$R^{14}$, $R^{15}$, $R^{16}$ and $R^{19}$ represent, independently of each other, a substituent chosen from H, $C_{1-6}$-alkyl, —$C(O)C_{1-6}$-alkyl, —$C(S)C_{1-6}$-alkyl, —$C(O)OC_{1-6}$-alkyl, —$C(O)NH_2$, —$C(S)NH_2$, —$C(NH)NH_2$, —$C(O)NHC_{1-6}$-alkyl, —$C(S)NHC_{1-6}$-alkyl and —$C(NH)NHC_{1-6}$-alkyl;
$R^{20}$, $R^{21}$, $R^{22}$, $R^{23}$, $R^{24}$ and $R^{25}$ represent, independently of each other, a substituent chosen from —$C(O)C_{1-6}$-alkyl, —$C(S)C_{1-6}$-alkyl, —$C(O)OC_{1-6}$-alkyl, —$C(O)NH_2$, —$C(S)NH_2$, —$C(NH)NH_2$, —$C(O)NHC_{1-6}$-alkyl, —$C(S)NHC_{1-6}$-alkyl and —$C(NH)NHC_{1-6}$-alkyl;
and also the possible geometrical and/or isomers, enantiomers and/or diastereoisomers, tautomers, salts, N-oxides, sulfoxides, sulfones and metal or metalloid complexes thereof, which are agriculturally acceptable. Among the compounds defined above, the most important compounds are the salts, more particularly the lithium, sodium, potassium or tetraalkylammonium salts.

Among the compounds of formula (Id), the ones that are preferred are those having one or other of the following characteristics, taken separately or in combination;
n represents 2 or 3;
B represents a phenylene;
D represents a linear, saturated or unsaturated hydrocarbon-based chain containing from 3 to 17 carbon atoms;
E and G represent $NHC(O)CH_3$;
$R^1$ represents H or $CH_3$;
$R^2$, $R^3$, $R^5$, $R^6$, $R^7$, and $R^9$ represent H;
$R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}alkyl)_4$, fucosyl or methylfucosyl;
more preferably, those simultaneously having the following characteristics:
n represents 2 or 3;
E and G represent $NHC(O)CH_3$;
$R^1$ represents H or $CH_3$;
$R^2$, $R^3$, $R^5$, $R^6$, $R^7$ and $R^9$ represent H;
$R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}alkyl)_4$, fucosyl or methylfucosyl;

even more preferably, those simultaneously having the following characteristics:

n represents 2 or 3;
D represents a linear, saturated or unsaturated hydrocarbon-based chain containing from 3 to 17 carbon atoms;
E and G represent $NHC(O)CH_3$;
$R^1$ represents H or $CH_3$;
$R^2, R^3, R^5, R^6, R^7$ and $R^9$ represent H;
$R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}alkyl)_4$, fucosyl or methylfucosyl;

and most preferably those simultaneously having the following characteristics:

n represents 2 or 3;
B represents a phenylene;
D represents a linear hydrocarbon-based chain containing 11 carbon, which is saturated, or unsaturated between carbons 4 and 5;
E and G represent $NHC(O)CH_3$;
$R^1$ represents H or $CH_3$;
$R^2, R^3, R^5, R^6, R^7$ and $R^9$ represent H;
$R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}alkyl)_4$, fucosyl or methylfucosyl.

Among the compositions of the present invention, the compositions comprising a compound (I) for which A represents a methylene group and C represents an oxygen atom, and which may be represented by formula (Ie) are also particularly advantageous:

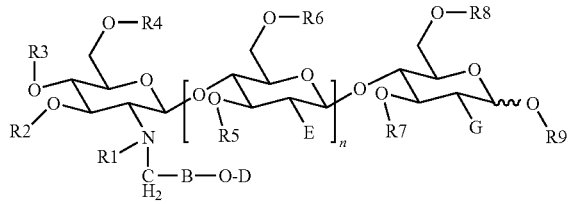

(Ie)

in which
n represents 1, 2 or 3, preferably 2 or 3;
B represents
  an arylene;
  a heteroarylene comprising 1 or 2 hetero atoms chosen from nitrogen, oxygen and sulfur;
  a naphthylene;
  a heteronaphthylene comprising 1 or 2 hetero atoms chosen from nitrogen, oxygen and sulfur;
  a divalent radical derived from 2 fused aromatic rings containing 5 or 6 atoms each;
  a divalent radical derived from 2 fused aromatic or heteroaromatic rings containing 5 or 6 atoms each, comprising 1 or 2 hetero atoms chosen from nitrogen, oxygen and sulfur;
  a biphenylene;
  or a heterobiphenylene comprising 1 or 2 hetero atoms chosen from nitrogen, oxygen and sulfur;
  these groups possibly being substituted with one or two substituents $R^{12}$ and $R^{13}$ chosen, independently of each other, from halogen, CN, $C(O)OR^{14}$, $C(O)NR^{15}R^{16}$, $CF_3$, $OCF_3$, $-NO_2$, $N_3$, $OR^{14}$, $SR^{14}$, $NR^{15}R^{16}$ and $C_{1-6}$-alkyl;
D represents a linear or branched, saturated or unsaturated hydrocarbon-based chain containing from 2 to 20 carbon atoms, preferably a linear hydrocarbon-based chain containing 11 carbons, which is saturated, or unsaturated between carbons 4 and 5;
E and G represent, independently of each other, a substituent chosen from H, OH, $OR^{20}$, $NH_2$ and $NHR^{20}$, preferably $NHC(O)CH_3$;
$R^1$ represents a substituent chosen from H, $C_{1-6}$-alkyl, $C(O)H$ and $C(O)CH_3$, preferably H or $CH_3$;
$R^2, R^3$ and $R^6$ represent, independently of each other, a substituent chosen from H, $C_{1-6}$-alkyl, $C(O)C_{1-6}$-alkyl, $-C(S)C_{1-6}$-alkyl, $-C(O)OC_{1-6}$-alkyl, $-C(O)NH_2$, $-C(S)NH_2$, $-C(NH)NH_2$, $-C(O)NHC_{1-6}$-alkyl, $-C(S)NHC_{1-6}$-alkyl and $-C(NH)NHC_{1-6}$-alkyl; preferably H;
$R^4$ represents a substituent chosen from H, $C_{1-6}$-alkyl and $R^{21}$, preferably H, $C(O)CH_3$ or $C(O)NH_2$;
$R^5$ represents a substituent chosen from H, $C_{1-6}$-alkyl, fucosyl and $R^{22}$, preferably H;
$R^7$ represents a substituent chosen from H, $C_{1-6}$-alkyl, arabinosyl and $R^{23}$, preferably H;
$R^8$ represents a substituent chosen from H, $C_{1-6}$-alkyl, fucosyl, methylfucosyl, sulfofucosyl, acetylfucosyl, arabinosyl, $SO_3H$, $SO_3Li$, $SO_3Na$, $SO_3K$, $SO_3N(C_{1-8}alkyl)_4$ and $R^{24}$, preferably H, $SO_3H$, $SO_3Li$, $SO_3Na$, $SO_3K$, $SO_3N(C_{1-8}alkyl)_4$, fucosyl or methylfucosyl;
$R^9$ represents a substituent chosen from H, $C_{1-6}$-alkyl, mannose, glycerol and $R^{25}$, preferably H;
$R^{10}, R^{11}, R^{17}$ and $R^{18}$ represent, independently of each other, a substituent chosen from $C_{1-6}$-alkyl and F;
$R^{14}, R^{15}, R^{16}$ and $R^{19}$ represent, independently of each other, a substituent chosen from H, $C_{1-6}$-alkyl, $-C(O)C_{1-6}$-alkyl, $-C(S)C_{1-6}$-alkyl, $-C(O)OC_{1-6}$-alkyl, $-C(O)NH_2$, $-C(S)NH_2$, $-C(NH)NH_2$, $-C(O)NHC_{1-6}$-alkyl, $-C(S)NHC_{1-6}$-alkyl and $-C(NH)NHC_{1-6}$-alkyl;
$R^{20}, R^{21}, R^{22}, R^{23}, R^{24}$ and $R^{25}$ represent, independently of each other, a substituent chosen from $C(O)C_{1-6}$-alkyl, $-C(S)C_{1-6}$-alkyl, $-C(O)OC_{1-6}$-alkyl, $-C(O)NH_2$, $-C(S)NH_2$, $-C(NH)NH_2$, $-C(O)NHC_{1-6}$-alkyl, $-C(S)NHC_{1-6}$-alkyl and $-C(NH)NHC_{1-6}$-alkyl;

and also the possible geometrical and/or optical isomers, enantiomers and/or diastereoisomers, tautomers, salts, N-oxides, sulfoxides, sulfones and metal or metalloid complexes thereof, which are agriculturally acceptable. Among the compounds defined above, the most important compounds are the salts, more particularly the lithium, sodium, potassium or tetraalkylammonium salts.

Among the compounds of (Ie), the ones that are preferred are those having one or other of the following characteristics, taken separately or in combination:

n represents 2 or 3;
B represents a phenylene;
D represents a linear, saturated or unsaturated hydrocarbon-based chain containing from 3 to 17 carbon atoms;
E and G represent $NHC(O)CH_3$;
$R^1$ represents H or $C(O)CH_3$;
$R^2, R^3, R^5, R^6, R^7$ and $R^9$ represent H;
W $R^4$ represents H, $C(O)CH_3$ or $C(O)NH_2$;
$R^8$ represents H, $SO_3H$, $SO_3Li$, $SO_3Na$, $SO_3K$, $SO_3N(C_{1-8}alkyl)_4$, fucosyl or methylfucosyl;

more preferably, those simultaneously having the following characteristics:

n represents 2 or 3;
E and G represent $NHC(O)CH_3$;
$R^1$ represents H or $C(O)CH_3$;
$R^2, R^3, R^5, R^6, R^7$ and $R^9$ represent H;
$R^4$ represents H, $C(O)CH_3$ or $C(O)NH_2$;

R¹ represents H, SO₃H, SO₃Li, SO₃Na, SO₃K, SO₃N(C₁₋₈alkyl)₄, fucosyl or methylfucosyl;

even more preferably, those simultaneously having the following characteristics:
- n represents 2 or 3;
- D represents a linear, saturated or unsaturated hydrocarbon-based chain containing from 3 to 17 carbon atoms;
- E and G represent NHC(O)CH₃;
- R¹ represents H or C(O)CH₃;
- R², R³, R⁵, R⁶, R⁷ and R⁹ represent H;
- R⁴ represents H, C(O)CH₃ or C(O)NH₂;
- R⁸ represents H, SO₃H, SO₃Li, SO₃Na, SO₃K, SO₃N(C₁₋₈alkyl)₄, fucosyl or methylfucosyl;

and most preferably those simultaneously having the following characteristics:
- n represents 2 or 3;
- B represents a phenylene;
- D represents a linear hydrocarbon-based chain containing 11 carbons, which is saturated, or unsaturated between carbons 4 and 5;
- E and G represent NHC(O)CH₃;
- R¹ represents H or C(O)CH₃;
- R², R³, R⁵, R⁶, R⁷ and R⁹ represent H;
- R⁴ represents H, C(O)CH₃ or C(O)NH₂;
- R⁸ represents H, SO₃H, SO₃Li, SO₃Na, SO₃K, SO₃N(C₁₋₈alkyl)₄, fucosyl or methylfucosyl.

Among the compositions comprising a compound of formula (I), (Ia), (Ib), (Ic), (Id) or (Ie) according to the invention, the ones that are preferred are those for which:
B represents a substituent chosen from:

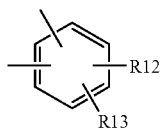
B1

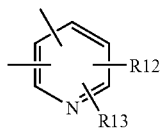
B2

B3

B4

B5

B6

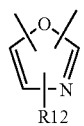
B7

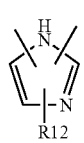
B8

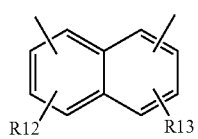
B9

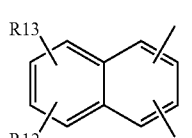
B10

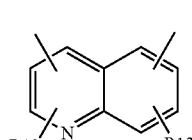
B11

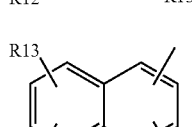
B12

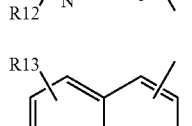
B13

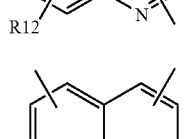
B14

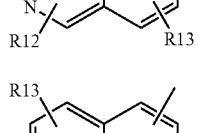
B15

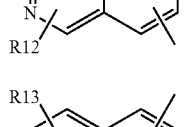
B16

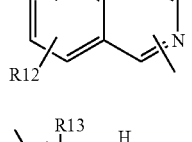
B17

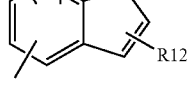

-continued

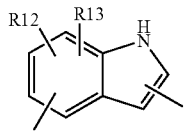

B18

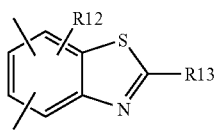

B19

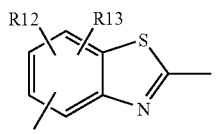

B20 in which $R^{12}$ and $R^{13}$ represent two substituents chosen, independently of each other, from halogen, CN, CF$_3$, OCF$_3$, —NO$_2$, N$_3$, ORE, SR$^{14}$, NR$^{15}$R$^{16}$ and C$_{1-6}$-alkyl.

Among the compositions comprising a compound of formula (I), (Ia), (Ib), (Ic), (Id) or (Ie) according to the invention, the ones that are also preferred are those for which B represents
  an arylene;
  a heteroarylene comprising 1 or 2 hetero atoms chosen from nitrogen, oxygen and sulfur;
  a naphthylene;
  or a heteronaphthylene comprising 1 or 2 hetero atoms chosen from nitrogen, oxygen and sulfur;
  these groups possibly being substituted with one or two substituents $R^{12}$ and $R^{13}$ chosen, independently of each other, from halogen, CN, C(O)OR$^{14}$, C(O)NR$^{15}$R$^{16}$, CF$_3$, OCF$_3$, —NO$_2$, N$_3$, OR$^{14}$, SR$^{14}$, NR$^{15}$R$^{16}$ and C$_{1-6}$-alkyl;

preferably, those for which

B represents
  an arylene;
  or a heteroarylene comprising 1 or 2 hetero atoms chosen from nitrogen, oxygen and sulfur;
  these groups possibly being substituted with one or two substituents $R^{12}$ and $R^{13}$ chosen, independently of each other, from halogen, CN, C(O)OR$^{14}$, C(O)NR$^{15}$R$^{16}$, CF$_3$, OCF$_3$, —NO$_2$, N$_3$, OR$^{14}$, SR$^{14}$, NR$^{15}$R$^{16}$ and C$_{1-6}$-alkyl; more preferably, those for which B represents
  a phenylene;
  or a heterophenylene comprising 1 or 2 hetero atoms chosen from nitrogen, oxygen and sulfur;
  these groups possibly being substituted with one or two substituents $R^{12}$ and $R^{13}$ chosen, independently of each other, from halogen, CN, C(O)OR$^{14}$, C(O)NR$^{15}$R$^{16}$, CF$_3$, OCF$_3$, —NO$_2$, N$_3$, OR$^{14}$, SR$^{14}$, NR$^{15}$R$^{16}$ and C$_{1-6}$-alkyl;

mention may be made especially of those for which

B represents a phenylene B1 that may be substituted with one or two substituents $R^{12}$ and $R^{13}$ chosen, independently of each other, from halogen, CN, CF$_3$, OCF$_3$, —NO$_2$, N$_3$, OR$^4$, SR$^{14}$, NR$^{15}$R$^{16}$ and C$_{1-6}$-alkyl.

Among the preferred compositions of the present invention, mention may also be made of those comprising a compound (I) having one of the following characteristics, taken separately or in combination:

n=2 or 3;
A represents —C(O)— or —CH$_2$—;
C represents —O—;
E and G represent NHC(O)CH$_3$;
$R^1$ represents H or C(O)CH$_3$;
$R^2$, $R^3$, $R^5$, $R^6$ and $R^7$ represent a hydrogen atom;
$R^4$ represents a substituent chosen from H, C(O)CH$_3$ and C(O)NH$_2$;
$R^8$ represents a substituent chosen from H, fucosyl, methylfucosyl, sulfofucosyl, acetylfucosyl, arabinosyl, SO$_3$H, SO$_3$Li, SO$_3$Na, SO$_3$K and SO$_3$N(C$_{1-8}$alkyl)$_4$;
$R^9$ represents a hydrogen atom;

even more preferably, those having the following combination of characteristics:

n=2 or 3;
A represents —C(O)— or —CH$_2$—;
C represents —O—;
D represents a linear, saturated or unsaturated hydrocarbon-based chain containing from 7 to 15 carbon atoms; preferably a hydrocarbon-based chain according to one of the formulae represented below

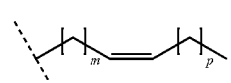

D1

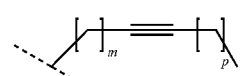

D2

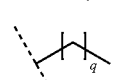

D3

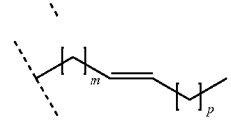

D4

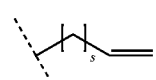

D5

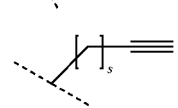

D6 in which
m=1 to 12
p=0 to 11
q=6 to 14
s=5 to 13
with m+p≤12 and m+p≥4; even more preferably a hydrocarbon-based chain according to one of the formulae represented below

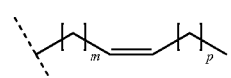

D1

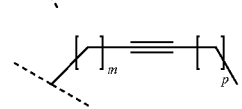

D2

-continued

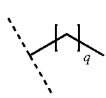

in which
m=1 to 12
p=0 to 11
q=6 to 14
with m+p≤12 and m+p≥4; and most preferably a linear hydrocarbon-based chain containing 11 carbon atoms, which is saturated, or unsaturated between carbon atoms 4 and 5;

E and G represent $NHC(O)CH_3$;

$R^1$ represents H or $C(O)CH_3$;

$R^2$, $R^3$, $R^5$, $R^6$ and $R^7$ represent a hydrogen atom;

$R^4$ represents a substituent chosen from H, $C(O)CH_3$ and $C(O)NH_2$;

$R^8$ represents a substituent chosen from H, fucosyl, methylfucosyl, sulfofucosyl, acetylfucosyl, arabinosyl, $SO_3H$, $SO_3Li$, $SO_3Na$, $SO_3K$ and $SO_3N(C_{1-8}alkyl)_4$;

$R^9$ represents a hydrogen atom;

in particular, the compounds for which $R^8$ represents H, $SO_3H$, $SO_3Li$, $SO_3Na$, $SO_3K$, $SO_3N(C_{1-8}alkyl)_4$ or a substituent of formula:

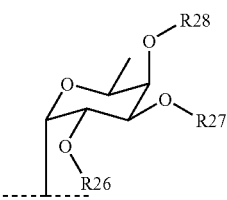

in which
$R^{26}$ represents a substituent chosen from H and $CH_3$, preferably H;
$R^{27}$ and $R^{28}$ represent, independently of each other, a substituent chosen from H, $C(O)CH_3$, $SO_3H$, $SO_3Li$, $SO_3Na$, $SO_3K$ and $SO_3N(C_{1-8}alkyl)_4$, preferably $R^{27}$ and $R^{28}$ represent H.

As examples of compositions according to the invention that are particularly advantageous and preferred, mention may be made of the compositions comprising a compound selected from the list L1 of the compounds having the following formulaes:

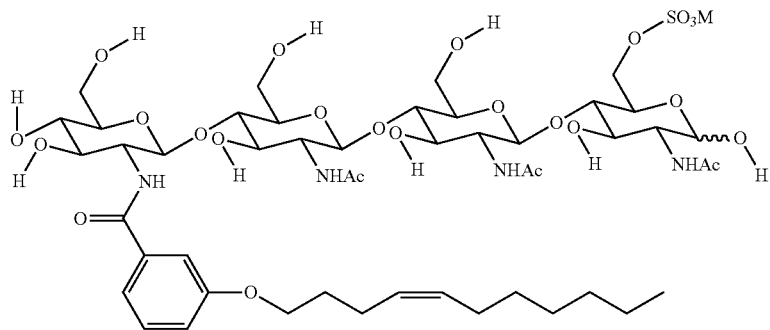

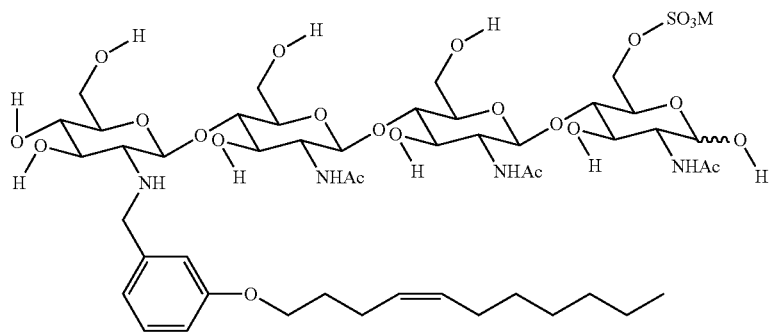

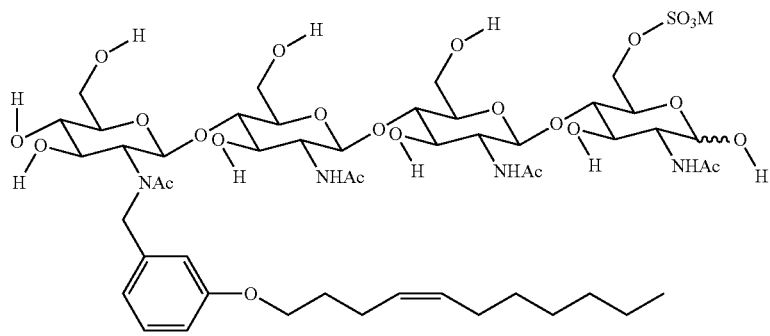

-continued
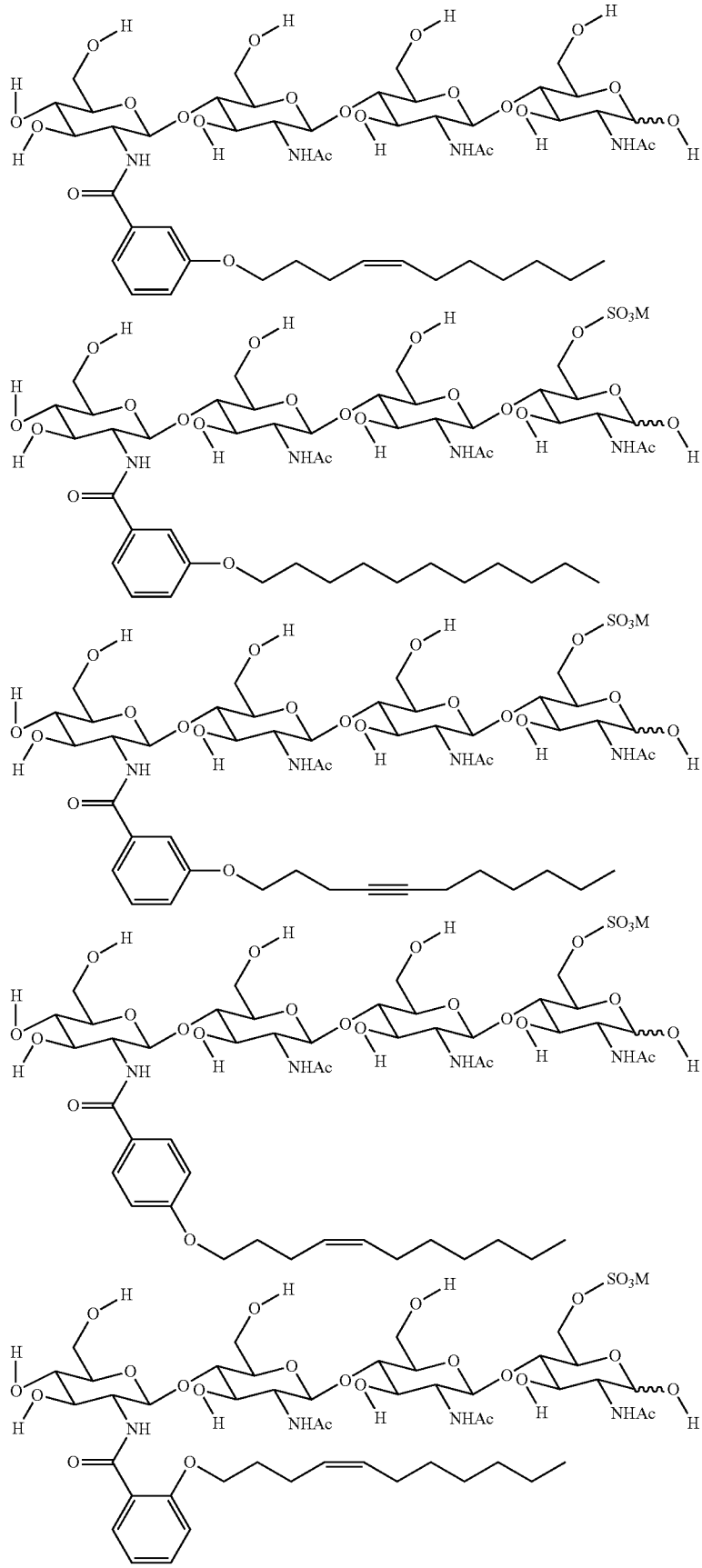

-continued
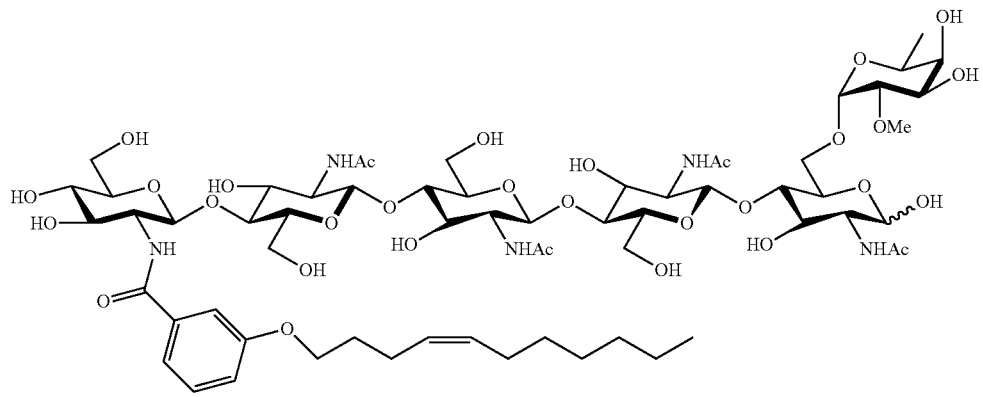
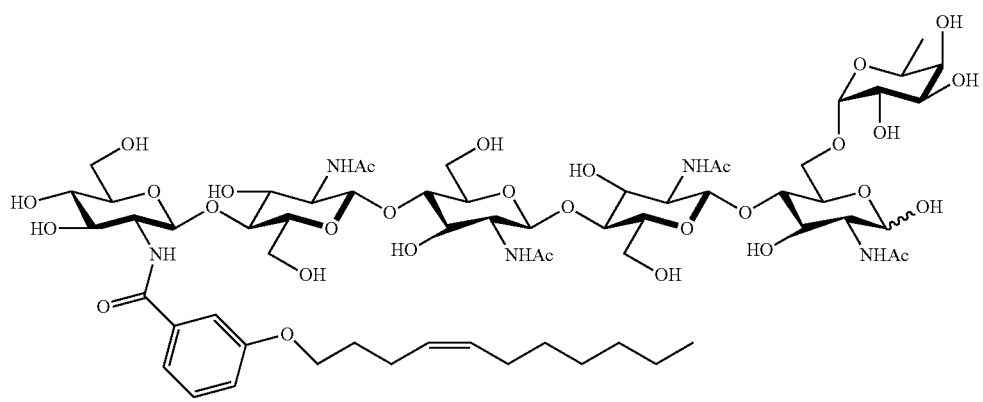
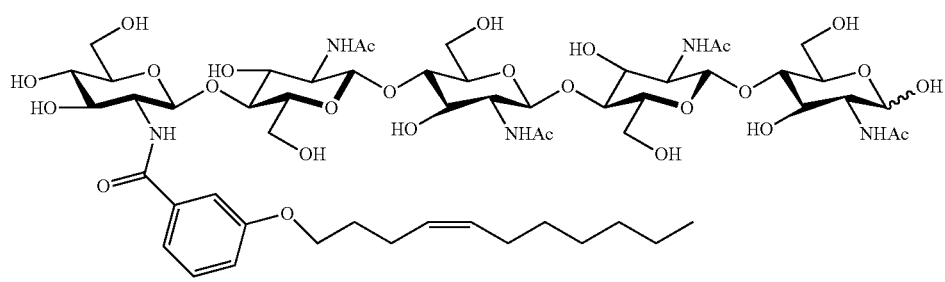
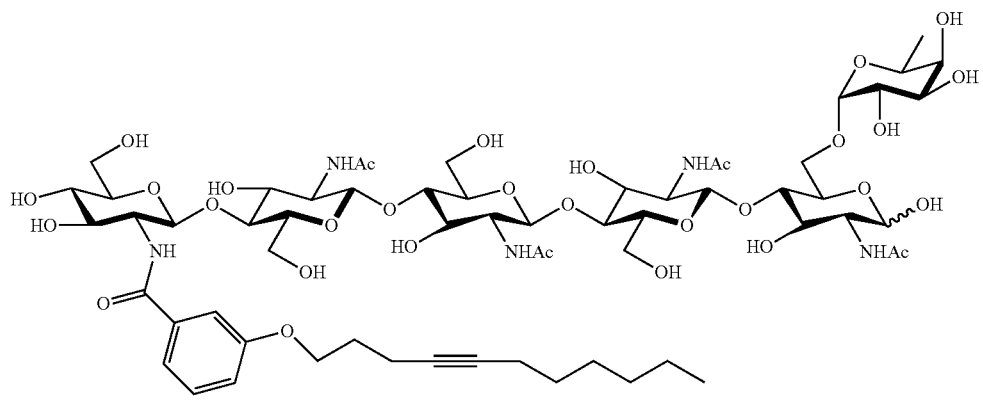

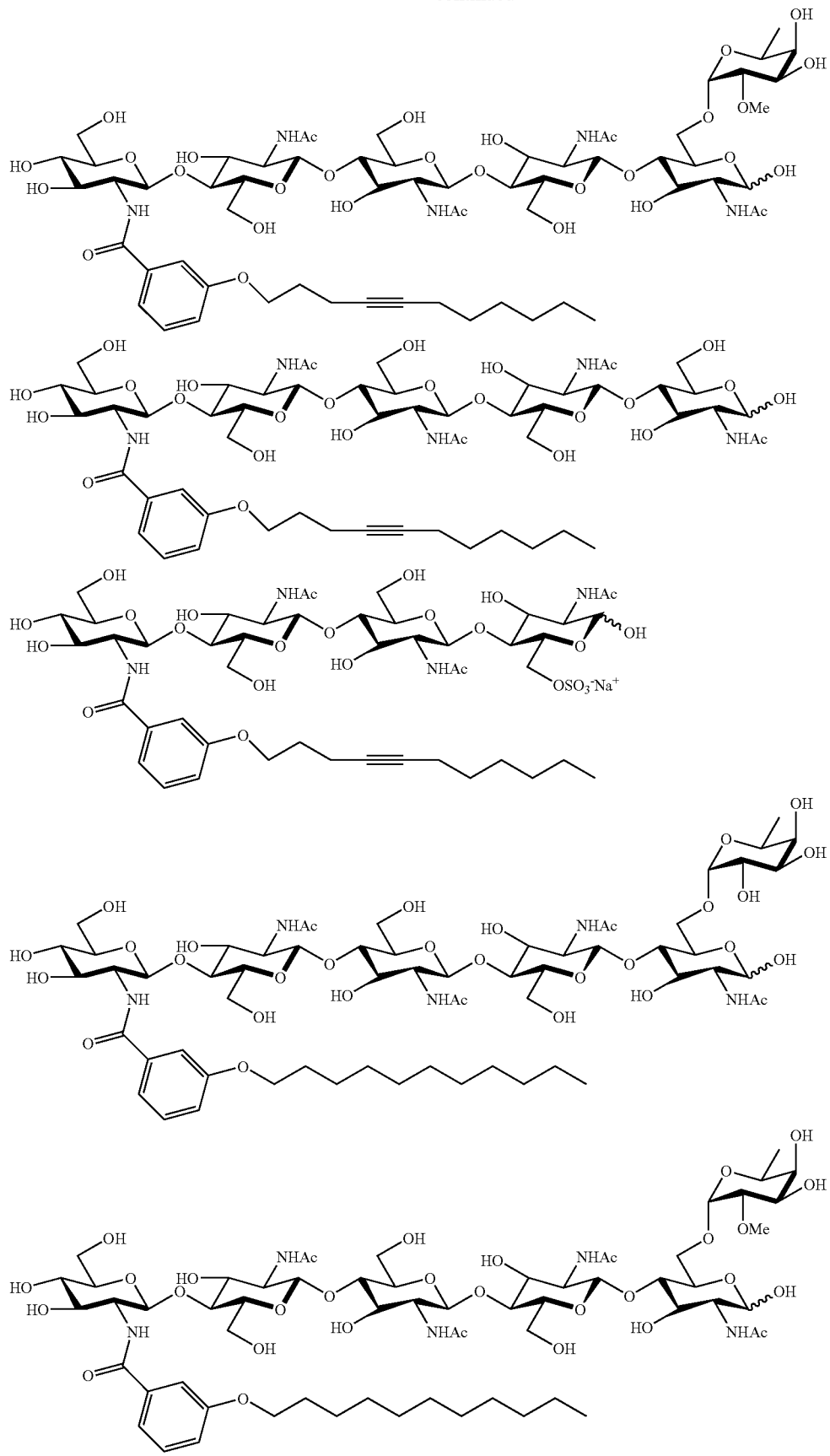

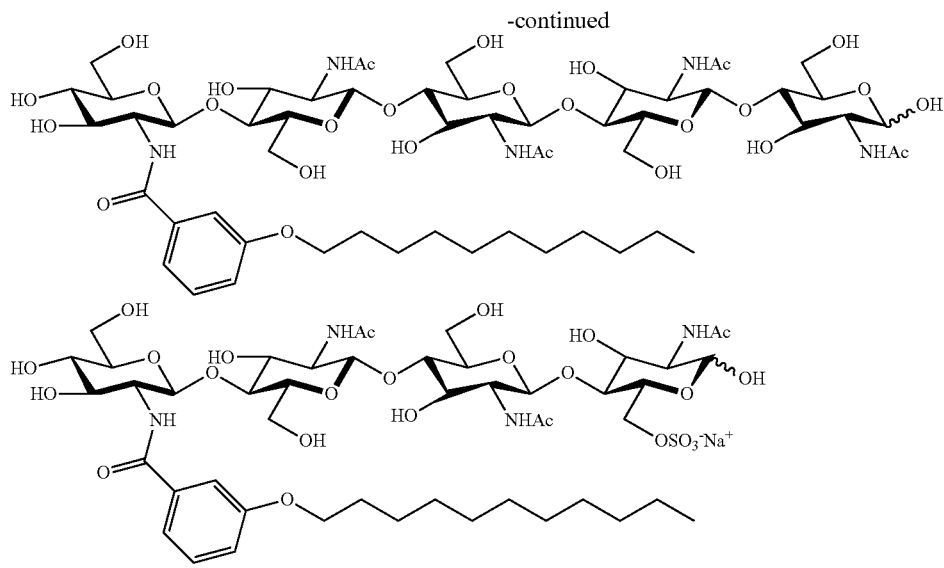

in which, when it is present, M represents a cation chosen from $H^+$, $Li^+$, $Na^+$, $K^+$ and $(C_{1-8}alkyl)_4N^+$.

Besides the compositions of the invention that have just been specifically described the variants of combinations of possible substituents for the formulae (I), (Ia), (Ib), (Ic), (Id) and (Ie) especially, also form part of the invention.

It is known that a chitin oligomer not containing a lipid chain is not active, and that the degradation of the Nod factors by breaking the amide bond in the rhizosphere thus leads to a loss of activity.

In order to limit, or even prevent, this degradation, a serie of analogous compounds, some of which are more stable than the natural Nod factors, was prepared. Examples of such compounds (I) according to the invention are disclosed further in the present patent application.

The composition according to the present invention comprises an insecticide compound (b). Suitable insecticide are chosen in the following groups:

b1) acetylcholine receptor agonists/antagonists such as chloronicotinyls/neonicotinoids, nicotine, bensultap or cartap. Suitable examples of chloronicotinyls/neonicotinoids include acetamiprid, clothianidin, dinotefuran, imidacloprid, imidaclothiz, nitenpyram, nithiazine, thiacloprid, thiamethoxam;

b2) acetylcholinesterase (AChE) inhibitors such as carbamates and organophosphates. Suitable examples of carbamates include alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, chloethocarb, dimetilan, ethiofencarb, fenobucarb, fenothiocarb, formetanate, furathiocarb, isoprocarb, metam-sodium, methiocarb, methomyl, metolcarb, oxamyl, phosphocarb, pirimicarb, promecarb, propoxur, thiodicarb, thiofanox, triazamate, trimethacarb, XMC and xylylcarb. Suitable examples of organophosphates include acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetam-phos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon and vamidothion;

b3) sodium channel modulators/voltage-gated sodium channel blockers such as pyrethroids and oxadiazines. Suitable examples of pyrethroids include acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, DDT, deltamethrin, empenthrin (IR-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (IR-isomer), tralocythrin, tralomethrin, transfluthrin, ZXI 8901 and pyrethrins (pyrethrum). Suitable example of oxadiazines includes indoxacarb;

b4) semicarbazon such as metaflumizon (BAS3201)

b5) acetylcholine receptor modulators such as spinosyns. Suitable example of spinosyns includes spinosad and spinetoram;

b6) GABA-gated chloride channel antagonists such as cyclodiene organochlorines and fiproles. Suitable examples of cyclodiene organochlorines include camphechlor, chlordane, endosulfan, gamma-HCH, HCH, heptachlor, lindane and methoxychlor. Suitable examples of fiproles include acetoprole, ethiprole, fipronil, pyrafluprole, pyriprole and vaniliprole;

b7) chloride channel activators such as mectins. Suitable examples of mectins include abamectin, avermectin, emamectin, emamectin-benzoate, ivermectin, lepimectin, milbemectin and milbemycin;

b8) juvenile hormone mimetics such as diofenolan, epofenonane, fenoxycarb, hydroprene, kinoprene, methoprene, pyriproxifen, triprene;

b9) ecdysone agonists/disruptors such as diacylhydrazines. Suitable examples of diacylhydrazines include chromafenozide, halofenozide, methoxyfenozide and tebufenozide;

b10) inhibitors of chitinbiosynthesis such as benzoylureas, buprofezin and cyromazine. Suitable examples of benzoylureas include bistrifluoron, chlofluazuron, diflubenzuron, fluazuron, flucycloxuron, flufenoxuron, hexaflumuron, lufenuron, novaluron, noviflumuron, penfluoron, teflubenzuron and triflumuron;

b11) inhibitors of oxidative phosphorylation, ATP disruptors such as organotins and diafenthiuron. Suitable examples of organotins include azocyclotin, cyhexatin and fenbutatin oxide;

b12) decouplers of oxidative phosphorylation by disruption of the H proton gradient such as pyrroles and dinitrophenols. Suitable example of pyrroles includes chlorfenapyr. Suitable examples of dinitrophenols include binapacyrl, dinobuton, dinocap, meptyldinocarp and DNOC;

b13) site I electron transport inhibitors such as METIs, hydramethylnone and dicofol. Suitable examples of METIs include fenazaquin, fenpyroximate, pyrimidifen, pyridaben, tebufenpyrad, tolfenpyrad;

b14) site II electron transport inhibitors such as rotenone;

b15) site III electron transport inhibitors such as acequinocyl and fluacrypyrim;

b16) microbial disrupters of the intestinal membrane of insects such as *Bacillus thuringiensis* strains;

b17) inhibitors of lipid synthesis such as tetronic acids and tetramic acids. Suitable examples of tetronic acids include spirodiclofen, spiromesifen and spirotetramat. Suitable examples of tetramic acids include cis-3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS Reg. No.: 382608-10-8) and carbonic acid, cis-3-(2,5-dimethylphenyl)-8-methoxy-2-oxo-1-azaspiro[4.5]dec-3-en-4-yl ethyl ester (CAS reg. No.: 203313-25-1);

b18) carboxamides such as flonicamid;

b19) octopaminergic agonists such as amitraz;

b20) inhibitors of the magnesium-stimulated ATPase such as propargite;

b21) ryanodin receptor agonists such as phthalamides or Rynaxypyr (3-bromo-N-{4-chloro-2-methyl-6-[(methylamino)carbonyl]phenyl}-1-(3-chloropyridin-2-yl)-1H-pyrazole-5-carboxamide). Suitable example of phthalamides includes $N^2$-[1,1-dimethyl-2-(methylsulphonyl)ethyl]-3-iodo-$N^1$-[2-methyl-4-[1,2,2,2-tetrafluoro-1-(trifluoromethyl)ethyl]phenyl]-1,2-benzenedicarboxamide (i.e. flubendiamide, CAS Reg. No.: 272451-65-7);

b22) nereistoxin analogues such as thiocyclam hydrogen oxalate and thiosultap-sodium;

b23) biologics, hormones or pheromones such as azadirachtin, *Bacillus* spec., *Beauveria* spec., codlemone, *Metarrhizium* spec., *Paecilomyces* spec., thuringiensin and *Verticillium* spec;

b24) active compounds having unknown or non-specified mechanisms of action such as fuimigants, selective feeding inhibitors, mite growth inhibitors, amidoflumet; benclothiaz, benzoximate, bifenazate, bromopropylate, buprofezin, chinomethioat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbonitrile (CAS reg. No. 185982-80-3) and the corresponding 3-endo isomer (CAS reg. No. 185984-60-5) (cf. WO 96/37494, WO 98/25923), and also preparations comprising insecticidal effective plant extracts, nematodes, fungi or viruses. Suitable examples of fumigants include aluminium phosphide, methyl bromide and sulphuryl fluoride. Suitable examples of selective feeding inhibitors include cryolite, flonicamid and pymetrozine. Suitable examples of mite growth inhibitors include clofentezine, etoxazole and hexythiazox.

Preferably, the insecticide compound (b) is chosen as being abamectin, acephate, acetamiprid, acrinathrin, aldicarb, alpha-cypermethrin, beta-cyfluthrin, bifenthrin, carbaryl, carbofuran, chlorfenapyr, chlorfluazuron, chlorpyrifos-E, clothianidin, cyfluthrin, cypermethrin, cyromazine, deltamethrin, diflubenzuron, diflubenzuron, dinotefuran, emamectin-b., ethiprole, fenpyroximate, fipronil, flonicamid, flubendiamide, flufenoxuron, gamma-cyhalothrin, hexaflumuron, imidacloprid, indoxacarb, L-cyhalothrin, lepimectin, lufenuron, methamidophos, methiocarb, methomyl, methoxyfenozide, milbemycin, nitenpyram, novaluron, profenofos, pymetrozine, rynaxapyr, spinosad, spirodiclofen, spiromesifen, spirotetramate, tebufenozide, tebufenozide, tebufenpyrad, tebufenpyrad, tebupirimphos, teflubenzuron, tefluthrin, thiacloprid, thiamethoxam, thiodicarb, triazophos and triflumuron.

More preferably, the insecticide compound (b) is chosen as being abamectin, acetamiprid, aldicarb, beta-cyfluthrin, carbofuran, chlorpyrifos-E, clothianidin, cypermethrin, cyromazine, deltamethrin, diflubenzuron, emamectin-b., emamectin-b., ethiprole, fipronil, gamma-cyhalothrin, imidacloprid, L-cyhalothrin, lufenuron, methiocarb, methoxyfenozide, pymetrozine, rynaxapyr, spinosad, spirodiclofen, spiromesifen, spirotetramate, tebufenozide, tebufenpyrad, tefluthrin thiacloprid, thiamethoxam, thiodicarb and triflumuron.

Even more preferably, the insecticide compound (b) is selected in the following list L2: abamectin, aldicarb, beta-cyfluthrin, chlorpyrifos-E, clothianidin, cyromazine, deltamethrin, diflubenzuron, emamectin-b., emamectin-b., fipronil, gamma-cyhalothrin, imidacloprid, L-cyhalothrin, methiocarb, pymetrozine, rynaxapyr, spinosad, spirodiclofen, spiromesifen, spirotetramate, tebufenozide, tebufenpyrad, tefluthrin, thiamethoxam and thiodicarb.

The composition according to the present invention comprises a compound of general formula (I) (a) and an insecticide compound (b) in a (a)/(b) weight ratio of from 1/1 to $1/10^{13}$. Preferably, (a)/(b) weight ratio is of from 1/10 to $1/10^{12}$. Even more preferably, (a)/(b) weight ratio is of from $1/10^2$ to $1/10^{11}$. For some applications, as for example when the composition is applied via a seed treatment, the (a)/(b) ratio can be advantageously from $1/10^2$ to $1/10^7$, preferably from $1/10^3$ to $1/10^6$, even more preferably from $1/10^4$ to $1/10^5$. A man of ordinary skill in the art would be able to determine the adequate ratios according to the methods of application and to the compounds.

Non limitative examples of suitable mixtures according to the present invention may include mixtures of a compound selected from the list L1 with an insecticide compound selected in the list L2.

The composition of the present invention may further comprise at least one fungicide active ingredient (c).

Examples of suitable fungicide mixing partners may be selected in the following list:

c 1) a compound capable to inhibit the nucleic acid synthesis like benalaxyl, benalaxyl-M, bupirimate, clozylacon, dimethirimol, ethirimol, furalaxyl, hymexazol, mefenoxam, metalaxyl, metalaxyl-M, ofurace, oxadixyl, oxolinic acid;

c 2) a compound capable to inhibit the mitosis and cell division like benomyl, carbendazim, diethofencarb, ethaboxam, fuberidazole, pencycuron, thiabendazole, thiophanate-methyl, zoxamide;

c 3) a compound capable to inhibit the respiration for example as CI-respiration inhibitor like diflumetorim;

as CII-respiration inhibitor like boscalid, carboxin, fenfuram, flutolanil, furametpyr, furmecyclox, mepronil, oxycarboxin, penthiopyrad, thifluzamide as CIII-respiration inhibitor like amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin c 4) a compound capable of to act as an uncoupler like dinocap, fluazinam, meptyldinocap;

c 5) a compound capable to inhibit ATP production like fentin acetate, fentin chloride, fentin hydroxide, silthiofam;

c 6) a compound capable to inhibit AA and protein biosynthesis like andoprim, blasticidin-S, cyprodinil, kasugamycin, kasugamycin hydrochloride hydrate, mepanipyrim, pyrimethanil;

c 7) a compound capable to inhibit the signal transduction like fenpiclonil, fludioxonil, quinoxyfen;

c 8) a compound capable to inhibit lipid and membrane synthesis like biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl, vinclozolin;

c 9) a compound capable to inhibit ergosterol biosynthesis like aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

c 10) a compound capable to inhibit cell wall synthesis like benthiavalicarb, dimethomorph, flumorph, iprovalicarb, mandipropamid, polyoxins, polyoxorim, validamycin A;

c 11) a compound capable to inhibit melanine biosynthesis like carpropamid, diclocymet, fenoxanil, phthalide, pyroquilon, tricyclazole;

c 12) a compound capable to induce a host defense like acibenzolar-S-methyl, probenazole, tiadinil;

c 13) a compound capable to have a multisite action like Bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxinecopper, propineb, sulphur and sulphur preparations including calcium polysulphide, thiram, tolylfluanid, zineb, ziram;

c 14) a compound selected in the following list: (2E)-2-(2-{[6-(3-chloro-2-methylphenoxy)-5-fluoropyrimidin-4-yl] oxy}phenyl)-2-(methoxyimino)-N-methylacetamide, (2E)-2-{2-[({[(1E)-1-(3-{[(E)-1-fluoro-2-phenylvinyl] oxy}phenyl)ethylidene]amino}oxy)methyl]phenyl}-2-methoxyimino)-N-methylacetamide, 1-(4-chlorophenyl)-2-(1H-1,2,4-triazol-1-yl)cycloheptanol, 1-[(4-methoxyphenoxy)methyl]-2,2-dimethylpropyl-1H-imidazole-1-carboxylate, 1-methyl-N-[2-(1,1,2,2-tetrafluoroethoxy)phenyl]-3-(trifluoromethyl)-1H-pyrazole-4-carboxamide, 2,3,5,6-tetrachloro-4-(methylsulfonyl) pyridine, 2-butoxy-6-iodo-3-propyl-4H-chromen-4-one, 2-chloro-N-(1,1,3-trimethyl-2,3-dihydro-1H-inden-4-yl) nicotinamide, 2-phenylphenol and salts, 3-(difluoromethyl)-1-methyl-N-[2-(1,1,2,2-tetrafluoroethoxy)phenyl]-1H-pyrazole-4-carboxamide, 3-(difluoromethyl)-N-[(9R)-9-isopropyl-1,2,3,4-tetrahydro-1,4-methanonaphthalen-5-yl]-1-methyl-1H-pyrazole-4-carboxamide, 3-(difluoromethyl)-N-[(9S)-9-isopropyl-1,2,3,4-tetrahydro-1,4-methanonaphthalen-5-yl]-1-methyl-1H-pyrazole-4-carboxamide, 3-(difluoromethyl)-N-[4'-(3,3-dimethylbut-1-yn-1-yl)biphenyl-2-yl]-1-methyl-1H-pyrazole-4-carboxamide, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-chloro-7-(4-methylpiperidin-1-yl)-6-(2,4,6-trifluorophenyl)[1,2,4] triazolo[1,5-a]pyrimidine, 8-hydroxyquinoline sulfate, benthiazole, bethoxazin, capsimycin, carvone, chinomethionat, cufraneb, cyflufenamid, cymoxanil, dazomet, debacarb, dichlorophen, diclomezine, dicloran, difenzoquat, difenzoquat methylsulphate, diphenylamine, ecomate, ferimzone, flumetover, fluopicolide, fluoroimide, flusulfamide, fosetyl-aluminium, fosetyl-calcium, fosetyl-sodium, hexachlorobenzene, inumamycin, isotianil, methasulfocarb, methyl (2E)-2-{2-[({cyclopropyl[(4-methoxyphenyl)imino]methyl}thio) methyl]phenyl}-3-methoxyacrylate, methyl 1-(2,2-dimethyl-2,3-dihydro-1H-inden-1-yl)-1H-imidazole-5-carboxylate, methyl isothiocyanate, metrafenone, mildiomycin, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulfonamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl) ethyl]-2-fluoro-4-iodonicotinamide, N-[2-(1,3- dimethylbutyl)phenyl]-5-fluoro-1,3-dimethyl-1H-pyrazole-4-carboxamide, N-{(Z)-[(cyclopropylmethoxy)imino][6-(difluoromethoxy)-2,3-difluorophenyl]methyl}-2-phenylacetamide, N-{2-[1,1'-bi(cyclopropyl)-2-yl]phenyl}-3-(difluoromethyl)-1-methyl-1H-pyrazole-4-carboxamide, N-{2-[3-chloro-5-(trifluoromethyl)pyridin-2-yl]ethyl}-2-(trifluoromethyl)benzamide, natamycin, N-ethyl-N-methyl-N'-{2-methyl-5-(trifluoromethyl)-4-[3-(trimethylsilyl)propoxy]phenyl}imidoformamide, N-ethyl-N-methyl-N'-{2-methyl-5-(difluoromethyl)-4-[3-(trimethylsilyl)propoxy]phenyl}imidoformamide, nickel dimethyldithiocarbamate, nitrothal-isopropyl, O-{1-[(4-methoxyphenoxy)methyl]-2,2-dimethylpropyl}1H-imidazole-1-carbothioate, octhilinone, oxamocarb, oxyfenthiin, pentachlorophenol and salts, phosphorous acid and its salts, piperalin, propamocarb fosetylate, propanosine-sodium, proquinazid, pyribencarb, pyrrolnitrine, quintozene, S-allyl-5-amino-2-isopropyl-4-(2-methylphenyl)-3-oxo-2,3-dihydro-1H-pyrazole-1-carbothioate, tecloftalam, tecnazene, triazoxide, trichlamide, valiphenal, zarilamid.

Preferably, the fungicide compound (c) is selected in the following list
N-[2-(1,3-dimethylbutyl)phenyl]-5-fluoro-1,3-dimethyl-1H-pyrazole-4-carboxamide, benalaxyl, ethirimol, hymexazol, mefenoxam, metalaxyl, metalaxyl-M, benomyl, carbendazim, fuberidazole, pencycuron, thiabendazole, zoxamide, boscalid, carboxin, flutolanil, furametpyr, penthiopyrad, thifluzamide, azoxystrobin, cyazofamid, dimoxystrobin, famoxadone, fenamidone, fluoxastrobin, metominostrobin, orysastrobin, picoxystrobin, pyraclostrobin, trifloxystrobin, fluazinam, silthiofam, cyprodinil, kasugamycin, mepanipyrim, pyrimethanil, fenpiclonil, fludioxonil, iprodione, procymidone, propamocarb, tolclofos-methyl, bitertanol, cyproconazole, difenoconazole, diniconazole, epoxiconazole, etaconazole, fenhexamid, fluquinconazole, flutriafol, hexaconazole, imazalil, imibenconazole, ipconazole, metconazole, prochloraz, prothioconazole, simeconazole, spiroxamine, tebuconazole, tetraconazole, triadimefon, triadimenol, triflumizole, triticonazole, carpropamid, tolylfluanid, fluopicolide, isotianil, N-{2-[1,1'-bi(cyclopropyl)-2-yl]phenyl}-3-(difluoromethyl)-, 1-methyl-1H-pyrazole-4-carboxamide, propamocarb fosetylate, triazoxide, N-(3',4'-dichloro-5-fluorobiphenyl-2-yl)-3-(difluoromethyl)-1-methyl-1H-pyrazole-4-carboxamide, N-{2-[3-chloro-5-(trifluoromethyl)pyridin-2-yl]ethyl}-2-(trifluoromethyl)benzamide.

More preferably, the fungicide compound (c) is selected in the following list L3:
N-[2-(1,3-dimethylbutyl)phenyl]-5-fluoro-1,3-dimethyl-1H-pyrazole-4-carboxamide, metalaxyl, carbendazim, pencycuron, fenamidone, fluoxastrobin, trifloxystrobin, pyrimethanil, iprodione, bitertanol, fluquinconazole, ipconazole, prochloraz, prothioconazole, tebuconazole, triadimenol, triticonazole, carpropamid, tolylfluanid, fluopicolide, isotianil, N-{2-[1,1'-bi(cyclopropyl)-2-yl]phenyl}-3-(difluoromethyl)-, 1-methyl-1H-pyrazole-4-carboxamide, propamocarb fosetylate, triazoxide, N-(3',4'-dichloro-5-fluorobiphenyl-2-yl)-3-(difluoromethyl)-1-methyl-1H-pyrazole-4-carboxamide, N-{2-[3-chloro-5-(trifluoromethyl)pyridin-2-yl]ethyl}-2-(trifluoromethyl)benzamide.

Where the third active ingredient (c) as defined above is present in the composition, this compound may be present in an amount of (a)/(b)/(c) weight ratio of from 1/1/1 to 1/10$^{13}$/10$^{14}$, the ratios of compound (b) and compound (c) varying independently from each other. Preferably, the (a)/(b)/(c) weight ratio may be of from 1/10/10 to 1/10$^{12}$/10$^{13}$ even more preferably from 1/100/100 to 1/10$^{11}$/10$^{12}$. When the composition is applied via a seed treatment, the (a)/(b)/(c) weight ratio can be advantageously from 1/100/100 to 1/10$^{7}$/10$^{8}$, more preferably from 1/10$^{3}$/10$^{3}$ to 1/10$^{6}$/10$^{7}$, even more preferably from 1/10$^{4}$/10$^{4}$ to 1/10$^{5}$/10$^{6}$ Non limitative examples of suitable mixtures according to the present invention may include mixtures of a compound selected from the list L1 with an insecticide compound selected in the list L2 and with a fungicide compound selected from the list L3.

The composition according to the present invention may further comprise an other additional component such as an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid.

Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise other additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated, or in furrow in the soil, by means of a suitable device, such as a spraying or dusting device, but also concentrated commercial compositions which must be diluted before they are applied to the crop.

The pesticidal compositions of the present invention can be used to curatively or preventively control insects, but also to increase the yield, growth, or vigor of the plant.

Thus, according to a further aspect of the present invention, there is provided a method for curatively or preventively controlling insects and increasing the yield, growth or vigor of a plant characterised in that a composition as hereinbefore defined is applied via seed treatment, foliar application, stem application or drench/drip application (chemigation) to the seed, the plant and/or to the fruit of the plant, or to soil, particularly in furrow, and/or to inert substrate (e.g. inorganic substrates (e.g. sand, rockwool, glasswool, expanded minerals (e.g. perlite, vermiculite, zeolite, expanded clay)), Pumice, Pyroclastic materials/tuff, synthetic organic substrates (e.g. Polyurethane), organic substrates (e.g. peat, composts, tree waste products (e.g. coir, wood fibre/chips, tree bark)) and/or to a liquid substrate (e.g. floating hydroponic systems, Nutrient Film Technique, Aeroponics) in which the plant is growing or in which it is desired to grow.

The composition as used against pests and diseases of crops comprises an effective and non-phytotoxic amount of an insecticide compound. The expression "effective and non-phytotoxic amount" means an amount of composition according to the invention which is sufficient to control or destroy the pests and diseases present or liable to appear on the crops, and which does not entail any appreciable symptom of phytotoxicity for the said crops. Such an amount can vary within a wide range depending on the pests and diseases to be combated or controlled, the type of crop, the climatic conditions and the compounds included in the composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Plants that can be protected by the method according to the invention can be legumes or non-leguminous plants.

Among the plants that can be protected by the method according to the present invention, mention may be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantins), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

Among the legumes, mention may be made of soybean, pea, horse bean, groundnut, bean, lupin, alfalfa or clover.

The composition according to the present invention is well tolerated by plants, have favourable homeotherm toxicity and are environmentally friendly; it is suitable for protecting plants and plant organs, for increasing harvest yields, for improving the quality of the harvested material and for controlling animal pests, in particular insects, arachnids and nematodes encountered in agriculture, in forests, in gardens and leisure facilities, in the protection of stored products and materials and in the hygiene sector. It is preferably used as crop protection agents. It is active against normally sensitive and resistant species and against all or some stages of development. Among the animal pests that can also be controlled by the method according to the present invention, mention may be made of:

Pest from the order of the Isopoda, for example, *Oniscus asellus, Armadillidium vulgare* and *Porcellio scaber;*

Pest from the order of the Diplopoda, for example, *Blaniulus guttulatus;*

Pest from the order of the Chilopoda, for example, *Geophilus carpophagus* and *Scutigera* spp.;

Pest from the order of the Symphyla, for example, *Scutigerella immaculate;*

Pest from the order of the Thysanura, for example, *Lepisma saccharina.*

Pest from the order of the Collembola, for example, *Onychiurus armatus;*

Pest from the order of the Orthoptera, for example, *Acheta domesticus, Gryllotalpa* spp., *Locusta migratoria migratorioides, Melanoplus* spp. and *Schistocerca gregaria;*

Pest from the order of the Blattaria, for example, *Blatta orientalis, Periplaneta americana, Leucophaea maderae* and *Blattella germanica;*

Pest from the order of the Dermaptera, for example, *Forficula auricularia;*

Pest from the order of the Isoptera, for example, *Reticulitermes* spp.;

Pest from the order of the Phthiraptera, for example, *Pediculus humanus corporis, Haematopinus* spp., *Linognathus* spp., *Trichodectes* spp., *Damalinia* spp.;

Pest from the order of the Thysanoptera, for example, *Hercinothrips femoralis, Thrips tabaci, Thrips palmi, Frankliniella accidentalis;*

Pest from the order of the Heteroptera, for example, *Eurygaster* spp., *Dysdercus intermedius, Piesma quadrata, Cimex lectularius, Rhodnius prolixus* and *Triatoma* spp.;

Pest from the order of the Homoptera, for example, *Aleurodes brassicae, Bemisia tabaci Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium comi, Saissetia oleae, Laodelphax striatellus, Nilaparvata lugens, Aonidiella aurantii, Aspidiotus hederae, Pseudococcus* spp. and *Psylla* spp.;

Pest from the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis*

*flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae;*

Pest from the order of the Coleoptera, for example, *Anobium punctatun, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus;*

Pest from the order of the Hymenoptera, for example, *Diprion* spp., *Hoplocampa* spp., *Lasius* spp., *Monomorium pharaonis* and *Vespa* spp.;

Pest from the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.;

Pest from the order of the Siphonaptera, for example, *Xenopsylla cheopis* and *Ceratophyllus* spp.;

Pest from the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.;

The plant-parasitic nematodes such as *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

The composition according to the present invention may also be used against pests and diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 800 g/ha, preferably between 50 and 300 g/ha for applications in foliar treatment. If a drench/drip/ in furrow application is possible, the dose can be lower, especially in artificial substrates like rockwool or perlite. The dose of active substance applied is generally and advantageously between 0.5 and 200 g per 100 kg of seed, preferably between 1 and 150 g per 100 kg of seed in the case of seed treatment. It is clearly understood that the doses indicated above are given as illustrative examples of the invention. A person skilled in the art will know how to adapt the application doses according to the nature of the crop to be treated.

The composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

II-1. Structure of Compounds (I) According to the Invention

Compounds containing a meta-substituted benzamide group were prepared. It is preferred to keep identical the total number of atoms along the chain (16) and also the unsaturation of cis type in position 9. In practice, for the production of the starting materials, the lipid chain may be linked to the aromatic ring via an oxygen atom.

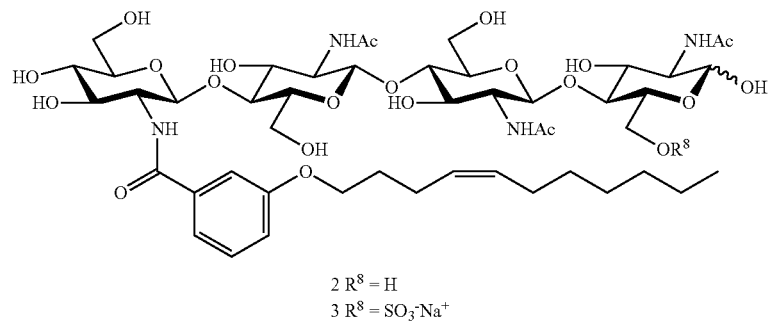

2 R$^8$ = H
3 R$^8$ = SO$_3^-$Na$^+$

An analog 4 containing a meta-substituted benzylamine function, and also an N-acetylated analog 5, which makes it possible to regain the overall charge of the natural product, were also synthesized. These analogs were prepared in the sulfated series.

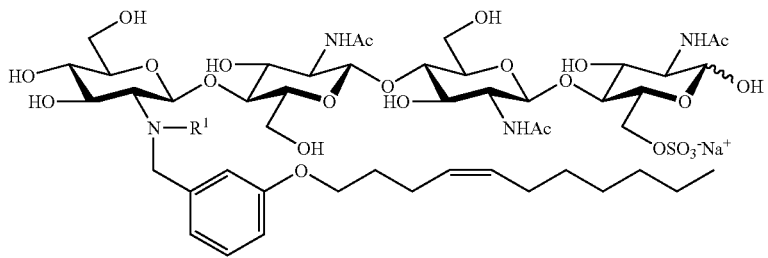

4 R¹ = H
5 R¹ = Ac

Two other sulfated analogs, one containing a fully saturated chain and the other an unsaturated chain of alkyne type, make it possible to study the effect of the unsaturation of Z type in position 9 present on the natural product.

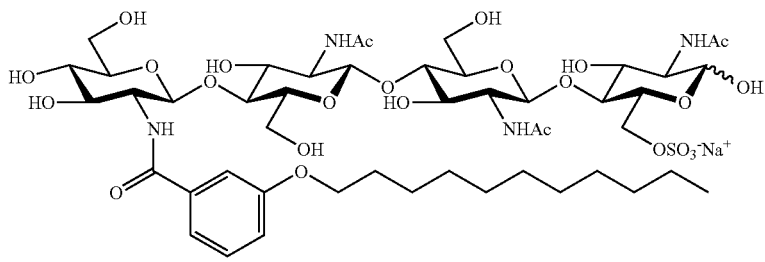

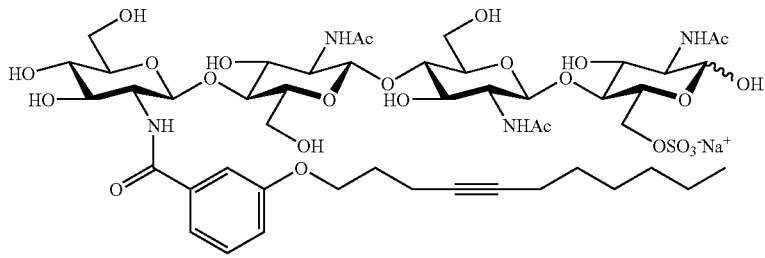

Finally, two sulfated analogs, the substitution on the aromatic ring of which is in the ortho position for one and in the para position for the other, make it possible to study the effect of the unsaturation of trans type located in position 2 on the natural product.

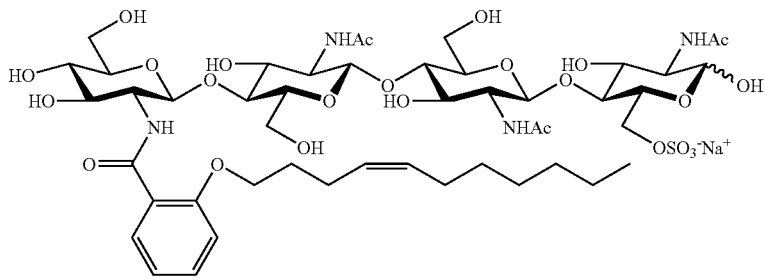

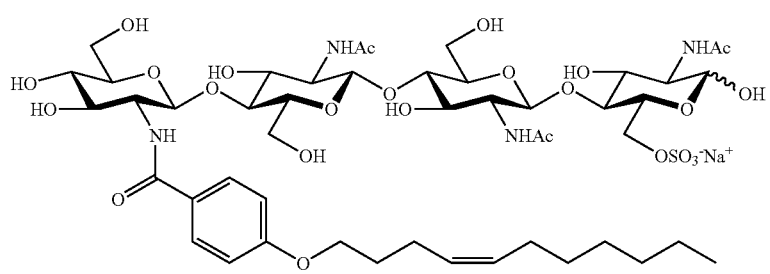

9

Finally, an analog, derived from a fucosyl pentamer, bearing a meta substitution on the chain, was prepared.

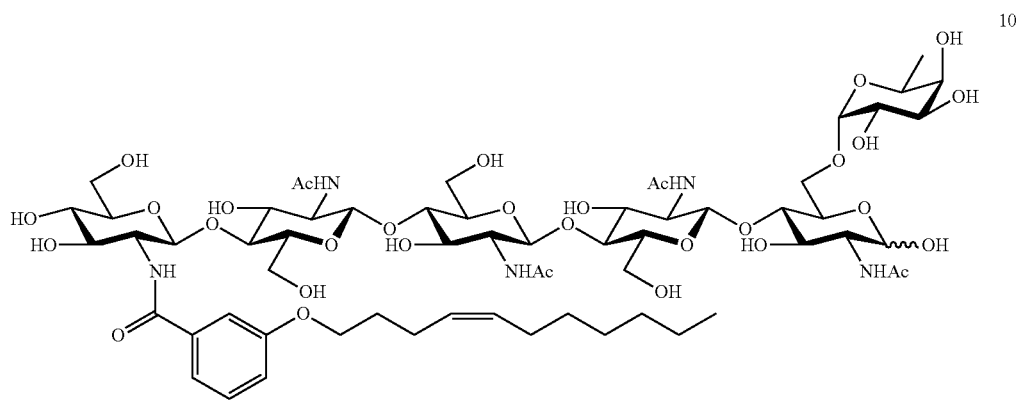

10

The references for the biological tests are the following compounds:

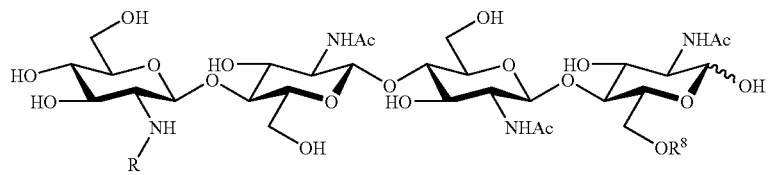

11 $R^8$ = SO$_3$Na  R = C16:1Δ9Z
12 $R^8$ = SO$_3$Na  R = C16:2Δ2E,9Z

III.1 Examples for the Preparation of the Various Oligosaccharidic Backbones

The oligosaccharidic backbones corresponding to formula (I) can be obtained by biotechnological methods, such as for example the use of recombinant bacterial cells, such as for example recombinant *Escherichia coli* cells harboring heterologous gene from *rhizobia*. For example, the introduction of nodBC genes from *Azothizobium caulinodans* into *Escherichia coli* allows the preparation of tetra-N-acetylchitopentaose (Samain E., et al., *Carbohydr. Res.*, 1997, 302, 35-42). The use of nodBC from *Rhizobium meliloti* allows the preparation of tri-N-acetyl chitotetraose. Moreover, the use of additional genes, such as for example nodH (rhizobial sulfotransferase) or nodL (rhizobial O-acetyltransferase) allows the introduction of modifications on specific hydroxyls (Samain E, et al., *J. Biotechnol.*, 1999, 72, 33-47). Other combinations of rhizobial or non rhizobial genes allow the production of various chitooligosaccharidic backbones usable as starting materials in acylation for the production of molecules of formula (I), with different modifications on the hydroxy or amino groups.

The oligosaccharidic backbones can also be obtained by standard chemical synthesis, using methods and strategies which are classical and well identified in carbohydrate chemistry. Description of recent and appropriate procedures can be found in many textbooks and reviews and more precisely in, for example, descriptions given in *Carbohydrates in Chemistry and Biology*, Editors.: B. Ernst, G. W. Hart, P. Sinaÿ, Wiley-VCH, Weinheim; 2000. The manipulation of correctly chosen protecting groups, which can be introduced on very specific positions on hydroxy or amino groups, and sequentially or orthogonally removed to liberate any given group for selective modification, allow the introduction of specific modifications onto the oligosaccharidic backbone, including for example acylation or alkylation or glycosylation of specific hydroxy groups, or acylation and alkylation of specific amino groups.

Protecting groups which can be used to protect amines, and can be removed in sequential or orthogonal conditions, include for example phthalimido, tetrachlorophthalimido, azido, t-butyloxycarbonyl, 2,2,2-trichloroethoxycarbonyl, and trichloroacetyl groups. Protecting groups which can be used to protect alcohols, and can be removed in sequential or orthogonal conditions, include for example acetyl, benzyl, p-methoxybenzyl, trimethylsilyl, triethylsilyl, t-butyldimethylsilyl, and t-butyldiphenylsilyl groups, as well as cyclic acetals such as for example methylidene, ethylidene, isopropylidene, benzylidene, or p-methoxybenzylidene acetals. Classical methods and conditions of protecting group manipulations can be found, for example, in "Protecting Groups", P. J. Kocienski, $2^{nd}$ Edition, Georg Thieme Verlag, Stuttgart, 2000 or in "Protective Groups in Organic Synthesis", T. W. Greene, P. G. M. Wuts, $3^{rd}$ Edition, Wiley, New York, 1999.

The oligosaccharidic backbones can be prepared by the controlled assembly of monosaccharidic building blocks harboring correctly chosen protecting groups on the desired positions. This assembly can be performed according to methods which are classical and standard use in the field of chemical synthesis of oligosaccharides. Sequential removal of protecting groups, followed by chemical modification on the liberated hydroxy or amino groups, should allow the production of the molecules corresponding to formula (I). Examples for the introduction of another sugar represented by a fucose moiety can be easily found in the prior art, including for example A. I. Zinin et al., *Russ. Chem. Bull.*, 1998, 47, 496-501, and J. S. Debenham et al., *J. Org. Chem.*, 1996, 61, 6478-6479. The classical methods of assembly of monosaccharides include for example the activation of anomeric trichloroacetimidate, O-pentenyl, alkylthio, arylthio, sulfoxydo, halo, or phosphato groups. Numerous examples of oligosaccharide syntheses can be found in many reviews, in the series of monographies cited above or in, for example "Glycoscience, Chemistry and Chemical Biology", Editors: B. Fraser-Reid, K. Tatsuta, J. Thiem, Springer-Verkag, Berlin Heidelberg, 2001.

It is envisaged that products of formula (I) can be chemically synthesized according to the exemplary procedure described below (in this Scheme, $P^xH$ on the amino groups can also represent a protecting group such as for example a phthalimido or tetrachlorophthalimido protecting group or $N_2$ if there is an azido group at position 2 of the carbohydrate). $P^1$-$P^{20}$ represent either temporary protecting groups, or permanently introduced modification which are desired in the final backbone, such as for example acylations, alkylations or glycosylations. $X^1$-$X^4$ represent anomeric activatable leaving groups such as for example trichloroacetimidate, O-pentenyl, alkylthio, arylthio, sulfoxydo, halo, or phosphato groups. Two monosaccharides harbouring the correct protecting group pattern can be coupled together in one of the standard glycosylation procedures. A correctly chosen protecting group ($P^6$) can be selectively removed from the desired position of the obtained disaccharide in conditions which will not affect other protecting groups. Coupling of another monosaccharide onto the newly freed position will lead to a trisaccharide. Removal of a correctly chosen protecting group ($P^{10}$) from the obtained trisaccharide in conditions which will not affect other protecting groups can be followed by coupling of another monosaccharide onto the newly freed position, leading to a tetrasaccharide. Removal of a correctly chosen protecting group ($P^{14}$) from the obtained tetrasaccharide in conditions which will not affect other protecting groups can be followed by coupling of another monosaccharide onto the newly freed position, leading to a pentaasaccharide. Removal of any correctly chosen protecting group from a hydroxy or amino group of the obtained pentasaccharide in conditions which will not affect other protecting groups will allow specific chemical modification, such as for example acylation, alkylation, or glycosylation, onto this position. This process can be repeated as many times as needed to introduce all the desired modifications on the backbone. Final deprotection of the remaining protecting groups will allow access to the desired backbone.

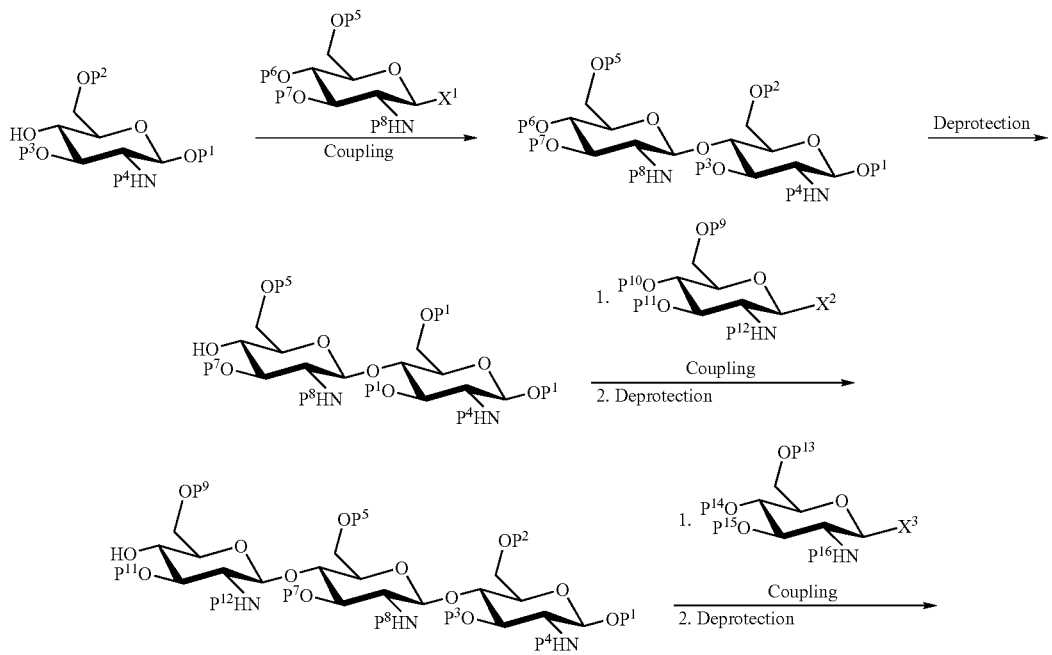

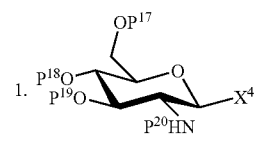
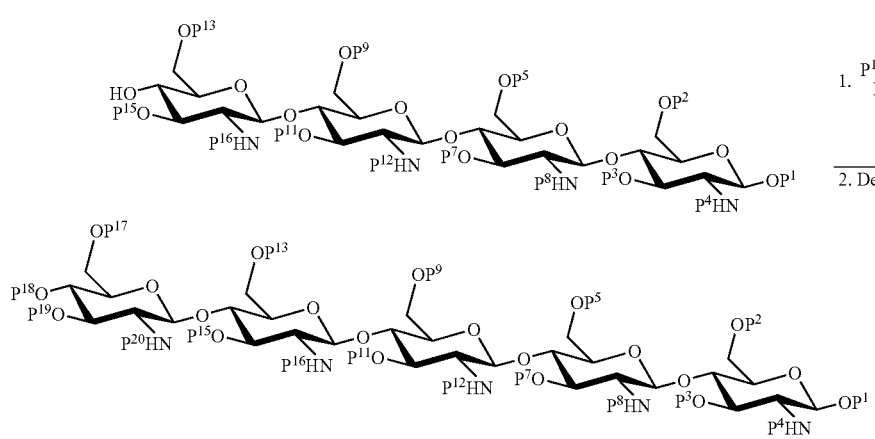

1. Specific deprotection on a given OH or NH$_2$
2. Chemical modification of this position
3. Repeat 1 and 2 on another position
4. ...
5. Final deprotection Examples representative of this strategy can be found in the prior art, including for example K. C. Nicolaou et al., *J. Am. Chem. Soc,* 1992, 114, 8701, It is also envisaged that products of formula (I) can be chemically synthesized according to the alternative exemplary procedure described below (in this Scheme, P$^x$H on the amino groups can also represent a protecting group such as for example a phthalimido or tetrachlorophthalimido protecting group or N$_2$ if there is an azido group at position 2 of the carbohydrate). P$^1$-P$^{16}$ represent either temporary protecting groups, or permanently introduced modification which are desired in the final backbone, such as for example acylations, alkylations or glycosylations. X$^1$-X$^3$ represent anomeric activatable leaving groups such as for example trichloroacetimidate, O-pentenyl, alkylthio, arylthio, sulfoxydo, halo, or phosphato groups. Y$^1$-Y$^4$ represent either protecting groups or other stable groups which can be transformed into activatable leaving groups such as for example trichloroacetimidate, O-pentenyl, alkylthio, arylthio, sulfoxydo, halo, or phosphato groups. Two monosaccharides harbouring the correct protection pattern can be coupled together in a standard glycosylation procedure. Activation of a correctly chosen group (Y$^1$) will allow the introduction of an anomeric activatable group X$^2$ which will allow the coupling of the obtained disaccharide with another monosaccharide. Activation of a correctly chosen group (Y$^2$) will allow the introduction of an anomeric activatable group X$^3$ which will allow the coupling of the obtained trisaccharide with another monosaccharide. Activation of a correctly chosen group (Y$^4$) will allow the introduction of an anomeric activatable group X$^3$ which will allow the coupling of the obtained tetrasaccharide with another monosaccharide, leading to a pentasaccharide. Removal of any correctly chosen protecting group from a hydroxy or amino group of the obtained pentasaccharide in conditions which will not affect other protecting groups will allow specific chemical modification, such as for example acylation, alkylation, or glycosylation, onto this position. This process can be repeated as many times as needed to introduce all the desired modifications on the backbone. Final deprotection of the remaining protecting groups will allow access to the desired backbone.

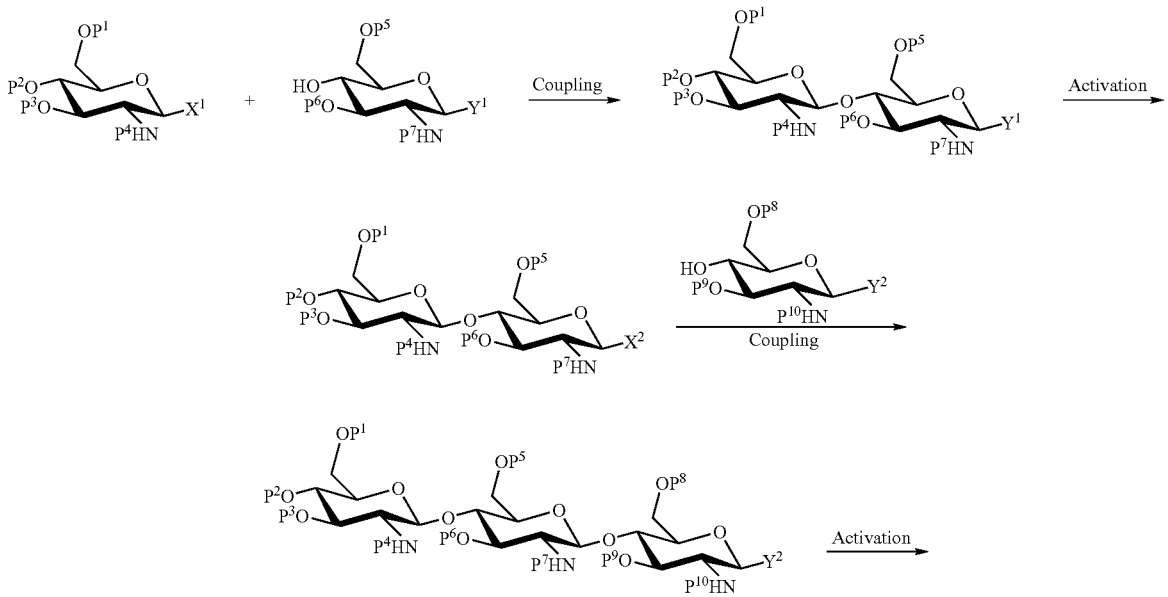

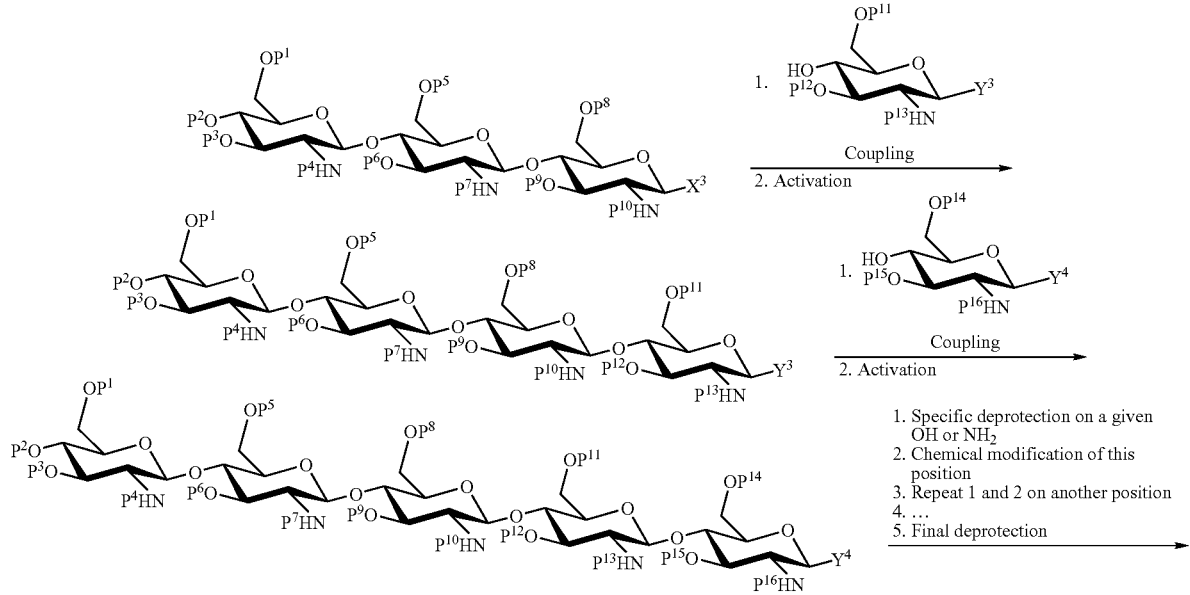

1. Specific deprotection on a given OH or NH$_2$
2. Chemical modification of this position
3. Repeat 1 and 2 on another position
4. ...
5. Final deprotection Examples representative of this strategy can be found in the prior art, including for example D. Tailler et al., *J. Chem. Soc., Chem. Commun.,* 1994, 1827, and J. S. Debenham et al., *J. Org. Chem.,* 1997, 62, 4591-4600.

In addition to the basic two general examples given above, which consist in adding a monosaccharide at each "round" of steps, examples representative of other strategies can also be found in the prior art, such as for example adding, instead of a monosaccharide, a properly prepared disaccharide. This includes the preparation disclosed in, for example, S. Ikeshita et al., *Tetrahedron Lett.,* 1994, 3123, and L. X. Wang et al., *J. Chem. Soc., Perkin Trans. I,* 1994, 621.

III-2. Synthesis of the Various Aromatic Chains

For the benzamide LCOs, the coupling with the amino tetramer is performed with a benzoyl chloride (acylation) and for the benzyl LCOs, with a benzaldehyde (reductive alkylation).

III-2.1. Synthesis of Aromatic Chains Meta-Substituted with the undec-4Z-enyloxy Chain According to the reaction scheme below, the methyl ester 15 is prepared, from which reduction to the aldehyde or saponification to the acid (acyl chloride precursor) may be envisaged.

To do this, 1-iodoundec-4Z-ene 13 is used to alkylate methyl 3-hydroxybenzoate. The ester 15 is isolated in a yield of 76%.

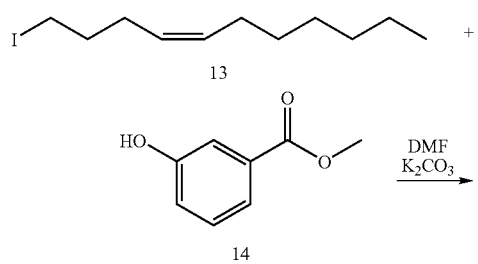

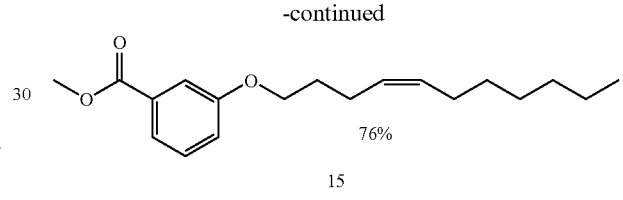

Conversion of the ester to the aldehyde 17 is performed in two steps.

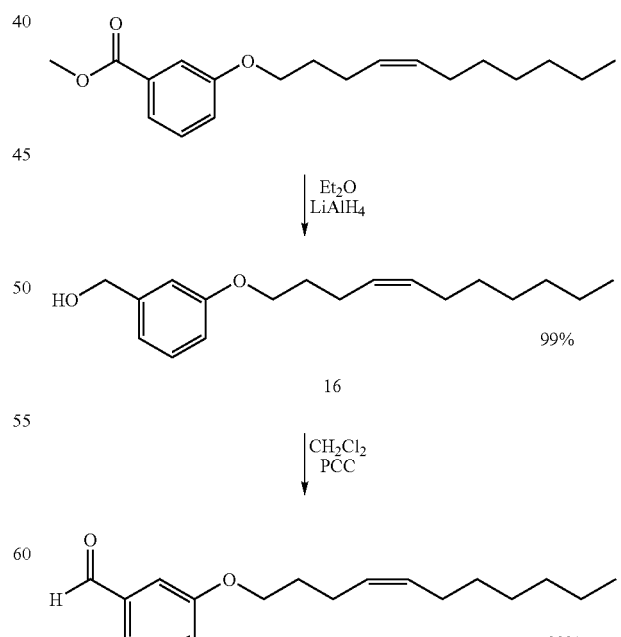

Moreover, the acyl chloride 19 is obtained by saponification of the ester 15 followed by reaction with oxalyl chloride.

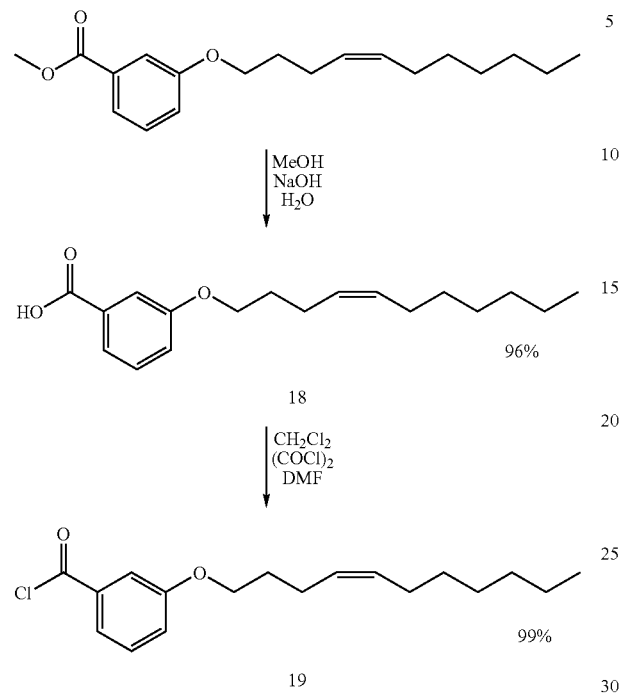

III-2.2. Synthesis of Aromatic Chains Meta-Substituted with Undecanyloxy and Undec-4-ynyloxy Chains The same procedure with 1-bromoundecane or 1-iodoundec-4-yne in anhydrous DMF, followed by saponification and formation of the chloride, lead to the acid chlorides 23 and 27.

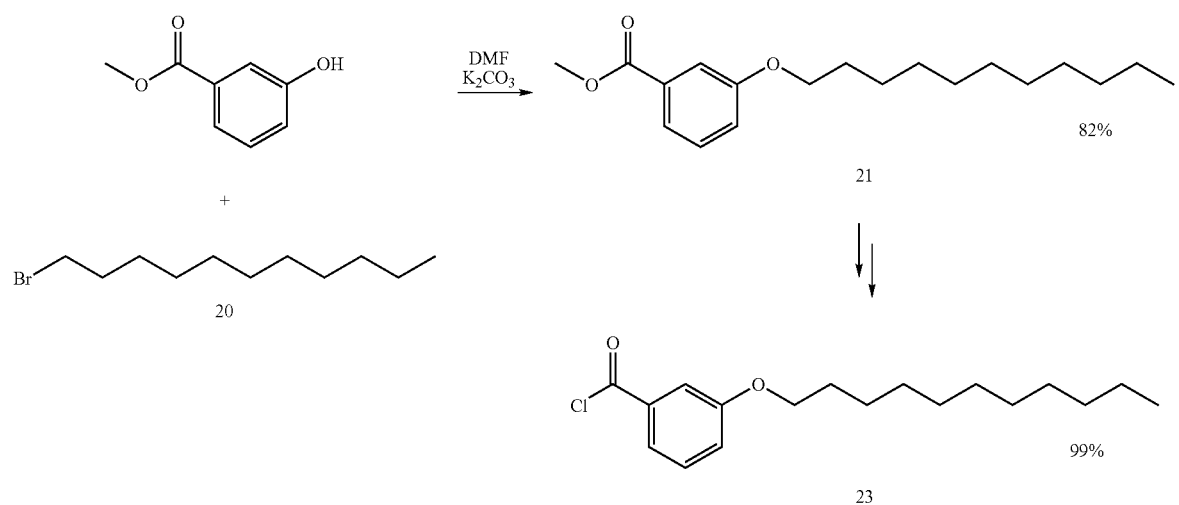

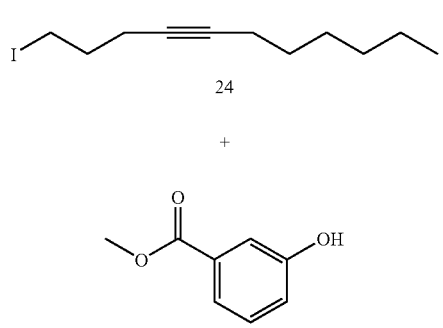
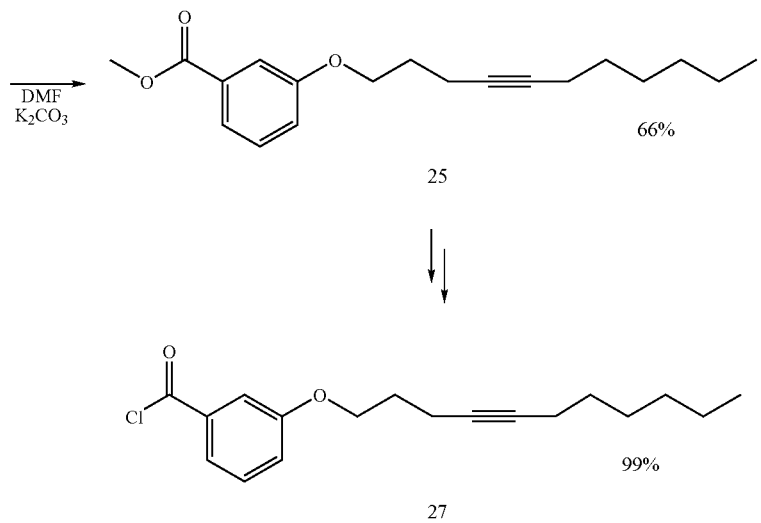
III-2.3. Synthesis of Aromatic Chains Ortho- or Para-Substituted with the Undec-4-Enyloxy Chain
The acid chlorides 31 and 35 are similarly prepared from 29 and 33, which are obtained as previously by Williamson coupling of 1-iodoundec-4Z-ene 13 with methyl 2-hydroxybenzoate 28 (or methyl salicylate) in a yield of 66%, and with methyl 4-hydroxybenzoate 32 in a yield of 79%.
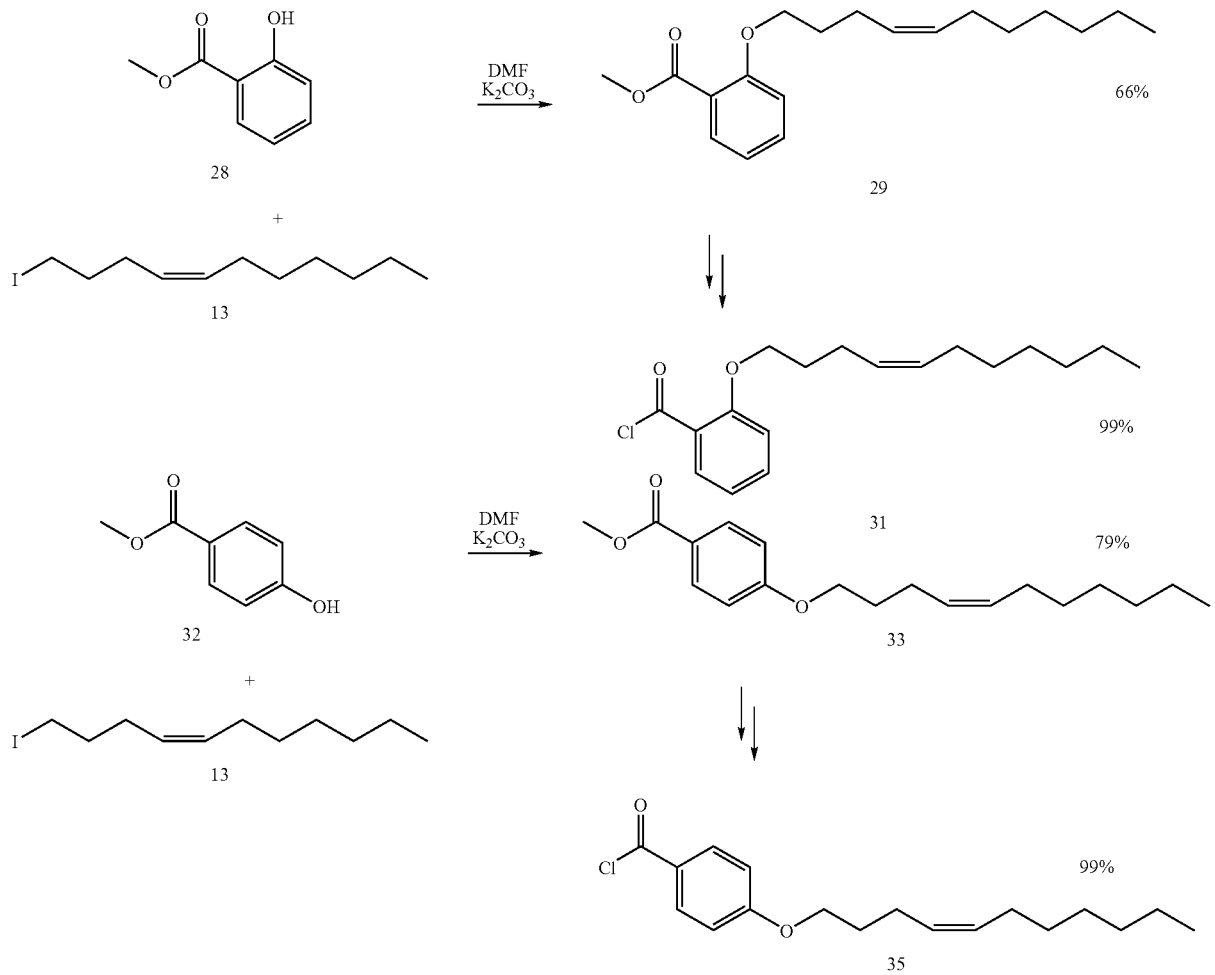

The saponifications and conversions to chloride are quantitative in both cases.

III-3. N-Acylation of the Sulfated Tetramer CO-IV(NH$_2$,S) with the Various Benzoyl Chlorides

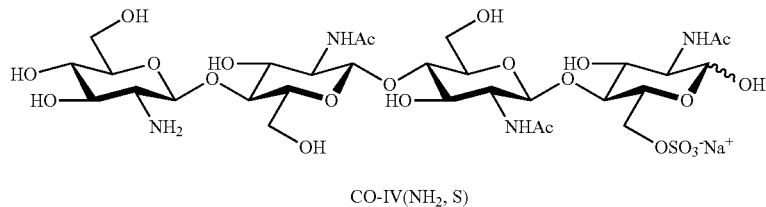

CO-IV(NH$_2$, S)

III-3.1. Coupling with 3-(undec-4Z-enyloxy)benzoyl chloride 19

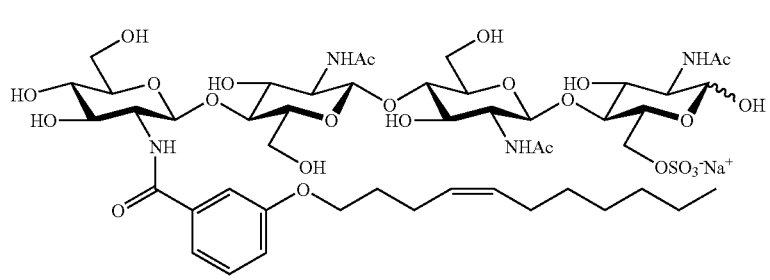

3

The coupling may be performed by dissolving the starting material in a DMF-water mixture in the presence of sodium hydrogen carbonate. Under these conditions, only the free amine is acylated. With 6 equivalents of chloride and after reaction for 18 hours, a conversion of about 60% is achieved, but the reaction is highly selective. 33% of desired product 3 are thus isolated. The purity of the product is checked by HPLC.

The ultraviolet (UV) absorption spectrum of product 3 is substantially different from that of the reference compound 12, especially due to the presence in 3 of an absorption peak at 289 nm. Such a peak, due to the benzamide group, does not exist for compound 12. This perfectly illustrates the UV properties of some of the compounds according to the invention making them easy to assay, in contrast with the natural Nod factors.

In contrast with compound 12, compound 3 also has a characteristic fluorescence at 345 nm when it is excited at 289 nm.

III-3.2. Coupling with 3-(undecanyloxy)benzoyl chloride 23 and 3-(undec-4-ynyloxy)benzoyl chloride 27

The same procedure as for the preceding derivative is repeated, i.e. dissolution in a DMF-water mixture and use of several equivalents of chloride.

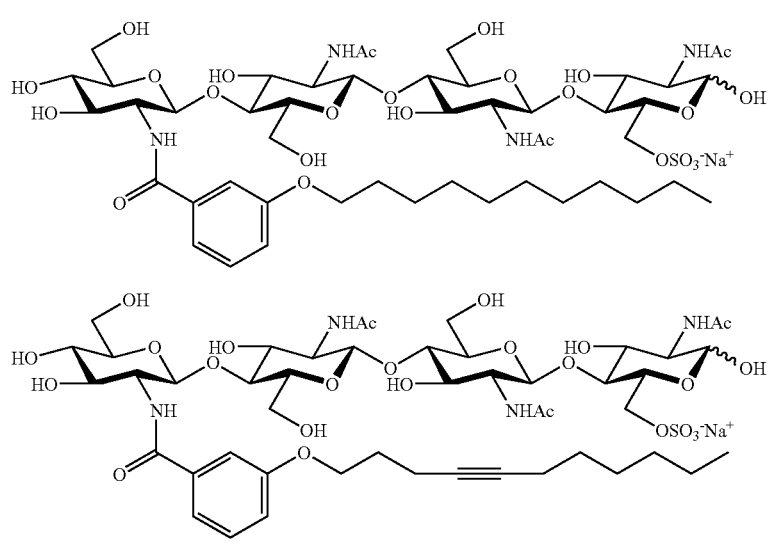

Under these conditions, the saturated analog 6 is obtained in a yield of 32% (and 47% conversion) and the analog containing a triple bond 7 in a yield of 31% (and 70% conversion). The purity is also checked by HPLC.

III-3.3. Coupling with 2-(undec-4Z-enyloxy)benzoyl chloride 31 and 4-(undec-4Z-enyloxy)benzoyl chloride 35

For these two analogs, by adopting a similar protocol, a yield of 48% is obtained for the ortho-substituted derivative 8 and a yield of 40% is obtained for the para-substituted derivative 2. For the two reactions, 4 equivalents of chloride were used. The purity is also checked by HPLC.

The reaction was carried out as previously in a DMF-water mixture, in which the starting material and the chloride are soluble. In order to facilitate the final purification, the reaction is performed in the presence of a basic Dowex resin ($HCO_3^-$).

At the end of the reaction, the reaction medium is diluted with an acetonitrile/water mixture, and the expected compound is purified by filtration of the resin, passing through acidic Dowex ($H^+$), resin, concentration and washing of the solid residue with ethyl acetate and then with water. 22% of the expected product 2 are thus isolated.

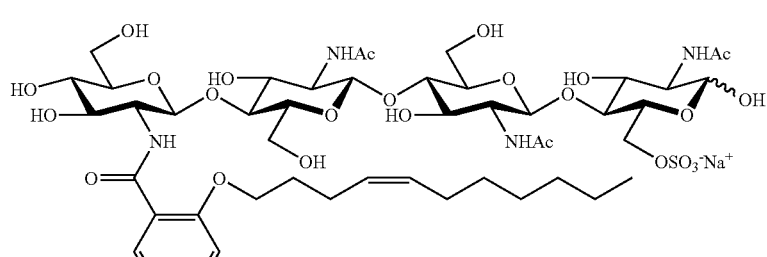

8

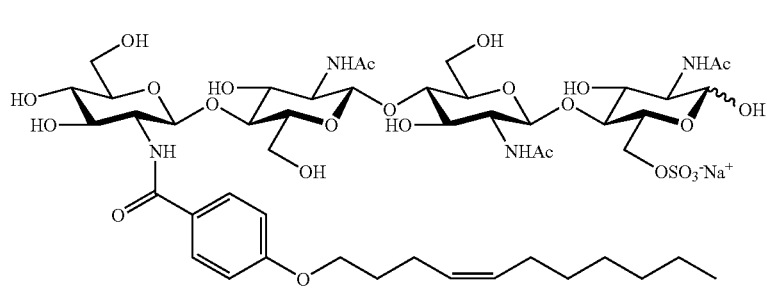

9

III-4. N-Acylation of the Nonsulfated Tetramer CO-IV(NH$_2$) with 3-(undec-4Z-enyloxy)benzoyl chloride 19

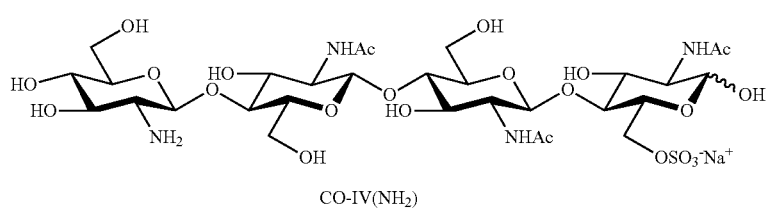

CO-IV(NH$_2$)

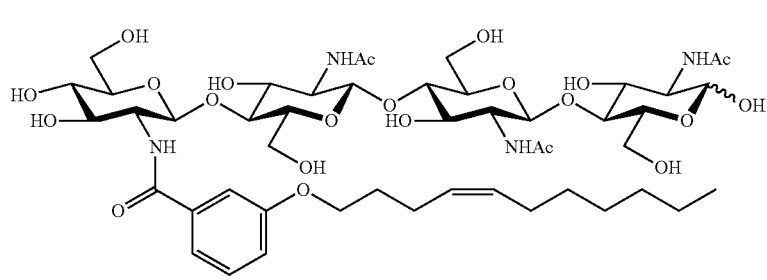

2

III-5. N-Acylation of the Fucosylated Pentamer CO-V(NH$_2$, Fuc) with 3-(undec-4Z-enyloxy)benzoyl chloride 19

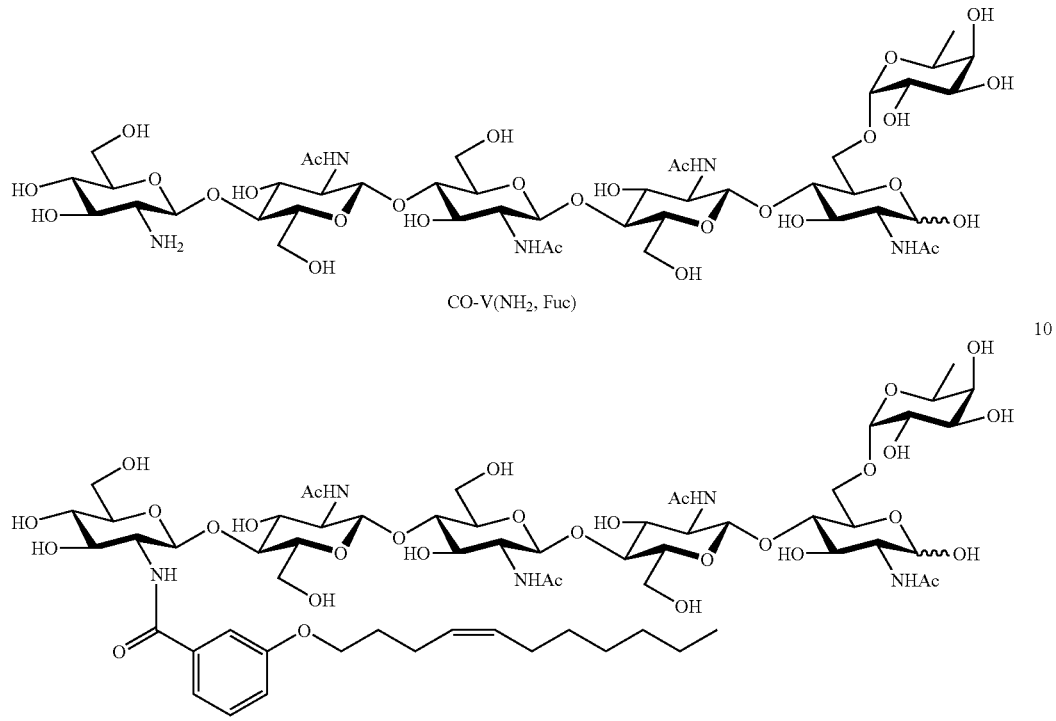

The reaction was performed as for the preceding product, in a DMF-water mixture, in which the starting material and the chloride are soluble. In order to facilitate final purification, the reaction is performed in the presence of a basic Dowex resin (HCO$_3^-$).

At the end of the reaction, the reaction medium is diluted with an acetonitrile/water mixture, and the expected compound is purified by filtration of the resin, passage through acidic Dowex resin (H$^+$), concentration and washing of the solid residue with ethyl acetate and then with water. 28% of the expected product 10 are thus isolated.

III-6. Reductive Alkylation of the Sulfated Tetramer with 3-(undec-4Z-enyloxy)benzaldehyde III-6.1. Alkylation of the Tetramer CO-IV(NH$_2$,S)

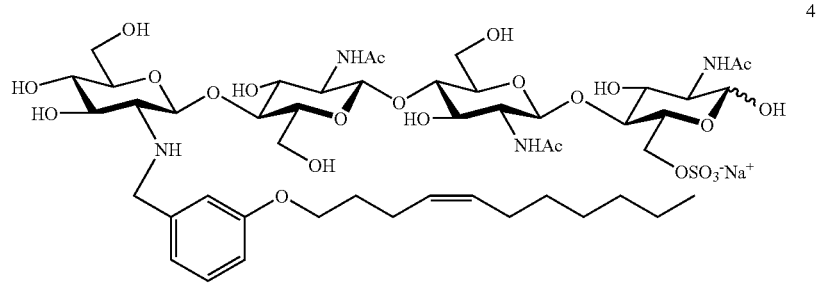

The reductive alkylation reaction was performed in anhydrous DMF in the presence of lithium bromide. With 12 equivalents of aldehyde and 15 equivalents of sodium cyanoborohydride, 71% of expected coupling product 4 are isolated by chromatography on silica gel after 24 hours.

III-6.2. N-Acetylation of the Coupling Product Obtained from the Reductive Alkylation

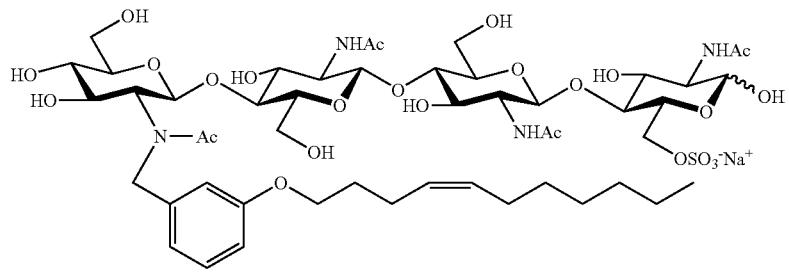

The reaction is performed in an ethyl acetate-methanol-water mixture by addition of acetic anhydride, in the presence of sodium hydrogen carbonate. After 12 hours, the starting material 4 is removed by passage through H$^+$ resin. After purification on silica, the expected product 5 is isolated in a yield of 77%. The purity is checked by HPLC.

IV EXAMPLES OF COMPOUND (I)

For the aromatic derivatives, the ring is numbered according to the official nomenclature. For the description of the NMR spectra for the CO and LCO, the sugars are numbered starting with the reducing end:

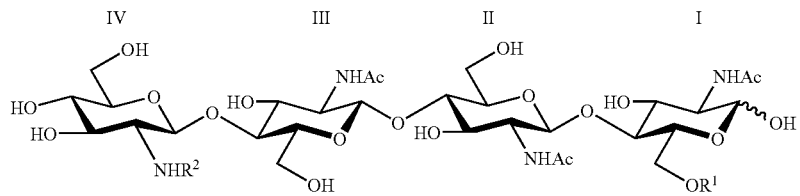

The conventional numbering is adopted on each sugar.

2-acetamido-4-O-{2-acetamido-4-O—[2-acetamido-2-deoxy-4-O-(2-deoxy-2-(N-3-(undec-4Z-enyloxy)benzoyl)amino-β-D-glucopyranosyl)-β-D-glucopyranosyl]-2-deoxy-β-D-glucopyranosyl}-2-deoxy-D-glucopyranose (2)

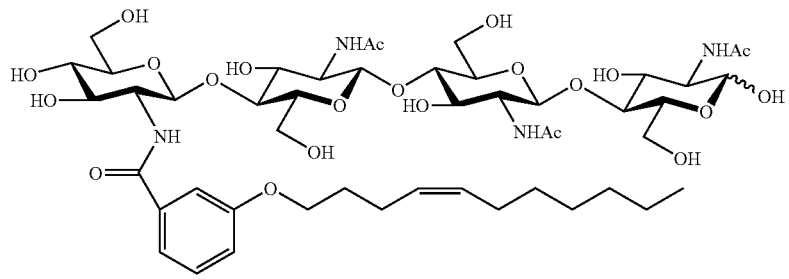

7.2 mg of CO-IV(NH$_2$) are dissolved in 200 μL of water and 500 μL of DMF, and are then heated to 40° C. 36 mg of Dowex 1×2-100 resin (HCO$_3^-$) are then added, followed by addition of 160 μL of a solution of 19 in distilled THF (26 μmol). 108 mg of HCO$_3^-$ resin and 480 μL of the solution of 19 in distilled THF (78 μmol) are added in three portions over 48 hours. The reaction medium is diluted with 3 mL of 1/1 acetonitrile/water mixture, the reaction medium is collected, leaving the resin, and is then filtered through cotton wool to remove the entrained resin beads. The filtrates are passed through a Dowex 50×8-100 resin (H$^+$) and then concentrated, and washing of the solid residue is then performed with ethyl acetate, and then with water. 2 mg of a white powder are obtained, i.e. a yield of 22%.

$^1$H NMR (400 MHz, 20/1 DMSO-d6/D$_2$O) δ (ppm): 7.40-7.31 (m, 3H, ArH-2, ArH-6 and ArH-5), 7.04 (m, 1H, ArH-4), 5.41-5.35 (m, 2H, CH=CH), 4.87 (d, 0.7H, J$_{1,2}$=2.3 Hz, H-1α$^I$), 4.52 (d, 1H, J=8.3 Hz, H-1β$^{IV}$), 4.42 (d, 0.3H, J=8.0 Hz, H$_1$-β$^I$), 4.33 (2d, 2H, J=8.3 Hz, H1β$^{II-III}$), 3.98 (t, 2H, J=6.0 Hz, ArOCH$_2$—CH$_2$). 3.78-3.05 (m, 24H, other sugar Hs), 2.16 (dt, 2H, J=5.8 and J=6.7 Hz, CH$_2$—CH=CH), 1.97 (dt, 2H, J=6.0 and J=6.2 Hz, CH=CH—CH$_2$), 1.81/1.81/1.79 (3s, 9H, 3 COCH$_3$), 1.80-1.72 (m, 2H, ArOCH$_2$—CH$_2$—CH$_2$), 1.28-1.13 (m, 8H, 4 CH$_2$), 0.81 (t, 3H, CH$_3$, J=6.5 Hz).

Mass Spectrum:

Positive electrospray (ESI) ionization m/z=1183.5 [M+Na]+

2-acetamido-4-O-{2-acetamido-4-O—[2-acetamido-
2-deoxy-4-O-(2-deoxy-2-(N-3-(undec-4Z-enyloxy)
benzoyl)amino-β-D-glucopyranosyl)-β-D-glucopy-
ranosyl]-2-deoxy-β-D-glucopyranosyl}-2-deoxy-6-
O-sulfo-D-glucopyranose, sodium salt (3

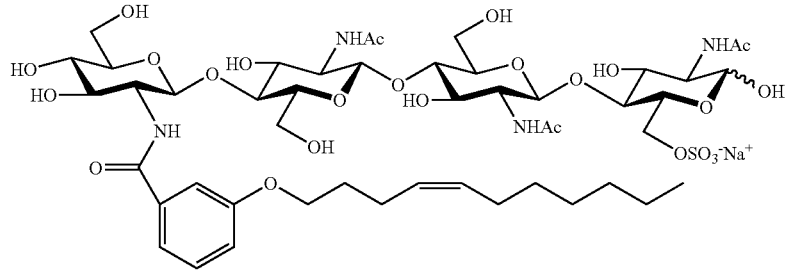

15 mg of CO-IV(NH$_2$,S) (17 μmol) are dissolved in 100 μL of water and 250 μL of DMF. 3 mg of sodium hydrogen carbonate (34 μmol) are then added, followed by addition of 20 μL of a solution of 19 in THF at a concentration of 0.25 g/mL (16.4 μmol). The reaction medium is heated to 60° C. and 100 μL of the solution of 48 and 10 mg of sodium hydrogen carbonate are added in six portions over 18 hours. After concentrating, the residue is purified by placing it in dichloromethane(DCM)/methanol (5/1) on a column of silica, while diluting it greatly, in order to remove the lipid chain. The elution is then performed with E/M/W (7/2/1 Ethyl acetate/Methanol/Water). 6.5 mg of a white solid are thus isolated, i.e. a yield of 33%.

$^1$H NMR (400 MHz, DMSO-CD$_3$OD (1/2)) δ (ppm): 7.48 and 7.41 (m, 2 H, ArH-2 and ArH-6), 7.36 (dd, 1 H, ArH-5, $J_{5,6}$ 7.7 Hz and $J_{5,4}$ 8.1 Hz), 7.07 (ddd, 1 H, ArH-4, $J_{4,2} \approx J_{4,6}$ 1.4 Hz), 5.41 (m, 2H, CH=CH), 5.03 (d, 0.8 H, H-1α$^I$, $J_{1*a*,2}$ 3.2 Hz), 4.68-4.59-4.50 (3 d, 3 H, H-1β$^{II,III,IV}$, $J_{1β,2}$ 8.4 Hz, 8.5 Hz and 8.7 Hz), 4.56 (d, 0.2 H, H-1β$^I$, $J_{1β,2}$ 7.7 Hz), 4.25-3.30 (m, 26 H, CH$_2$—OAr, other Hs of the sugars), 2.25 (td, 2H, CH$_2$—CH=CH—CH$_2$, J 6.7 Hz and J 6.2 Hz), 2.10-1.90 (m, 11 H, CH$_2$—CH=CH—CH$_2$ and 3 CH$_3$CO), 1.83 (tt, 2 H, ArO-CH$_2$—CH$_2$—CH$_2$, J 6.7 Hz), 1.35-1.20 (m, 8 H, 4 CH$_2$), 0.88 (m, 3 H, CH$_3$)

Mass Spectrum:
Negative ESI m/z=1139.4 [M−Na]−
UV: 289 nm
Fluorescence: $\lambda_{ex}$: 289 nm; $\lambda_{em}$: 345 nm 2-acetamido-4-O-{2-acetamido-4-O—[2-acetamido-
2-deoxy-4-O-(2-deoxy-2-(N-3-(undec-4Z-enyloxy)
benzyl)amino-D-glucopyranosyl)-β-D-glucopyrano-
syl]-2-deoxy-β-D-glucopyranosyl}-2-deoxy-6-O-
sulfo-D-glucopyranose, sodium salt (4)

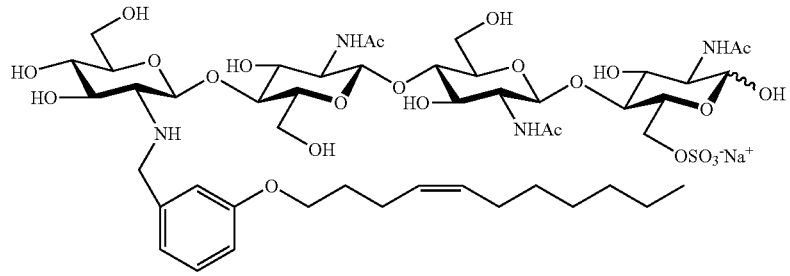

11 mg of CO-IV(NH$_2$,S) (12 μmol) are dissolved in 0.5 mL of DMF to which are added 12 mg of lithium bromide. 2 mg of sodium cyanoborohydride (32 μmol) and 100 μL of a solution of 17 in THF at a concentration of 73 mg/mL (26 μmol) are added. The reaction medium is heated at 40° C. for 4 hours. Every 2 hours, 2 equivalents of aldehyde and 2.5 equivalents of sodium cyanoborohydride are added, i.e. in total 12 equivalents of aldehyde and 15 equivalents of sodium cyanoborohydride. Although the conversion is not complete, the reaction is stopped by destroying the excess sodium cyanoborohydride with 0.5 N hydrochloric acid. When the evolution of gas has ended, the medium is diluted in water and freeze-dried. The resulting material is taken up in water, 5 mg of sodium hydrogen carbonate (59 μmol) are added to return to basic pH, and the resulting material is then coevaporated twice with methanol. The residual white solid is placed in DCM/methanol (5/1) on a column of silica, while diluting it greatly, in order to remove the lipid chain. The elution is then performed with E/M/W (5/2/1) and then (4/1/1). 10 mg of white needles are thus isolated, i.e. a yield of 71%.

$^1$H NMR (400 MHz, DMSO-CD$_3$OD (2/1)) δ (ppm): 7.31 (dd, 1 H, ArH-5, $J_{4,5}$ 8.2 Hz and $J_{5,6}$ 7.8 Hz), 7.02 (m, 2 H, ArH-2 and ArH-6), 6.90 (dd, 1 H, ArH-4, $J_{4,6}$ 2.3 Hz), 5.51 (m, 2 H, CH=CH), 5.08 (d, 0.8H, H-1α$^I$, $J_{1α,2}$ 3.1 Hz), 4.67 (m, 2.2 H, H-1β$^{I,II,III}$), 4.47 (d, 1H, H-1β$^{IV}$, $J_{1β,2}$ 8.0 Hz), 4.06 (t, 2H, CH$_2$-OAr, J 6.3 Hz), 3.94 (s, 2H, NH—CH$_2$—Ar), 4.25-

3.45 (m, 23 H, other Hs of the sugars), 2.45 (dd, 1 H, $\underline{H}_2^{IV}$, $J_{1\beta.2} \approx J_{23}$ 8.8 Hz), 2.31-2.12 (2 m, 4 H, $C\underline{H}_2$—CH=CH—$C\underline{H}_2$), 2.07-2.04-2.01 (3 s, 9H, 3 $C\underline{H}_3$CO), 1.89 (tt, 2 H, ArO—$CH_2$—$C\underline{H}_2$—$CH_2$—CH=CH, J 6.9 Hz), 1.45-1.25 (m, 8 H, 4 $C\underline{H}_2$), 0.97 (t, 3 H, $C\underline{H}_3$, J 6.8 Hz)

$^{13}$C NMR (50 MHz, DMSO-CD$_3$OD (2/1)) δ (ppm): 172 (3 CH$_3$$\underline{C}$O), 160 (Ar$\underline{C}$-3), 132-131-130 (Ar$\underline{C}$-1, Ar$\underline{C}$-5, $\underline{C}$H=$\underline{C}$H), 122 (Ar$\underline{C}$-6), 115 (Ar$\underline{C}$-2, Ar$\underline{C}$-4), 105 ($\underline{C}$-1β$^{II,III,IV}$), 98 ($\underline{C}$-1β$^I$), 92 ($\underline{C}$-1α$^I$), 82-53 (21 C of the sugars and Ar—$\underline{C}$H$_2$—NH), 68 ($\underline{C}$H$_2$—OAr), 33-23 (10 $\underline{C}$H$_2$ and 3 $\underline{C}$H$_3$CO), 14 ($\underline{C}$H$_3$)

Mass Spectrum:
Negative ESI m/z=1125.4 [M−Na]−

2-acetamido-4-O-{2-acetamido-4-O—[2-acetamido-2-deoxy-4-O-(2-deoxy-2-(N-3-undec-4Z-enyloxy)benzyl)acetamido-β-D-glucopyranosyl)-β-D-glucopyranosyl]-2-deoxy-β-D-glucopyranosyl}-2-deoxy-6-O-sulfo-D-glucopyranose, sodium salt (5)

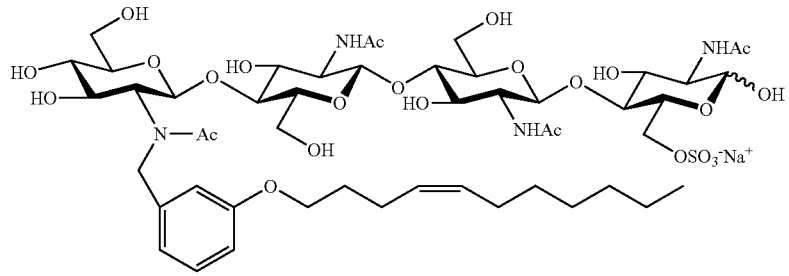

20 mg of sodium hydrogen carbonate and 15 μL of acetic anhydride are added to a solution of 13 mg of 4 (11 μmol) in 0.3 mL of E/M/W (1/1/1). The reaction medium is stirred at room temperature for 12 hours. After concentrating, the residual oil is taken up in E/M/W (1/1/1) and Dowex 50×8-100H+ resin is added. The mixture is filtered and Amberlite IR120 Na+ resin is added to the filtrate. After filtering and concentrating, the product is purified by chromatography in E/M/W (4/1/1). 10 mg of a white solid are thus isolated, i.e. a yield of 77%.

$^1$H NMR (400 MHz, DMSO-CD$_3$OD (2/1)) δ (ppm): 7.25-7.18 (2 t, 1 H, Ar$\underline{H}$-5, $J_{54}$ 7.8 Hz and $J_{5.6}$ 7.9 Hz), 7.10-6.85 (m, 2 H, Ar$\underline{H}$-2 and Ar$\underline{H}$-6), 6.82-6.75 (2 d, 1 H, Ar$\underline{H}$-4), 5.40 (m, 2 H, $C\underline{H}$=$C\underline{H}$), 5.06 (d, 0.6 H, $\underline{H}$-1α$^I$, $J_{1α.2}$ 3.4 Hz), 4.75-4.35 (m, 3.4 H, $\underline{H}$-1β$^{I,II,III,IV}$), 4.30-4.05 (m, 2 H, $\underline{H}$-6a,b$^I$), 4.00-3.30 (m, 25 H, other Hs of the sugars and $C\underline{H}_2$—OAr), 3.80 (s, 2 H, NAc—$C\underline{H}_2$—Ar), 2.90 (m, 1 H, $\underline{H}$-2$^{IV}$), 2.23-2.03 (2 m, 4 H, $C\underline{H}_2$—CH=CH—$C\underline{H}_2$), 1.99-1.90 (m, 12 H, $C\underline{H}_3$CO), 1.80 (tt, 2 H, ArO-CH$_2$—$C\underline{H}_2$—CH$_2$—CH=CH, J 6.9 Hz), 1.35-1.20 (m, 8 H, 4 $C\underline{H}_2$), 0.87 (m, 3 H, $C\underline{H}_3$)

$^{13}$C NMR (50 MHz, DMSO-CD$_3$OD (2/1)) δ (ppm): 176 (CH$_3$$\underline{C}$ON), 174-173-173 (3 CH$_3$$\underline{C}$O), 161 (Ar$\underline{C}$-3), 141 (Ar$\underline{C}$-1), 132-130-129-127 (Ar$\underline{C}$-2, Ar$\underline{C}$-4, Ar$\underline{C}$-5, Ar$\underline{C}$-6, $\underline{C}$H=$\underline{C}$H), 103 (3 $\underline{C}$-1β$^{I,II,IV}$), 100 ($\underline{C}$-1β$^I$), 92 ($\underline{C}$-1α$^I$), 82-50 (24 C of the sugars, Ar—$\underline{C}$H$_2$—NH and $C\underline{H}_2$—OAr), 33-23 (10 $\underline{C}$H$_2$ and 3 $\underline{C}$H$_3$CO), 14 ($\underline{C}$H$_3$)

Mass spectrum: Negative ESI m/z=1067.4 [M−Na]−

2-acetamido-4-O-{2-acetamido-4-O—[2-acetamido-2-deoxy-4-O-(2-deoxy-2-(N-3-(undecanyloxy)benzoyl)amino-β-D-glucopyranosyl)-2-deoxy-β-D-glucopyranosyl]-β-D-glucopyranosyl}-2-deoxy-6-O-sulfo-D-glucopyranose, sodium salt (6)

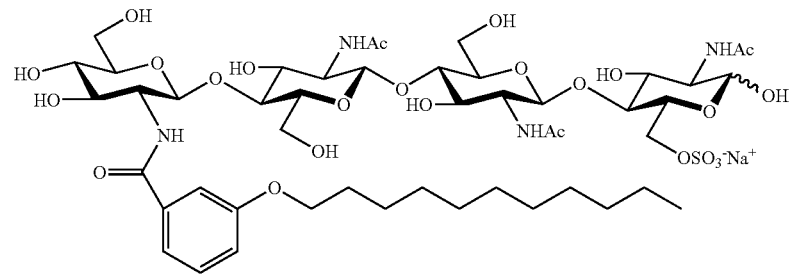

15 mg of $\underline{CO}$-IV(NH$_2$,S) (17 μmol) are dissolved in 100 μL of water and 250 μL of DMF. 6 mg of sodium hydrogen carbonate (71 μmol) and then 25 μL of a solution of 23 in THF at a concentration of 210 mg/mL (17 μmol) are then added. The reaction medium is heated to 60° C. and 200 μL of the solution of chloride and 16 mg of sodium hydrogen carbonate are added in eight portions over 24 hours. After concentrating, the residue is purified by placing it in DCM/methanol (5/1) on a column of silica, while diluting it greatly, in order to remove the lipid chain. The elution is then performed with E/M/W (4/1/1). 6.3 mg of a white solid are thus isolated, i.e. a yield of 32%.

$^1$H NMR (400 MHz, DMSO-CD$_3$OD (1/3)) δ (ppm): 7.44 (m, 2 H, Ar$\underline{H}$-2 and Ar$\underline{H}$-6), 7.39 (dd, 1 H, Ar$\underline{H}$-5, $J_{5.4} \approx J_{5.6}$ 7.9

Hz), 7.10 (ddd, 1 H, ArH-4, J$_{4.6}$≈J$_{4.2}$ 2.1 Hz), 5.05 (d, 0.7H, H-1α$^I$, J$_{1α.2}$ 3.0 Hz), 4.70-4.40 (m, 3.3 H, H-1β$^{I,II,III,IV}$), 4.22 (m, 1 H, H-6a$^I$), 4.10-3.20 (m, 24 H, CH$_2$—OAr and other Hs of the sugar), 2.03-1.99-1.96 (3 s, 9 H, CH$_3$CO), 1.80 (m, 2 H, ArO-CH$_2$—CH$_2$—CH$_2$), 1.35-1.25 (m, 8 H, 4 CH$_2$), 0.92 (t, 3 H, CH$_3$, J 6.5 Hz)

Mass spectrum: Negative ESI m/z=1141.5 [M−Na]−

2-acetamido-4-O-(2-acetamido-4-O—[2-acetamido-2-deoxy-4-O-(2-deoxy-2-(N-3-(undec-4Z-ynyloxy)benzoyl)amino-β-D-glucopyranosyl)-β-D-glucopyranosyl]-2-deoxy-β-D-glucopyranosyl)-2-deoxy-6-O-sulfo-D-glucopyranose, sodium salt (7)

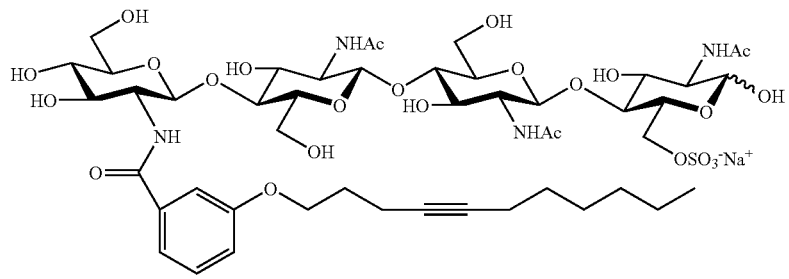

14 mg of CO-IV(NH$_2$,S) (16 μmol) are dissolved in 100 μL of water and 250 μL of DMF. 5 mg of sodium hydrogen carbonate (60 μmol) and then 25 μL of a solution of 27 in THF at a concentration of 190 mg/mL (16 μmol) are then added. The reaction medium is heated to 60° C. and 200 μL of the solution of chloride and 16 mg of sodium hydrogen carbonate are added in eight portions over 24 hours. After concentrating, the residue is purified by placing it in DCM/methanol (5/1) on a column of silica, while diluting it greatly, in order to remove the lipid chain. The elution is then performed with E/M/W (4/1/1). 5.7 mg of expected product are thus isolated in the form of a white solid, i.e. a yield of 31%.

$^1$H NMR (400 MHz, DMSO-CD$_3$OD (1/2)) δ (ppm): 7.43 (m, 2 H, ArH-2 and ArH-6), 7.37 (dd, 1 H, ArH-5, J$_{5.4}$ 8.1 Hz and J$_{5.6}$ 8.0 Hz), 7.10 (ddd, 1 H, ArH-4, J$_{4.2}$≈J$_{4.6}$ 2.0 Hz), 5.04 (d, 0.7 H, H-1α$^I$, J$_{1α.2}$ 3.3 Hz), 4.65-4.59 (2 d, 2 H, H-1β$^{II,III}$, J$_{1β.2}$ 8.4 Hz and J$_{1β.2}$ 8.5 Hz), 4.54 (d, 0.3 H, H-1β$^I$, J$_{1β.2}$ 7.9 Hz), 4.49 (d, 1 H, H-1β$^{IV}$, J$_{1β.2}$ 8.7 Hz), 4.23 (dd, 1 H, H-6a$^I$, J$_{6a.6b}$ 11.1 Hz and J$_{6a.5}$ 3.7 Hz), 4.12 (t, 2 H, CH$_2$-OAr, J 6.2

Hz), 4.10-3.40 (m, 21 H, other Hs of the sugars), 2.35-2.13 (2 m, 4 H, CH$_2$—C≡C—CH$_2$), 2.02-1.98-1.96 (3 s, 9 H, 3 CH$_3$CO), 1.92 (m, 2 H, ArO-CH$_2$—CH$_2$—CH$_2$), 1.45-1.25 (m, 8 H, 4 CH$_2$), 0.88 (t, 3 H, CH$_3$, J 6.7 Hz)

$^{13}$C NMR (62.5 MHz, DMSO-CD$_3$OD (1/2)) δ (ppm): 173 (3 CH$_3$CO), 170 (NCOAr), 158 (ArC-3), 137 (ArC-1), 131 (ArC-5), 121 (ArC-6), 119 (ArC-4), 115 (ArC-2), 103 (C-1β$^{II,III,IV}$), 96 (C-1β$^I$), 92 (C-1α$^I$), 82-50 (20 C of the sugars, C≡C and CH$_2$—OAr), 33-16 (7 CH$_2$ and 3 CH$_3$CO), 15 (CH$_3$)

Mass Spectrum:

Negative ESI m/z=1137.1 [M−Na]−

2-acetamido-4-O-{2-acetamido-4-O—[2-acetamido-2-deoxy-4-O-(2-deoxy-2-(N-2-(undec-4Z-enyloxy)benzoyl)amino-β-D-glucopyranosyl)-β-D-glucopyranosyl]-2-deoxy-β-D-glucopyranosyl}-2-deoxy-6-O-sulfo-D-glucopyranose, sodium salt (8)

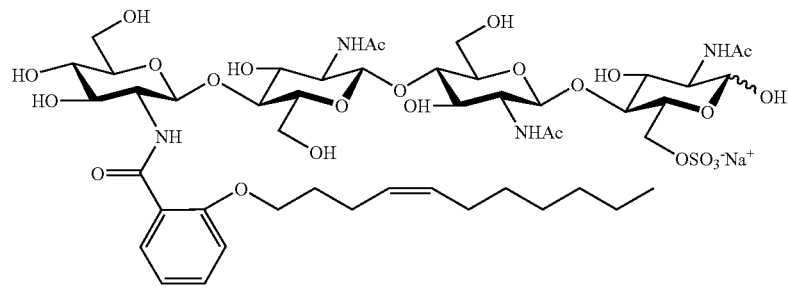

10 mg of CO-IV(NH$_2$,S) (11 μmol) are dissolved in 100 μL of water and 250 μL of DMF. 2 mg of sodium hydrogen carbonate (24 μmol) and then 15 μL of a solution of 31 in THF at a concentration of 115 mg/mL (6 μmol) are then added. The reaction medium is heated to 60° C. and 105 μL of the solution of chloride and 6 mg of sodium hydrogen carbonate are added in seven portions over 18 hours. After concentrating, the residue is purified by placing it in DCM/methanol (5/1) on a column of silica, while diluting it greatly, in order to remove the lipid chain. The elution is then performed with E/M/W (9/2/1). 6.2 mg of a white solid are thus isolated, i.e. a yield of 48% (but a conversion of only 50%).

$^1$H NMR (400 MHz, DMSO-CD$_3$OD (1/2)) δ (ppm): 7.99 (dd, 1 H, ArH-6, J$_{6.5}$ 7.5 Hz and J$_{6.4}$ 1.8 Hz), 7.55 (ddd, 1 H, ArH-4, J$_{4.3}$ 8.3 Hz and J$_{4.5}$ 7.8 Hz), 7.20 (d, 1 H, ArH-3), 7.10 (dd, 1H, ArH-5), 5.52 (m, 2 H, CH=CH), 5.06 (d, 0.7 H, H-1α$^I$, J$_{1α,2}$ 3.0 Hz), 4.70-4.60-4.53 (4 d superimposed, 3.6 H, H-1β$^{I,II,III,IV}$), 4.20-3.40 (m, 25H, other Hs of the sugars and CH$_2$—OAr), 2.33-2.11 (2 m, 4 H, CH—CH=CH—CH$_2$), 2.03-2.01-2.00 (3 s, 9 H, 3 CH$_3$CO), 2.05 (m, 2 H, ArO-CH$_2$—CH$_2$—CH$_2$), 1.50-1.20 (m, 8 H, 4 CH$_2$), 0.94 (t, 3 H, CH$_3$, J 6.8 Hz)

$^{13}$C NMR (62.5 MHz, DMSO-CD$_3$OD (1/2)) δ (ppm): 172 (3 CH$_3$CO), 171 (NCOAr), 158 (ArC-1), 133 (ArC-4, CH=CH), 129 (ArC-6), 122 (ArC-5), 114 (ArC-3), 103 (C-1β$^{II,III,IV}$), 96 (C-1β$^I$), 92 (C-1α$^I$), 82-50 (all the other Cs of the sugars and CH$_2$OAr), 33-24 (7 CH$_2$ and 3 CH$_3$CO), 15 (CH$_3$)

Mass Spectrum:
Negative ESI m/z=1139.5 [M−Na]−

2-acetamido-4-O-{2-acetamido-4-O—[2-acetamido-2-deoxy-4-O-(2-deoxy-2-(4N-4-(undec-4Z-enyloxy)benzoyl)amino-β-D-glucopyranosyl)-β-D-glucopyranosyl]-2-deoxy-β-D-glucopyranosyl}-2-deoxy-6-O-sulfo-D-glucopyranose, sodium salt (9)

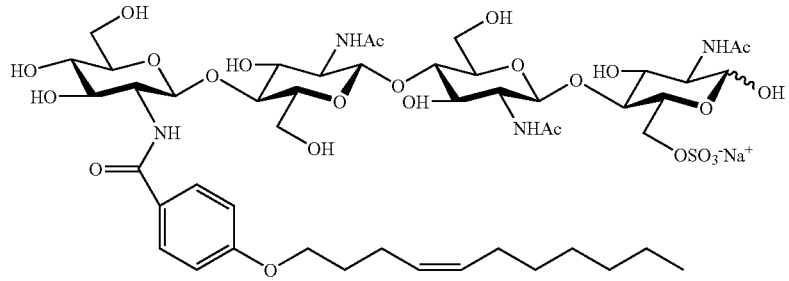

10 mg of CO-IV(NH$_2$,S) (11 μmol) are dissolved in 100 μL of water and 250 μL of DMF. 2 mg of sodium hydrogen carbonate (24 μmol) and then 15 μL of a solution of 35 in THF at a concentration of 115 mg/mL (6 μmol) are then added. The reaction medium is heated to 60° C. and 105 μL of the solution of chloride and 6 mg of sodium hydrogen carbonate are added in seven portions over 17 hours. After concentrating, the residue is purified by placing it in DCM/methanol (5/1) on a column of silica, while diluting it greatly, in order to remove the lipid chain. The elution is then performed with E/M/W (91211). 5.2 mg of a white solid are thus isolated, i.e. a yield of 40% (but a conversion of only 60%).

$^1$H NMR (400 MHz, DMSO-CD$_3$OD (1/2)) δ (ppm): 7.89 (d, 2 H, ArH-2 and ArH-6, J$_{2,3}$≈J$_{6,5}$ 8.8 Hz), 7.04 (d, 2 H, Ar H-3 and ArH-5), 5.48 (m, 2H, CH=CH), 5.05 (d, 0.6 H, H-1α$^I$, J$_{1α,2}$ 3.1 Hz), 4.69-4.55-4.50 (4 d superimposed, 3.6 H, H-1β$^{I,II,III,IV}$), 4.30-3.40 (m, 23 H, other Hs of the sugars), 4.10 (t, CH$_2$—OAr, J 6.3 Hz), 2.28-2.09 (2 m, 4 H, CH$_2$—CH=CH—CH$_2$), 2.02-1.99-1.97 (3 s, 9 H, 3 CH$_3$CO), 1.89 (m, 2 H, ArO-CH$_2$—CH$_2$—CH$_2$), 1.45-1.25 (m, 8 H, 4 CH$_2$), 0.93 (t, 3 H, CH$_3$, J 7.0 Hz)

$^{13}$C NMR (62.5 MHz, DMSO-CD$_3$OD (1/2)) δ (ppm): 172 (3 CH$_3$CO), 169 (NCOAr), 163 (ArC-1), 132-130-129 (ArC-2, ArC-6, CH=CH), 115 (ArC-3, ArC-5), 103 (C-1β$^{II,III,IV}$), 97 (C-1β$^I$), 92 (C-1α$^I$), 83-50 (all the other Cs of the sugars and CH$_2$OAr), 33-23 (7 CH$_2$ and 3 CH$_3$CO), 15 (CH$_3$)

Mass Spectrum:
Negative ESI m/z=1139.5 [M−Na]−

2-acetamido-4-O—[2-acetamido-4-O-{2-acetamido-4-O—[2-acetamido-2-deoxy-4-O-(2-deoxy-2-(N-3-(undec-4Z-enyloxy)benzoyl)amino-β-D-glucopyranosyl)-β-D-glucopyranosyl]-2-deoxy-β-D-glucopyranosyl}-2-deoxy-β-D-glucopyranosyl]-2-deoxy-6-O-(-α-L-fucopyranosyl)-D-glucopyranose (10)

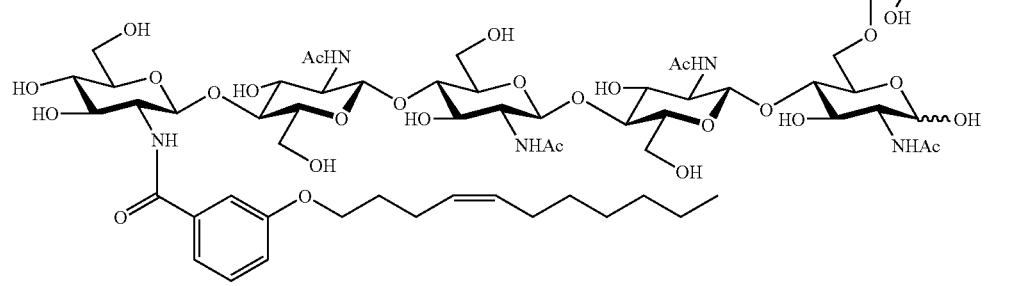

The fucosyl pentamer CO-V(NH$_2$,Fuc) (7.3 mg, 6.4 mmol) is dissolved in H$_2$O (140 µL), followed by addition of DMF (350 µL) and the mixture is brought to 30° C. Dowex 1×2-100 resin (HCO$_3^-$) is then added, followed by addition of a solution (THF, 110 µL) of the acid chloride 19 (6 mg). The reaction mixture is stirred for 24 hours, during which time three further additions of resin and of acid chloride solution are made. The reaction medium is then diluted in H$_2$O/CH$_3$CN (1/1, 2 mL), heated to 56° C., and the supernatant is then filtered through cotton wool. The resin beads and the walls of the flask are extracted several times at 56° C. with H$_2$O/CH$_3$CN (4/1, 7/3, 3/2, 1/1, 2/3, 3/7 and 1/4, 2 mL each). The various fractions are passed through a Dowex 50×8-100 resin (H$^+$), and then pooled and concentrated. The residue is successively washed with EtOAc (3×1 mL) and then H$_2$O (3×1 mL), and then redissolved in H$_2$O/CH$_3$CN (1/1, 10 mL) by heating to 56° C., and then by sonication. The solution is then freeze-dried, and the expected product is obtained in the form of a white powder (2.5 mg, 28%).

The starting material retained on the acid resin is then eluted (2.3 mg, 31%) using aqueous ammonia solution (H$_2$O, 2%).

$^1$H NMR (400 MHz, DMSO-d6/D$_2$O 20/1) δ (ppm): 7.43-7.30 (m, 3 H, ArH-2, ArH-6 and ArH-5); 7.05 (m, 1 H, Ar H-4); 5.45-5.32 (m, 2 H, CH=CH); 4.84 (d, 0.8H, J$_{1,2}$=1.9 Hz, H-1α$^I$); 4.66 (d, 0.8H, J$_{1,2}$<1.0 Hz, H-1Fuc-GlcNAcα), 4.65 (d, 0.2H, J$_{1,2}$<1.0 Hz, H-1Fuc-GlcNAcβ), 4.52 (d, H, J 8.5 Hz, H-1β$^{IV}$), 4.45/4.35/4.33 (4d, 4H, J=8.5 Hz, H-1β$^{II-IV}$), 4.42 (d, 0.2H, J=7.0 Hz, H-1β$^I$); 3.99 (t, 2H, J=6.1 Hz, ArOCH$_2$—CH$_2$), 3.88 (dt, 1H, H-5Fuc), 3.78-3.05 (m, 33H, other sugar Hs), 2.17 (dt, 2H, J=6.0 and J=6.8 Hz, CH$_4$—CH=CH), 1.99 (dt, 2H, J=5.9 and J=6.2 Hz, CH=CH—CH$_2$), 1.82/1.81/1.81/1.79 (4s, 12H, 4 COCH$_3$), 1.80-1.72 (m, 2 H, ArOCH$_2$—CH$_2$), 1.31-1.15 (m, 8H, 4 CH$_2$), 1.08 (d, 0.6H, J$_{5,6}$=6.9 Hz, H-6Fuc-GlcNAcβ), 1.05 (d, 2.4H, J$_{5,6}$=6.5 Hz, H-6Fuc-GlcNAcα), 0.82 (t, 3 H, CH$_3$, J=6.5 Hz).

methyl 3-(undec-4Z-enyloxy)benzoate (15)

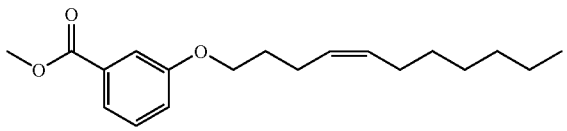 [SMILES: CCCCCC/C=C\CCCOc1cccc(C(=O)OC)c1]

850 mg of 14 (6.15 mmol) and 900 mg of K$_2$CO$_3$ (6.51 mmol) are added to 1.7 g of 13 (6.07 mmol) in anhydrous DMF (20 mL). After reaction for 4 hours at 90° C., the reaction medium is concentrated, taken up in DCM and then washed with water. 1.87 g of a yellow oil are obtained, and are chromatographed, on silica gel in pentane/ethyl acetate (50/1). 1.37 g of a yellow oil are isolated, i.e. a yield of 76%.

$^1$H NMR (250 MHz, CDCl$_3$) δ (ppm): 7.60 (ddd, 1 H, Ar H-6, J$_{6,5}$ 8.0 Hz and J$_{6,4}$≈J$_{6,2}$ 0.5 Hz), 7.52 (dd, 1 H, ArH-2, J$_{2,4}$ 3.0 Hz), 7.31 (dd, 1 H, ArH-5, J$_{5,4}$ 8.0 Hz), 7.07 (ddd, 1 H, ArH-4), 5.38 (m, 2 H, CH=CH), 3.98 (t, 2 H, CH$_2$-OAr, J 6.3 Hz), 3.89 (s, 3 H, OCH$_3$), 2.22-1.99 (2 m, 4 H, CH$_2$—CH=CH—CH$_2$), 1.83 (tt, 2H, ArO-CH$_2$—CH$_2$—CH$_2$—CH=CH, J 6.8 Hz), 1.55-1.20 (m, 8 H, 4 CH$_2$), 0.84 (t, 3H, CH$_3$, J=7.5 Hz)

$^{13}$C NMR (62.5 MHz, CDCl$_3$) δ (ppm): 131-129-128 (C-5, CH=CH), 122 (C-6), 120 (C-4), 115 (C-2), 66 (CH$_2$—OAr), 52 (CH$_3$O), 32-22 (7 CH$_2$), 14 (CH$_3$)

Mass Spectrum:
Positive ESI m/z=327.2 [M+Na]+
High res. Calc. for C$_{19}$H$_{28}$O$_3$Na: 327.193614, Found: 327.193200
Elemental Analysis:

|   | Calc. | Found |
|---|---|---|
| C | 74.96 | 74.68 |
| H | 9.27 | 9.37 |
| O | 15.77 | 15.79 |

Infrared (cm$^{-1}$): 2970-2950-2927-2858-1726-1586-1446-1288-1228-756

3-(undec-4Z-enyloxy)benzyl alcohol (16)

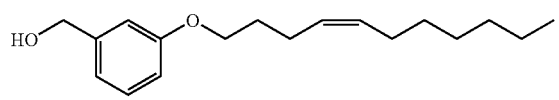

35 mg of lithium aluminum hydride (922 µmol) are added, at 0° C., to 140 mg of 15 (460 µmol) in ether (3 mL). After reaction for 1 hour 30 minutes, the reaction medium is diluted with ether and hydrolyzed with two drops of water. After filtering through Celite, drying over Na$_2$SO$_4$ and concentrating, 127 mg of a colorless oil are isolated, i.e. a yield of 99%.

$^1$H NMR (250 MHz, CDCl$_3$) δ (ppm): 7.18 (dd, 1 H, Ar H-5, J$_{5,6}$ 8.0 Hz and J$_{5,4}$ 8.3 Hz), 6.84 (m, 2 H, ArH-2 and Ar H-4), 6.75 (dd, 1 H, ArH-4, J$_{4,2}$ 2.9 Hz), 5.32 (m, 2 H, CH=CH), 4.58 (s, 2 H, CH$_2$OH), 3.89 (t, 2H, CH$_2$-OAr, J 6.3 Hz), 2.16-1.95 (2 m, 4 H, CH$_2$—CH=CH—CH$_2$), 1.76 (tt, 2 H, ArO-CH$_2$—CH$_2$—CH$_2$—CH=CH, J 6.8 Hz), 1.45-1.18 (m, 8 H, 4 CH$_2$), 0.84 (t, 3 H, CH$_3$, J=6.3 Hz)

$^{13}$C NMR (62.5 MHz, CDCl$_3$) δ (ppm): 159 (C-3), 142 (C-1), 131-130-128 (C-5, CH=CH), 119 (C-6), 114 (C-4), 113 (C$_2$), 67 (CH$_2$—OAr), 65 (CH$_2$OH), 32-23 (7 CH$_2$), 14 (CH$_3$)

Mass Spectrum:
Positive ESI m/z=299.2 [M+Na]+
High res. Calc. for C$_{18}$H$_{28}$O$_2$Na: 299.198700, Found: 299.199250
Infrared (cm$^{-1}$): 3329, 3005, 2940, 2925, 2855, 1669, 1602, 1452, 1264

3-(undec-4Z-enyloxy)benzaldehyde (17)

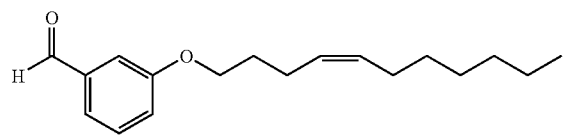 [SMILES: CCCCCC/C=C\CCCOc1cccc(C=O)c1]

10 mL of anhydrous DCM and then 190 mg of PCC (881 µmol) are added under argon to 120 mg of alcohol 16 (434 µmol) dried by coevaporation with toluene. The reaction is heated to the reflux point of the DCM for 1 hour. After cooling, the reaction medium is diluted with ether and filtered through Florisil. After concentrating, 118 mg of a yellow oil are obtained, i.e. a yield of 99%.

¹H NMR (250 MHz, CDCl₃) δ (ppm): 9.95 (s, 1 H, CHO), 7.42 (m, 2 H, ArH-6 and ArH-5), 7.36 (d, 1 H, ArH-2, J₂,₄ 2.9 Hz), 7.15 (m, 1 H, ArH-4), 5.39 (m, 2 H, CH=CH), 3.99 (t, 2H, CH₂-OAr, J 6.3 Hz), 2.21-1.99 (2 m, 4H, CH₂—CH=CH—CH₂), 1.84 (ft, 2 H, ArO-CH₂—CH₂—CH₂—CH=CH, J 6.8 Hz), 1.40-1.15 (m, 8H, 4 CH₂), 0.84 (t, 3 H, CH₃, J 6.6 Hz)

¹³C NMR (62.5 MHz, CDCl₃) δ (ppm): 192 (CHO), 160 (C-3), 138 (C-1), 131-130-128 (C-5, CH=CH), 123 (C-6), 122 (C-4), 113 (C-2), 67 (CH₂—OAr), 52 (CH₃O), 32-23 (7 CH₂), 14 (CH₃)

Mass Spectrum:

Chemical ionization (CI) 1% solution in DCM

A fine desorption peak

M+1=275

Infrared (cm⁻¹): 3005-2940-2927-2855-2723-1700-1599-1452-1263-787

3-(undec-4Z-enyloxy)benzoic acid (18)

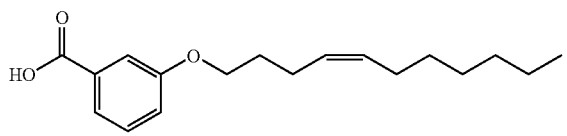 [SMILES: CCCCCC/C=C\CCCOc1cccc(C(=O)O)c1]

4 mL of 1 N sodium hydroxide solution (4.0 mmol) are added portionwise to 1.14 g of 15 (3.74 mmol) in methanol (30 mL). The solution is refluxed overnight. A further 4 mL of 1 N sodium hydroxide solution are added, and the mixture is refluxed for a further 1 hour 30 minutes. After evaporating off the solvent, the reaction medium is acidified with 0.5 N HCl and extracted with DCM. 1.04 g of a yellow oil are obtained, i.e. a yield of 96%.

¹H NMR (200 MHz, CDCl₃) δ (ppm): 10.00-9.00 (bd, 1 H, CO₂H), 7.69 (d, 1 H, ArH-6, J₆,₅ 7.8 Hz), 7.60 (d, 1 H, ArH-2, J₂,₄ 2.4 Hz), 7.35 (dd, 1 H, ArH-5, J₅,₄ 8.3 Hz), 7.14 (dd, 1 H, ArH-4), 5.40 (m, 2 H, CH=CH), 4.00 (t, 2 H, CH₂—OAr, J 6.3 Hz), 2.21-2.00 (2 m, 4 H, CH₂—CH=CH—CH₂), 1.85 (tt, 2H, ArO-CH₂—CH₂—CH₂—CH=CH, J 6.8 Hz), 1.35-1.05 (m, 8 H, 4 CH₂), 0.85 (t, 3 H, CH₃, J 6.5 Hz)

¹³C NMR (50 MHz, CDCl₃) δ (ppm): 172 (CO₂H), 159 (C-3), 131-130-130-128 (C-1, C-5, CH=CH), 121-122 (C-4, C-6), 115 (C-2), 67 (CH₂—OAr), 32-23 (7 CH₂), 14 (CH₃)

Mass Spectrum:

Negative ESI m/z=289.1 [M-H]-

High res. Calc. for C₁₈H₂₅O₃: 289.180370, Found: 289.180730

Elemental Analysis:

|   | Calc. | Found |
|---|-------|-------|
| C | 74.45 | 74.29 |
| H | 9.02  | 9.01  |

Infrared (cm⁻¹): 2970-2950-2925-2854-1695-1585-1286-757

3-(undec-4Z-enyloxy)benzoyl chloride (19)

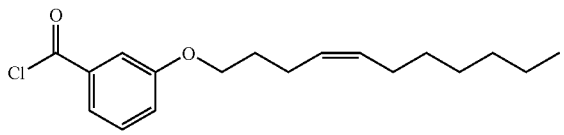 [SMILES: CCCCCC/C=C\CCCOc1cccc(C(=O)Cl)c1]

1 mL of oxalyl chloride (11.5 mmol) and two drops of anhydrous DMF are added under argon to 100 mg of toluene-dried 18 (345 µmol) dissolved in 20 mL of anhydrous DCM. The medium is stirred at room temperature for two hours, and then concentrated to give 106 mg of the expected chloride in the form of a yellow oil, i.e. a yield of 99%.

¹H NMR (250 MHz, CDCl₃) δ (ppm): 7.71 (ddd, 1 H, ArH-6, J₆,₅ 8.3 Hz, J₆,₄ 2.4 Hz and J₆,₂ 0.9 Hz), 7.57 (dd, 1 H, ArH-2, J₂,₄ 1.6 Hz), 7.39 (dd, 1 H, ArH-5, J₅,₄ 8.3 Hz), 7.20 (ddd, 1 H, ArH-4), 5.40 (m, 2 H, CH=CH), 3.99 (t, 2 H, CH₂—OAr, J 6.3 Hz), 2.23-2.00 (2 m, 4 H, CH₂—CH=CH—CH₂), 1.85 (tt, 2 H, ArO-CH₂—CH₂—CH₂—CH=CH, J 7.0 Hz), 1.28-1.15 (m, 8 H, 4 CH₂), 0.85 (t, 3 H, CH₃, J 6.5 Hz)

methyl 3-undecyloxy)benzoate (21)

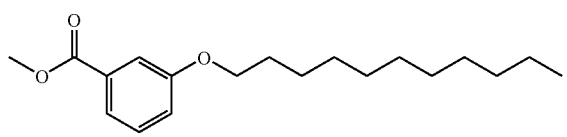 [SMILES: CCCCCCCCCCCOc1cccc(C(=O)OC)c1]

350 mg of 14 (2.30 mmol) and 330 mg of K₂CO₃ (2.39 mmol) are added to 554 mg of 1-bromoundecane (2.35 mmol) in anhydrous DMF (7 mL). After reaction for 16 hours at 90° C., the reaction medium is concentrated, taken up in DCM and then washed with water. 607 mg of a yellow oil are obtained, and are chromatographed on silica gel in pentane/ethyl acetate (60/1). 579 mg of expected coupling product are isolated in the form of a yellow oil, i.e. a yield of 82%.

¹H NMR (200 MHz, CDCl₃) δ (ppm): 7.62 (m, 1 H, ArH-6), 7.55 (m, 1 H, ArH-2), 7.34 (dd, 1 H, ArH-5, J₅,₄ 8.1 Hz and J₅,₆ 7.7 Hz), 7.10 (ddd, 1 H, ArH-4, J₄,₆ 2.8 Hz and J₄,₂ 0.8 Hz), 4.00 (t, 2 H, CH₂-OAr, J 6.6 Hz), 3.92 (s, 3 H, OCH₃), 1.80 (tt, 2 H, ArO-CH₂—CH₂—CH₂, J 6.6 Hz and J 6.4 Hz), 1.52-1.20 (m, 16 H, 8 CH₂), 0.89 (t, 3 H, CH₃, J 6.7 Hz)

¹³C NMR (62.5 MHz, CDCl₃) δ (ppm): 167 (CO₂CH₃), 159 (C-3), 131 (C-1), 129 (C-5), 122 (C-6), 120 (C-4), 115 (C-2), 68 (CH₂—OAr), 52 (CH₃O), 32-23 (9 CH₂), 14 (CH₃)

Mass Spectrum:

Positive ESI m/z=329.2 [M+Na]+

High res. Calc. for C₁₉H₃₀O₃Na: 329.209264, Found: 329.207940

Infrared (cm⁻¹): 2950-2925-2854-1727-1586-1446-1287-1228-756

3-(undecyloxy)benzoic acid (22)

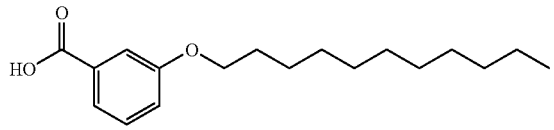 [SMILES: CCCCCCCCCCCOc1cccc(C(=O)O)c1]

600 μL of 1 N sodium hydroxide solution (600 μmol) are added portionwise to 112 mg of 21 (366 μmol) in methanol (4 mL). The solution is refluxed for two hours. After evaporating off the solvent, the reaction medium is acidified with 0.5 N HCl and extracted with DCM. 107 mg of the expected acid are obtained in the form of a white solid, i.e. a yield of 99%.

$^1$H NMR (250 MHz, CDCl$_3$) δ (ppm): 7.70 (d, 1H, ArH-6, J$_{6,5}$ 7.8 Hz), 7.62 (m, 1H, ArH-2), 7.38 (dd, 1H, ArH-5, J$_{5,4}$ 8.0 Hz), 7.16 (dd, 1H, ArH-4, J$_{4,2}$ 2.1 Hz), 4.02 (t, 2H, CH$_2$—OAr, J 6.5 Hz), 1.99 (tt, 2H, ArO-CH$_2$—CH$_2$—CH$_2$, J 6.6 Hz), 1.55-1.20 (m, 16H, 8 CH$_2$), 0.89 (t, 3H, CH$_3$, J 6.5 Hz)

$^{13}$C NMR (62.5 MHz, CDCl$_3$) δ (ppm): 171 (CO$_2$H), 159 (C-3), 130 (C-1), 129 (C-5), 122 (C-6), 121 (C-4), 115 (C-2), 68 (CH$_2$—OAr), 32-23 (9 CH$_2$), 14 (CH$_3$)

Mass Spectrum:

Negative ESI m/z=291.2 [M-H]−

High res. Calc. for C$_{18}$H$_{27}$O$_3$: 291.196020, Found: 291.196560

Infrared (cm$^{-1}$): 2950-2920-2850-2700-2400-1680-1603-1455-1420-1312-1247-757

Melting point: 88° C.

3-(undecanyloxy)benzoyl chloride (2)

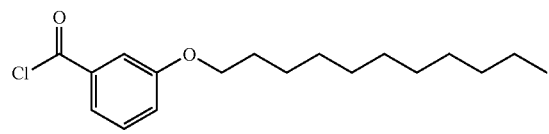 [SMILES: CCCCCCCCCCCOc1cccc(C(=O)Cl)c1]

1 mL of oxalyl chloride (11.5 mmol) and two drops of anhydrous DMF are added under argon to 93 mg of toluene-dried acid 22 (318 μmol) dissolved in 20 mL of anhydrous DCM. The medium is stirred at room temperature for two hours, and then concentrated to give 99 mg of a yellow oil, i.e. a yield of 99%.

methyl 3-(undec-4-ynyloxy)benzoate (25)

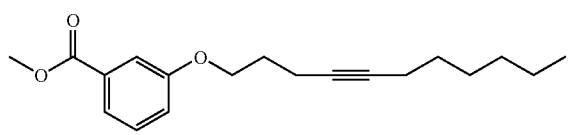 [SMILES: CCCCCCC#CCCCOc1cccc(C(=O)OC)c1]

325 mg of 14 (2.14 mmol) and 300 mg of K$_2$CO$_3$ (2.17 mmol) are added to 600 mg of 24 (2.16 mmol) in anhydrous DMF (7 mL). After reaction for 6 hours at 90° C., the reaction medium is concentrated, washed with DCM and then taken up in water. 639 mg of a yellow oil are obtained, and are chromatographed on silica gel in pentane/ethyl acetate (50/1). 429 mg of a yellow oil are isolated, i.e. a yield of 66%.

$^1$H NMR (200 MHz, CDCl$_3$) δ (ppm): 7.63 (m, 1 H, ArH-6), 7.57 (m, 1 H, ArH-2), 7.31 (dd, 1 H, ArH-5, J$_{5,4}$ 8.1 Hz and J$_{5,6}$ 7.8 Hz), 7.11 (ddd, 1 H, ArH-4, J$_{4,6}$ 2.4 Hz and J$_{4,2}$ 0.8 Hz), 4.11 (t, 2 H, CH$_2$-OAr, J 6.2 Hz), 3.92 (s, 3 H, OCH$_3$), 2.39-2.15 (2 m, 4 H, CH$_2$—C≡C—CH$_2$), 1.98 (tt, 2 H, ArO-CH$_2$—CH$_2$—CH$_2$—C≡C, J 6.5 Hz), 1.52-1.23 (m, 8 H, 4 CH$_2$), 0.88 (t, 3 H, CH$_3$, J 6.7 Hz)

$^{13}$C NMR (62.5 MHz, CDCl$_3$) δ (ppm): 167 (CO$_2$CH$_3$), 159 (C-3), 131 (C-1), 129 (C-5), 122 (C-6), 120 (C-4), 115 (C-2), 81-79 (C≡C), 67 (CH$_2$—OAr), 52 (CH$_3$O), 31-15 (7 CH$_2$), 14 (CH$_3$)

Mass Spectrum:

Positive ESI m/z=325.1 [M+Na]+

High res. Calc. for C$_{19}$H$_{26}$O$_3$Na: 325.177964, Found: 325.178070

Infrared (cm$^{-1}$): 2950-2931-2857-1726-1586-1446-1288-1228-756

3-(undec-4-ynyloxy)benzoic acid (26)

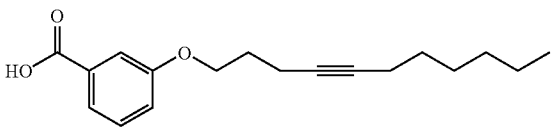 [SMILES: CCCCCCC#CCCCOc1cccc(C(=O)O)c1]

300 μL of 1 N sodium hydroxide solution (300 μmol) are added portionwise to 48 mg of 25 (157 μmol) in methanol (2 mL). The solution is refluxed for 1 hour 30 minutes. After evaporating off the solvent, the reaction medium is acidified with 0.5 N HCl and extracted with DCM. 45 mg of a pale yellow oil are obtained, i.e. a yield of 99%.

$^1$H NMR (250 MHz, CDCl$_3$) δ (ppm): 11.00-10.00 (bd, 1 H, CO$_2$H), 7.72 (d, 1 H, ArH-6, J$_{6,5}$ 7.7 Hz), 7.64 (m, 1 H, ArH-2), 7.38 (dd, 1 H, ArH-5, J$_{5,4}$ 8.1 Hz), 7.17 (dd, 1 H, ArH-4, J$_{4,2}$ 2.7 Hz), 4.13 (t, 2 H, CH$_2$—OAr, J 6.1 Hz), 2.39-2.15 (2 m, 4 H, CH$_2$—C≡C—CH$_2$), 1.99 (tt, 2 H, ArO-CH$_2$—CH$_2$—CH$_2$—C≡C, J 6.5 Hz), 1.50-1.20 (m, 8 H, 4 CH$_2$), 0.88 (t, 3 H, CH$_3$, J 6.7 Hz)

$^{13}$C NMR (62.5 MHz, CDCl$_3$) δ (ppm): 172 (CO$_2$H), 159 (C-3), 131 (C-1), 129 (C-5), 123 (C-6), 121 (C-4), 115 (C-2), 81-79 (C≡C), 67 (CH$_2$—OAr), 31-15 (7 CH$_2$), 14 (CH$_3$)

Mass Spectrum:

Negative ESI m/z=287.1 [M-H]−

High res. Calc. for C$_{18}$H$_{23}$O$_3$: 287.164719, Found: 287.164820

Infrared (cm$^{-1}$): 2954-2929-2855-2700-2400-1690-1592-1452-1414-1288-1247-756

3-(undec-4Z-ynyloxy)benzoyl chloride (27)

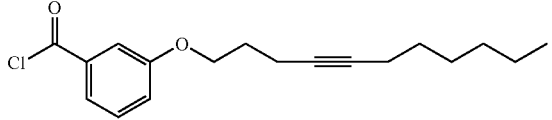 [SMILES: CCCCCCC#CCCCOc1cccc(C(=O)Cl)c1]

850 µL of oxalyl chloride (9.74 mmol) and two drops of anhydrous DMF are added under argon to 80 mg of toluene-dried acid 26 (278 µmol) dissolved in 17 mL of anhydrous DCM. The medium is stirred at room temperature for two hours, and then concentrated to give 85 mg of a yellow oil, i.e. a yield of 99%.

methyl 2-(undec-4Z-enyloxy)benzoate (29)

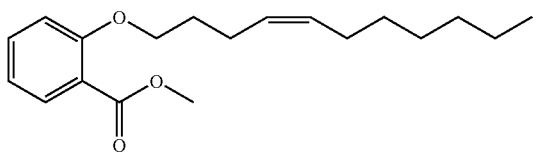 [SMILES: CCCCCC/C=C\CCCOc1ccccc1C(=O)OC]

88 mg of 28 (578 µmol) and 77 mg of $K_2CO_3$ (557 mmol) are added to 140 mg of 13 (500 µmol) in anhydrous DMF (2 mL). After reaction for 8 hours at 90° C., the reaction medium is concentrated, taken up in DCM and then washed with water. 137 mg of a yellow oil are obtained, and are chromatographed on silica gel in pentane/ethyl acetate (40/1). 100 mg of a yellow oil are isolated, i.e. a yield of 66%.

$^1$H NMR (250 MHz, CDCl$_3$) δ (ppm): 7.79 (dd, 1 H, ArH-6, $J_{6.5}$ 8.1 Hz and $J_{6.4}$ 1.9 Hz), 7.43 (ddd, 1 H, ArH-4, $J_{43}$ 8.5 Hz, $J_{4.5}$ 7.3 Hz), 6.94 (m, 2 H, ArH-5 and ArH-3), 5.40 (m, 2 H, CH=CH), 4.02 (t, 2 H, CH$_2$-OAr, J 6.3 Hz), 3.89 (s, 3 H, OCH$_3$), 2.28-2.01 (2 m, 4 H, CH$_2$—CH=CH—CH$_2$, J 6.6 Hz), 1.89 (tt, 2 H, ArO-CH$_2$—CH$_2$—CH$_2$, J 6.6 Hz), 1.50-1.16 (m, 8 H, 4 CH$_2$), 0.86 (t, 3 H, CH$_3$, J 6.6 Hz)

$^{13}$C NMR (62.5 MHz, CDCl$_3$) δ (ppm): 167 (C=O), 158 (C-2), 133 (C-4), 131 (CH=CH), 128 (C-6), 120 (C-1), 119 (C-5), 113 (C-3), 68 (CH$_2$—OAr), 52 (CH$_3$O), 32-22 (7 CH$_2$), 14 (CH$_3$)

Mass Spectrum:
Positive ESI m/z=327.2 [M+Na]+
High res. Calc. for $C_{19}H_{28}O_3Na$: 327.193914, Found: 327.192560

Infrared (cm$^{-1}$): 3000-2962-2925-2855-1734-1601-1491-1456-1305-1250-754

2-(undec-4Z-enyloxy)benzoic acid (3)

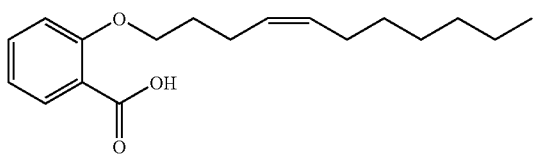 [SMILES: CCCCCC/C=C\CCCOc1ccccc1C(=O)O]

500 µL of 1 N sodium hydroxide solution (500 µmol) are added portionwise to 80 mg of 29 (263 µmol) in methanol (3 mL). The solution is refluxed for 24 hours. After evaporating off the solvent, the reaction medium is acidified with 0.5 N HCl and extracted with DCM. 76 mg of a yellow oil are obtained, i.e. a yield of 99%.

$^1$H NMR (250 MHz, CDCl$_3$) δ (ppm): 12.00-10.00 (bd, 1 H, CO$_2$H), 8.16 (dd, 1 H, ArH-6, $J_{6.5}$ 7.8 Hz and $J_{6.4}$ 1.9 Hz), 7.54 (ddd, 1 H, ArH-4, $J_{43}$ 8.4 Hz and $J_{45}$ 7.6 Hz), 7.10 (ddd, 1 H, ArH-5, $J_{5.3}$ 0.8 Hz), 7.03 (dd, 1 H, ArH-3), 5.40 (m, 2 H, CH=CH), 4.24 (t, 2 H, CH$_2$-OAr, J 6.4 Hz), 2.25 (m, 2 H, CH$_2$—CH=CH—CH$_2$), 1.97 (m, 4 H, ArO-CH$_2$—CH$_2$—CH$_2$—CH=CH—CH$_2$), 1.35-1.10 (m, 8 H, 4 CH$_2$), 0.84 (t, 3 H, CH$_3$, J 6.6 Hz)

$^{13}$C NMR (62.5 MHz, CDCl$_3$) δ (ppm): 165 (CO$_2$H), 157 (C-2), 135 (C-4), 134-132 (CH=CH), 127 (C-6), 122 (C-5), 117 (C-1), 112 (C-3), 69 (CH$_2$—OAr), 32-22 (7 CH$_2$), 14 (CH$_3$)

Mass Spectrum:
Negative ESI m/z=289.2 [M-H]−
High res. Calc. for $C_{18}H_{25}O_3$: 289.180370, Found: 289.179060

2-(undec-4Z-enyloxy)benzoyl chloride (31)

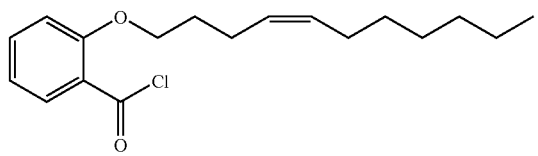 [SMILES: CCCCCC/C=C\CCCOc1ccccc1C(=O)Cl]

800 µL of oxalyl chloride (9.17 mmol) and two drops of anhydrous DMF are added under argon to 76 mg of toluene-dried acid 30 (262 µmol) dissolved in 15 mL of anhydrous DCM. The medium is stirred at room temperature for two hours and then concentrated to give 80 mg of a yellow oil, i.e. a yield of 99%.

$^1$H NMR (250 MHz, CDCl$_3$) δ (ppm): 7.97 (dd, 1 H, ArH-6, $J_{6.5}$ 7.9 Hz and $J_{6.4}$ 1.7 Hz), 7.46 (m, 1 H, ArH-4), 6.90 (m, 2 H, ArH-5 and ArH-3), 5.30 (m, 2 H, CH=CH), 3.95 (t, 2 H, CH$_2$-OAr, J 6.3 Hz), 2.20-1.90 (2 m, 4 H, CH$_2$—CH=CH—CH$_2$), 1.79 (tt, 2 H, ArO-CH$_2$—CH$_2$—CH$_2$—CH=CH, J 6.6 Hz), 1.20-1.09 (m, 8 H, 4 CH$_2$), 0.76 (t, 3 H, CH$_3$, J 6.7 Hz)

methyl 4-(undec-4Z-enyloxy)benzoate (33)

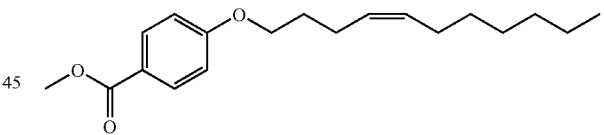

90 mg of 32 (590 µmol) and 81 mg of $K_2CO_3$ (590 µmol) are added to 150 mg of 13 (535 µmol) in anhydrous DMF (2 mL). After reaction for 7 hours at 90° C., the reaction medium is concentrated, taken up in DCM and then washed with water. 163 mg of a yellow oil are obtained, and are chromatographed on silica gel in pentane/ethyl acetate (80/1). 129 mg of the expected coupling product are isolated in the form of a yellow oil, i.e. a yield of 79%.

$^1$H NMR (250 MHz, CDCl$_3$) δ (ppm): 7.97 (d, 2 H, ArH-2 and ArH-6, $J_{6.5}$≈$J_{2.3}$ 8.8 Hz), 6.89 (d, 2 H, ArH-3 and ArH-5), 5.39 (m, 2 H, CH=CH), 3.99 (t, 2 H, CH$_2$-OAr, J 6.3 Hz), 3.88 (s, 3 H, OCH$_3$), 2.22-2.00 (2 m, 4 H, CH$_2$—CH=CH—CH$_2$), 1.84 (tt, 2 H, ArO-CH$_2$—CH$_2$—CH$_2$, J 6.8 Hz), 1.40-1.12 (m, 8 H, 4 CH$_2$), 0.85 (t, 3 H, CH$_3$, J 6.6 Hz)

$^{13}$C NMR (62.5 MHz, CDCl$_3$) δ (ppm): 167 (C=O), 163 (C-4), 131 (C-2 and C-6), 130-128 (CH=CH), 122 (C-1), 114 (C-5 and C-3), 67 (CH$_2$—OAr), 52 (CH$_3$O), 32-23 (7 CH$_2$), 14 (CH$_3$)

Mass Spectrum:

Positive ESI m/z=327.2 [M+Na]+

High res. Calc. for $C_{19}H_{28}O_3Na$: 327.193914, Found: 327.192630

Infrared (cm$^{-1}$): 3000-2962-2925-2855-1720-1607-1511-1435-1279-1254-846

4-(undec-4Z-enyloxy)benzoic acid (14)

550 µL of 1 N sodium hydroxide solution (550 µmol) are added portionwise to 109 mg of 33 (358 µmol) in methanol (4 mL). The solution is refluxed for 20 hours. After evaporating off the solvent, the reaction medium is acidified with 0.5 N HCl and extracted with DCM. 102 mg of a white solid are obtained, i.e. a yield of 98%.

$^1$H NMR (250 MHz, CDCl$_3$) δ (ppm): 12.00-11.00 (bd, 1 H, CO$_2$H), 8.07 (d, 2 H, ArH-2 and ArH-6, $J_{2,3} \approx J_{6,5}$ 8.5 Hz), 6.94 (d, 2 H, ArH-3 and ArH-5), 5.42 (m, 2 H, CH=CH), 4.03 (t, 2 H, CH$_2$—OAr, J 6.3 Hz), 2.26-2.03 (2 m, 4 H, CH$_2$—CH=CH—CH$_2$), 1.88 (tt, 2 H, ArO-CH$_2$—CH$_2$—CH$_2$, J 6.8 Hz), 1.40-1.10 (m, 8 H, 4 CH$_2$), 0.89 (t, 3 H, CH$_3$, J 6.6 Hz)

$^{13}$C NMR (62.5 MHz, CDCl$_3$) δ (ppm): 172 (CO$_2$H), 164 (C-4), 132 (C-2 and C-6), 131-128 (CH=CH), 121 (C-1), 114 (C-3 and C-5), 67 (CH$_2$—OAr), 32-22 (7 CH$_2$), 14 (CH$_3$)

Mass Spectrum:

Negative ESI m/z=289.2 [M-H]-

High res. Calc. for $C_{18}H_{25}O_3$: 289.180370, Found: 289.178710

4-(undec-4Z-enyloxy)benzoyl chloride (35)

1 mL of oxalyl chloride (11.5 mmol) and two drops of anhydrous DMF are added under argon to 101 mg of toluene-dried acid 34 (348 µmol) dissolved in 18 mL of anhydrous DCM. The medium is stirred at room temperature for two hours and then concentrated to give 107 mg of a yellow oil, i.e. a yield of 99%.

$^1$H NMR (250 MHz, CDCl$_3$) δ (ppm): 7.96 (d, 2 H, ArH-2 and ArH-6, $J_{2,3} \approx J_{6,5}$ 8.7 Hz), 6.99 (d, 2 H, ArH-3 and ArH-5), 5.43 (m, 2 H, CH=CH), 4.10 (t, 2 H, CH$_2$—OAr, J 6.3 Hz), 2.27-2.03 (2 m, 4 H, CH$_2$—CH=CH—CH$_2$), 1.91 (tt, 2 H, ArO-CH$_2$—CH$_2$—CH$_2$, J 6.7 Hz), 1.35-1.12 (m, 8 H, 4 CH$_2$), 0.89 (t, 3 H, CH$_3$, J 6.6 Hz)

V. ACTIVITY TESTS

V.1 Activity Tests on Temperate Legumes of the Galegoid Group

Temperate legumes of the Galegoid group are nodulated by *rhizobia* that produce Nod factors with the hydrophobic chain having a double bond conjugated to the carbonyl group. This group includes important legume crops such as alfalfa, pea, broad bean, chickpea and clover.

The compositions are tested on alfalfa for induction of the formation of root nodules, and on the model legume *Medicago truncatula* for induction of the expression of a symbiotic gene coding for an early nodulin.

V.1.1 Nodulation Tests on Alfalfa

Alfalfa plantlets are grown under axenic conditions in test tubes on a nitrogen-poor agar medium (Demont-Caulet et al., Plant Physiol., 120, 83-92, 1999). Untreated plantlets or plantlets treated with natural nod factors or synthetic LCOs serve as control.

V.1.2. Tests of Induction of Early Nodulin on *Medicago truncatula*

These tests are performed to determine whether the compositions induce symbiotic responses by activation of the same signal transduction pathway as the natural Nod factors. The tests are performed on the model legume *Medicago truncatula*. The activity of the compositions is studied on "wild-type" plants and on a mutant in the gene DMI1 which is altered in the transduction of the Nod factor signal (Catoira et al. *Plant Cell*, 12, 1647-1665, 2000). The compound that serves as reference is the sulfated tetramer 12 acylated with the C16:2Δ2E,9Z chain, which is an analog of the natural Nod factor. Untreated plantlets or plantlets treated with natural nod factors or synthetic LCOs alone serve as control.

V.1.2.1 Reporter Gene

It is generally difficult to determine the regulation of expression of a particular gene, during a biological process, since most of the specific products of these genes are not readily detectable or measurable. To overcome this problem, a technique of fusion with "reporter genes" is used, i.e. genes coding for a readily assayable protein. The fusion consists in combining the DNA sequence containing the gene regulatory regions that it is desired to study, with the DNA sequence of the reporter gene. The assembly is then reintroduced into the plant by transformation. Thus, if the target gene is expressed, the reporter gene is automatically expressed. It is then a matter of assaying the reporter gene protein.

In order to avoid a negative interaction with the activity of the plant, reporter genes that do not code for any enzyme normally formed by the plants are used. One of the enzymes most commonly used is O-glucuronidase (GUS) from *Escherichia coli*, a hydrolase that catalyzes the cleavage of a large variety of β-glucuronides. As commercial substrate of this enzyme, it is possible to use:

X-Gluc (Sigma B-4782): 5-bromo-4-chloro-3-indolyl glucuronide; the anion formed has a blue color.

-continued

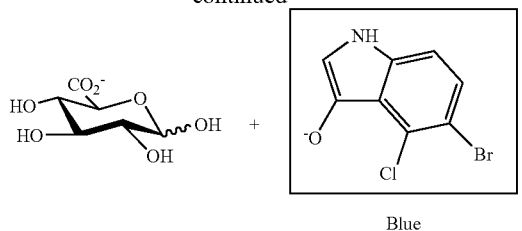

Blue

V.1.2.2 Enod11::GUSA

The genes for the legumes involved in modulation may be classified into two major types:
early nodulin genes (ENOD), which are activated in the first days of the infection and activation of the nodulation process; late nodulin genes, which are not activated until several days after the application of the bacteria, and do not intervene until the period of maturation of the nodules.

A new gene of *Medicago truncatula*, *MtENOD*11, coding for an RPRP (Repetitive proline-rich protein), and transcribed during the first steps of infection of nodulation on the nodule roots and tissues was identified (Journet et al. *Mol. Plant-Microbe Interact.*, 14, 737-748, 2001). Using the transgenic *Medicago truncatula* plant expressing the fusion MtENOD11::GUSA, it is possible to determine whether a composition added to the culture medium of the plant has induced transcription of the ENOD11 gene.

For the ENOD11 transcription tests, a Fahraeus medium is used as for The modulation tests, but without agar. The seedlings are placed on paper in pockets containing the culture medium. The responses of two types of transgenic plants bearing the MtENOD11::GUS: fusion are compared: a "wild-type" (WT) Jemalong plant and a plant bearing a mutation in the DM11 gene, which is incapable of transducing the Nod factor signal. The plants are left to grow for 5 days and the plantlets are then treated with various concentrations of LCO. After 6 hours, the plantlets are removed and placed in aqueous medium containing X-Gluc for 1 to 2 hours. The number of roots giving a characteristic blue response is then counted.

This test is relatively sensitive, to the extent that it is possible to work at LCO concentrations that are lower than those for the nodulation tests.

V.2 Activity Tests on Other Legumes

*Lotus corniculatus* is a forage crop which is nodulated by *rhizobia* which produce Nod factors quite similar to those produced by *rhizobia* which nodulate soybean: the chitin oligomer backbone has five glucosamine residues, the N-acyl chain is essentially vaccenic acid (C18:1) and the reducing glucosamine residue is not sulfated and is O-substituted by a fucosyl residue. *Lotus corniculatus* was chosen as a model system because seeds and seedlings are small sized and convenient to handle.

V.2.1 Root Hair Deformation Assay on *Lotus corniculatus*

Seeds of *Lotus corniculatus* (cv Rodeo) were sterilized. Germinated seeds with rootlets about 1 cm long were aseptically transferred onto Farhaeus soft agar plates. Plates were sealed with Parafilm and placed vertically for two days in a plant growth chamber (at 25° C., with a 16-hr light period, a relative humidity of 75%, OsramVFluora L 77 as the type of light, and light intensity at the level of the top of the plates of 30 µE.m−2.s−1) to allow plant growth and root hair development. Then 2 ml of a Nod factor derivative sterile solution was poured to cover the *Lotus* root system, and after 30 nm, excess liquid was removed. A further incubation was performed for 16 hr in the plant growth chamber. The roots of the five plants were transferred between slide and cover slip and observed by bright field microscopy after staining by methylene blue.

To estimate the plant response, a criterion of clear-cut hair branching was chosen (numerous branching at more than one site on the root system), and plants exhibiting these pronounced reactions were classified as <<+>>. The statistical significance (at the P=0.05) of the proportion of <<+>> responses was calculated using the ratio comparisons based on the Fisher's <<Exact>> test (SAS software).

V.3 In Vitro Test

V 3.1 Calculation of the Efficacy

The expected efficacy of a given combination of two compounds is calculated as follows (see Colby, S. R., "Calculating Synergistic and antagonistic Responses of Herbicide Combinations", Weeds 15, pp. 20-22, 1967):

If

X is the efficacy expressed in % mortality of the untreated control for test compound A at a concentration of m ppm respectively m g/ha;

Y is the efficacy expressed in % mortality of the untreated control for test compound B at a concentration of n ppm respectively n g/ha;

E is the efficacy expressed in % mortality of the untreated control using the mixture of A and B at m and n ppm respectively m and n g/ha;

then is $$E = X + Y - \frac{X \times Y}{100}$$

If the observed insecticidal efficacy of the combination is higher than the one calculated as "E", then the combination of the two compounds is more than additive, i.e., there is a synergistic effect.

V.3.2 Test on *Myzus persicae*

| Solvent: | 7 parts by weight of dimethylformamide |
|---|---|
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration. Cabbage leaves (*Brassica oleracea*) which are heavily infested by the green peach aphid (*Myzus persicae*) are treated by being dipped into the preparation of the active compound of the desired concentration.

After the specified period of time, the mortality in % is determined. 100% means that all the aphids have been killed; 0% means that none of the aphids have been killed.

According to the present application in this test e.g. the following combination shows a synergistic effect in comparison to the single compounds:

TABLE A plant damaging insects
*Myzus persicae*-test

| active compound | active compound concentration in ppm | mortality in % after $4^d$ | |
|---|---|---|---|
| compound A: | 0.00003 | 0 | |
|  | 0.000003 | 0 | |

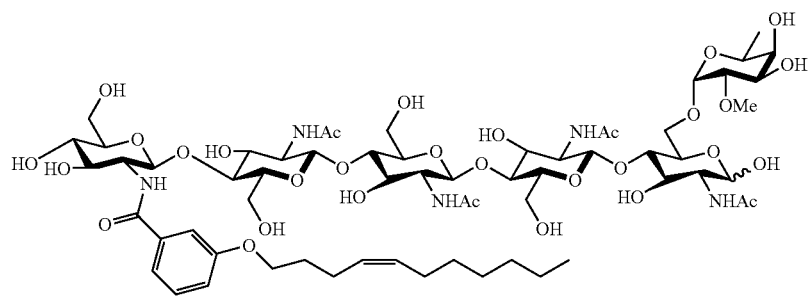

| | | | |
|---|---|---|---|
| Imidacloprid | 0.16 | 10 | |
| Compound A + Imidacloprid (1:5333.3) | 0.00003 + 0.16 | obs.* 92.5 | cal.** 10 |
| Compound A + Imidacloprid (1:53333.3) according to the invention | 0.000003 + 0.16 | obs.* 97.5 | cal.** 10 |

*obs. = observed insecticidal efficacy
**cal. = efficacy calculated with Colby-formula V.3.2 Test on *Phaedon cochleariae*

| Solvent: | 7 parts by weight of dimethylformamide |
|---|---|
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration. Cabbage leaves (*Brassica oleracea*) are treated by being dipped into the preparation of the active compound of the desired concentration and are infested with larvae of the mustard beetle (*Phaedon cochleariae*) as long as the leaves are still moist.

After the specified period of time, the mortality in % is determined. 100% means that all the beetle larvae have been killed; 0% means that none of the beetle larvae have been killed.

According to the present application in this test e.g. the following combination shows a synergistic effect in comparison to the single compounds:

TABLE B plant damaging insects
*Phaedon cochleariae* test

| active compound | active compound concentration in ppm | mortality in % after $4^d$ | |
|---|---|---|---|
| Compound A: | 0.00003 | 0 | |
|  | 0.000003 | 0 | |

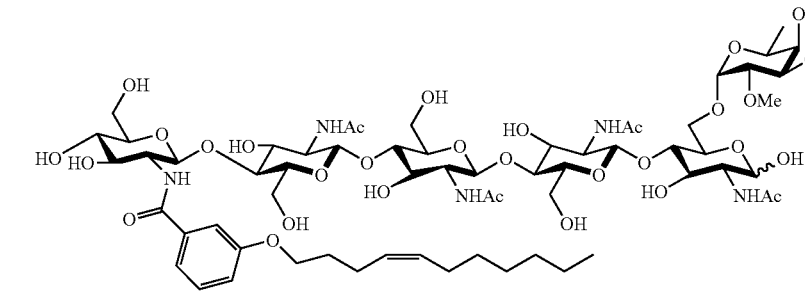

| | | | |
|---|---|---|---|
| Imidacloprid | 20 | 70 | |
| Compound A + Imidacloprid (1:666666.67) | 0.00003 + 20 | obs.* 90 | cal.** 70 |
| Compound A + Imidacloprid (1:6666666.67) | 0.000003 + 20 | obs.* 100 | cal.** 70 |

*obs. = observed insecticidal efficacy
**cal. = efficacy calculated with Colby-formula

The invention claimed is:
1. A composition comprising:
(a) a compound selected from the group consisting of

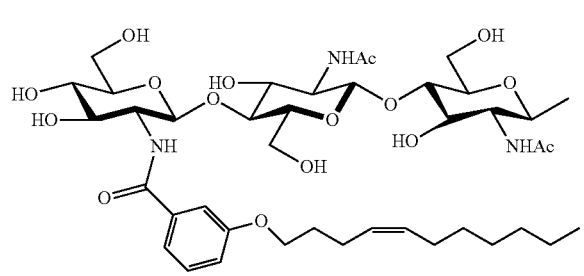

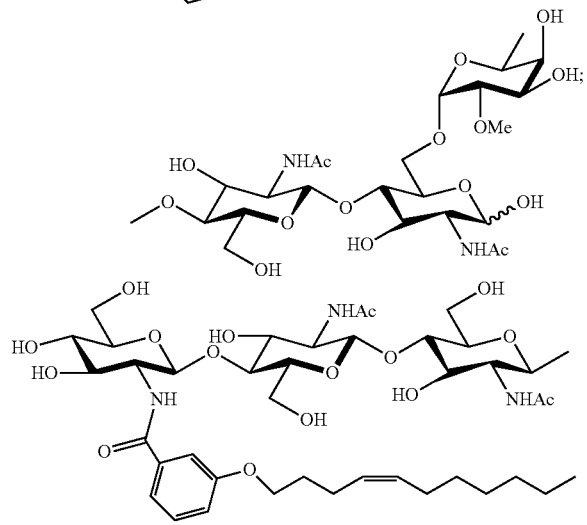

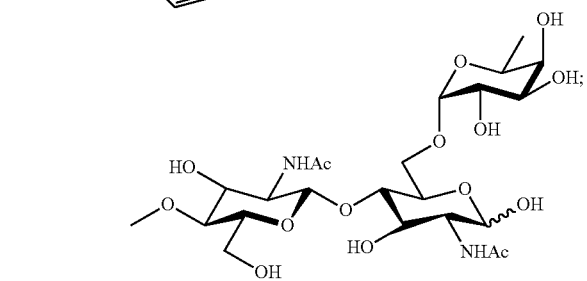

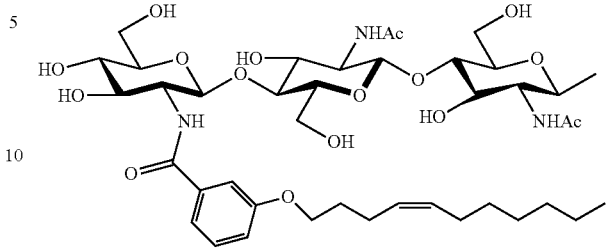

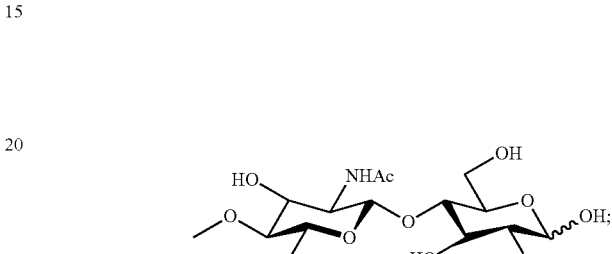

and any agriculturally acceptable geometrical and/or optical isomer, enantiomer and/or diastereoisomer, tautomer, salt, or N-oxide thereof; and (b) an insecticidal chloronicotinyl/neonicotinoid compound selected from the group consisting of clothianidin and imidacloprid;

in an (a)/(b) weight ratio of from $1/10^2$ to $1/10^7$.

2. The composition of claim 1 wherein the salt is selected from the group consisting of lithium, sodium, potassium, and tetraalkylammonium salts.

3. The composition of claim 1 wherein compound (a) is:

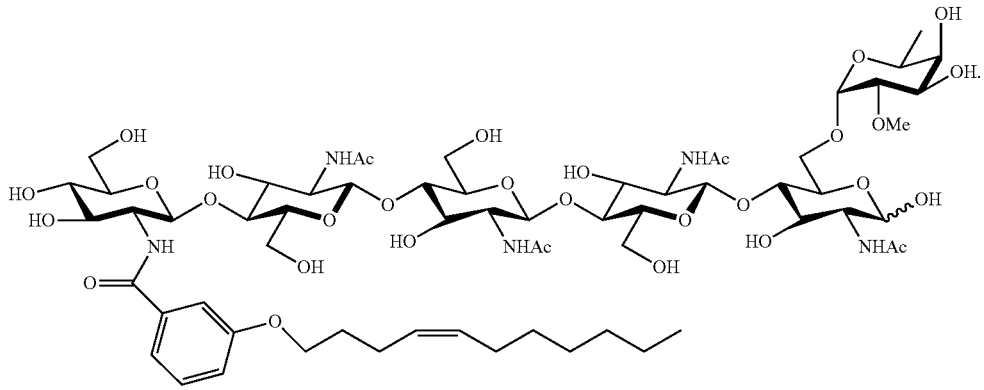

4. The composition of claim 1 wherein compound (a) is:

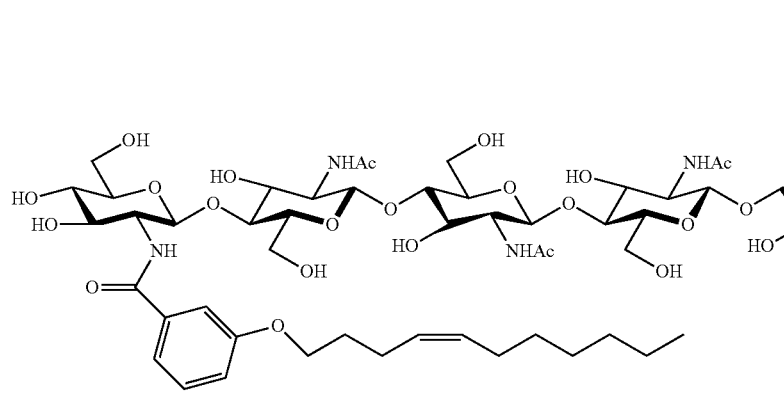

5. The composition of claim 1 wherein compound (a) is:

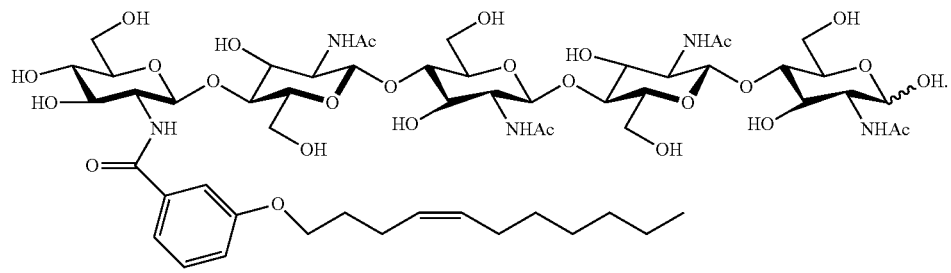

6. The composition of claim 1 wherein the insecticide compound (b) is imidacloprid.

7. The composition of claim 1 wherein the insecticide compound (b) is clothianidin.

8. The composition of claim 1 further comprising an agriculturally acceptable support, carrier, filler and/or surfactant.

9. The composition of claim 1 further comprising a fungicide compound (c) that is different from the insecticidal ingredient selected as (b).

10. The composition of claim 9 wherein compounds (a), (b), and (c) are present in an amount of (a)/(b)/(c) weight ratio of from $1/100/100$ to $1/10^7/10^8$.

11. The composition of claim 9, wherein the fungicide compound (c) is selected from the group consisting of N-[2-(1,3-dimethylbutyl)phenyl]-5-fluoro-1,3-dimethyl-1H-pyrazole-4-carboxamide, metalaxyl, carbendazim, pencycuron, fenamidone, fluoxastrobin, trifloxystrobin, pyrimethanil, iprodione, bitertanol, fluquinconazole, ipconazole, prochloraz, prothioconazole, tebuconazole, triadimenol, triticonazole, carpropamid, tolyltluanid, fluopicolide, isotianil, N-{2-[1,1'-bi(cyclopropyl)-2-yl]phenyl}-3-(difluoromethyl)-1H-pyrazole-4-carboxamide, 1-methyl-1H-pyrazole-4-carboxamide, propamocarb fosetylate, triazoxide, N-{3',4'-dichloro-5-fluorobiphenyl-2-yl]-3-[difluoromethyl]-1-methyl-1H-pyrazole-4-carboxamide, and N-{2-[3-chloro-5-(trifluoromethyl)pyridine-2-yl]ethyl}-2-(trifluoromethyl)benzamide.

12. The composition of claim 11, wherein the fungicide compound (c) is tebuconazole.

13. The composition of claim 1 used for controlling phytopathogenic insects and increasing the nodulation for a plant.

14. The composition of claim 13 wherein said plant is a legume.

15. The composition of claim 1 used for controlling insects and increasing the yield of a crop.

16. The composition of claim 1 used for controlling insects and as a plant growth stimulation factor.

17. A method for controlling insects and increasing the yield of crops comprising applying an effective and non-phytotoxic amount of the composition of claim 1 via seed treatment, foliar application, stem application or drench/drip application to the seed, the plant and/or to the fruit of the plant or to soil and/or to inert substrate, pumice, pyroclastic materials/tuff, synthetic organic substrates, organic substrates and/or to a liquid substrate in which the plant is growing or in which it is desired to grow.

18. The method of claim 17 wherein the composition is applied in furrow on the soil.

* * * * *